United States Patent
Rice et al.

(10) Patent No.: US 11,352,365 B2
(45) Date of Patent: Jun. 7, 2022

(54) BIASED POTENT OPIOID-LIKE AGONISTS AS IMPROVED MEDICATIONS TO TREAT CHRONIC AND ACUTE PAIN AND METHODS OF USING THE SAME

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Kenner Cralle Rice, Bethesda, MD (US); Arthur E. Jacobson, Rockville, MD (US); Fuying Li, Shanghai (CN); Eugene S. Gutman, Holland, PA (US); Eric W. Bow, Washington, DC (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/982,196

(22) PCT Filed: Mar. 18, 2019

(86) PCT No.: PCT/US2019/022701
§ 371 (c)(1),
(2) Date: Sep. 18, 2020

(87) PCT Pub. No.: WO2019/182950
PCT Pub. Date: Sep. 26, 2019

(65) Prior Publication Data
US 2021/0024532 A1 Jan. 28, 2021

Related U.S. Application Data

(60) Provisional application No. 62/644,791, filed on Mar. 19, 2018.

(51) Int. Cl.
C07D 491/08 (2006.01)
A61P 29/00 (2006.01)

(52) U.S. Cl.
CPC ............ C07D 491/08 (2013.01); A61P 29/00 (2018.01)

(58) Field of Classification Search
CPC ............................... C07D 491/08; A61P 29/00
USPC .......................................................... 546/63
See application file for complete search history.

(56) References Cited

FOREIGN PATENT DOCUMENTS

| WO | 02060445 A1 | 8/2002 |
|----|----|----|
| WO | 2004089909 A1 | 10/2004 |
| WO | 2005090350 A1 | 9/2005 |
| WO | 2006116311 A2 | 11/2006 |

OTHER PUBLICATIONS

Anne-Cecile Hiebel et al., "Probes for Narcotic Receptor Mediated Phenomena. 34. Synthesis and Structure-Activity Relationships of a Potent u-Agonist s-Antagonist and an Exceedingly Potent Antinociceptive in the Enantiomeric C9-Substituted 5-(3-Hydroxyphenyl)-N-phenylethylmorphan Series", Journal of Medicinal Chemistry, vol. 50, No. 16, 2007, 12 pages.
Eugene S. Gutman et al. , "G-Protein biased opioid agonists: 3-hydroxy-N-phenethyl-5-phenylmorphans with three-carbon chain substituents at C9", Royal Society of Chemistry, RSC Medicinal Chemistry, Jun. 12, 2020, 9 pages.
F. Ivy Carroll et al., "4B-Methyl-5-(3-hydroxyphenyl)morphan Opioid Agonist and Partial Agonist Derived from a 4B-Methyl-5-(3-hydroxyphenyl)morphan Pure Antagonist", Journal of Medicinal Chemistry, vol. 56, 2013, 8 pages.
Hwan Jung Lim et al., "Probes for narcotic receptor mediated phenomena. 48. C7- and C8-substituted 5-phenylmorphan opioids from diastereoselective alkylation", European Journal of Medicinal Chemistry, vol. 67, 2013, 9 pages.
International Search Report issued in Application No. PCT/US2019/022701 dated Jul. 12, 2019, 10 pages.
Mark Froimowitz et al., "Phenylmorphans an Analogues: Opioid Receptor Subtype Selectivity and Effect on Conformation on Activity", Journal of Medicinal Chemistry, vol. 35, No. 9, 1992, 5 pages.
Meining Wang et al., "The Intriguing Effects of Substituents in the N-Phenethyl Moiety of Norhydromorphone: A Bifunctional Opioid from a Set of "Tail Wags Dog" Experiments", Molucules. vol. 25, 2020, 31 pages.
Phong M. Truong et al., "Modulation of opioid receptor affinity and efficacy via N-substitution of 9B-hydroxy-5-(3-hydroxyphenyl)morphan: Synthesis and computer simulation study", Bioorganic & Medicinal Chemistry, vol. 25, 2017, 17 pages.

(Continued)

*Primary Examiner* — Taofiq A Solola
(74) *Attorney, Agent, or Firm* — McBee Moore & Vanik IP, LLC

(57) ABSTRACT

The present invention is directed to a compound having Formula (I) and its enantiomer: wherein the definitions of n, R, X, Y and $Y^3$, and Z are provided in the disclosure. The invention is also directed to pharmaceutical compositions of the disclosed compounds, as well as their use as opioid-like agonists in the treatment of pain.

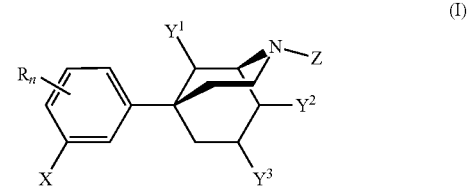

(I)

25 Claims, 19 Drawing Sheets

(56) References Cited

OTHER PUBLICATIONS

Shinichi Kodato et al., "Synthesis of rac-(1R,4aR,9aR)-2-methyl-1,3,4,9a-tetrahydro-2H-1,4a-propanobenzofuro [2,3-c]pyridin-6-ol. An unusual double rearrangement leading to the ortho-and para-f oxide-bridged phenylmorphan somers", Org. Biomol. Chem., vol. 2, 2004, 7 pages.
Written Opinion issued in Application No. PCT/US2019/022701 dated Jul. 12, 2019, 13 pages.

FIG. 2

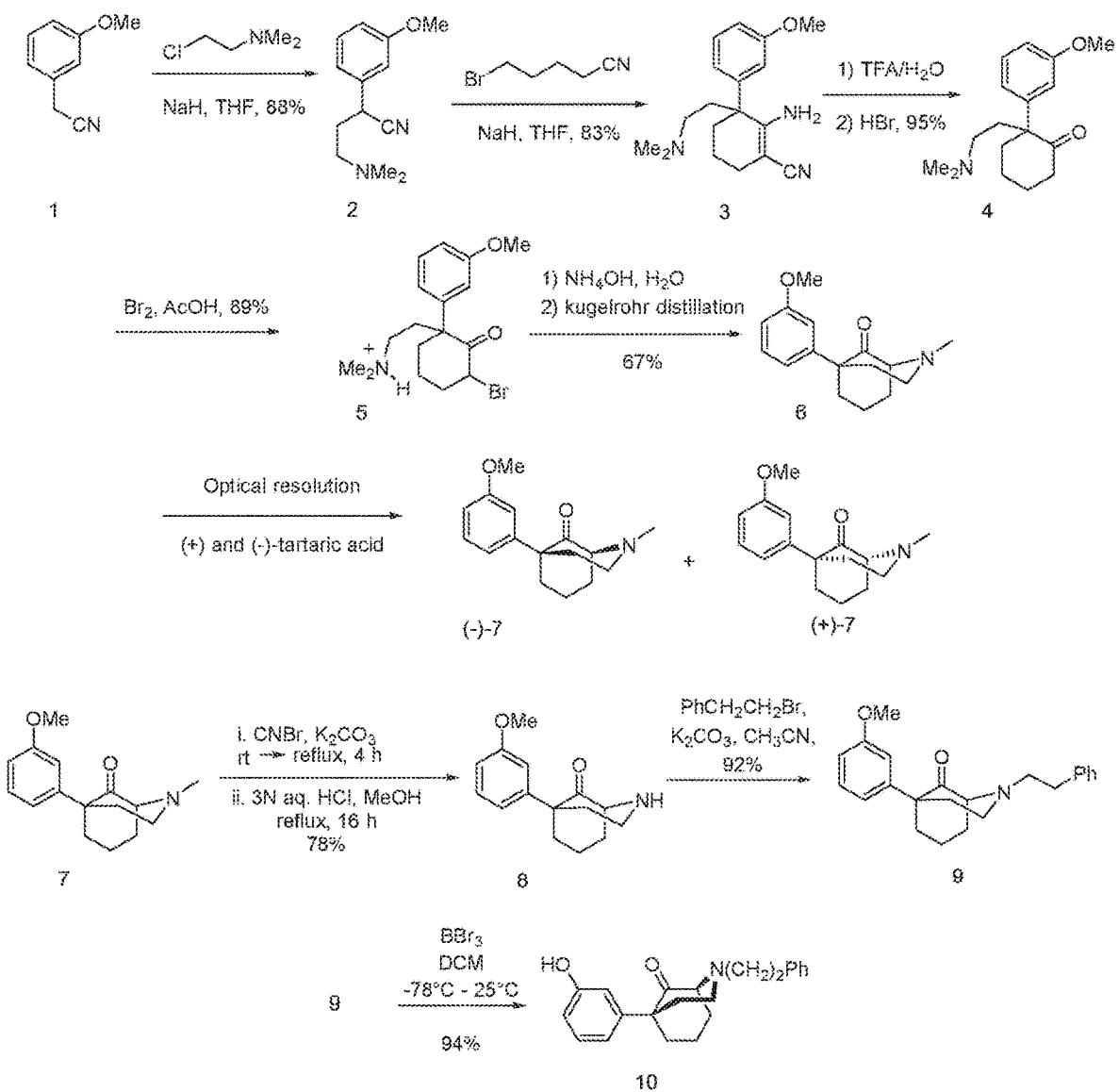

Experimental details for Compounds 1-10 were published in: Hiebel, A.-C.; Lee, Y. S.; Bilsky, E.; Giuvelis, D.; Deschamps, J. R.; Aceto, M. D.; May, E. L.; Harris, L. S.; Coop, A.; Dersch, C. M.; Partilla, J. S.; Rothman, R. B.; Cheng, K.; Jacobson, A. E.; Rice, K. C.: Probes for Narcotic Receptor Mediated Phenomena. 34. Synthesis and Structure-Activity Relationships of a Potent µ-Agonist δAntagonist and an Exceedingly Potent Antinociceptive in the Enantiomeric 9-Substituted 5-(3-Hydroxyphenyl)-N-phenylethylmorphan Series. J. Med. Chem., 50:3765-3776 (2007).

General structures 10 – 14 include all possible stereoisomers/isomers/enantiomers/diasteromers General structures 12-15 include all possible stereoisomers/isomers/enantiomers/diasteromers General structures 12-22 include all possible stereoisomers/isomers/enantiomers/diasteromers General structures 23-28 include all possible stereoisomers/isomers/enantiomers/diasteromers General structures 31-35 include all possible stereoisomers/isomers/enantiomers/diasteromers General structures 38-45 include all possible stereoisomers/isomers/enantiomers/diasteromers

FIG. 10

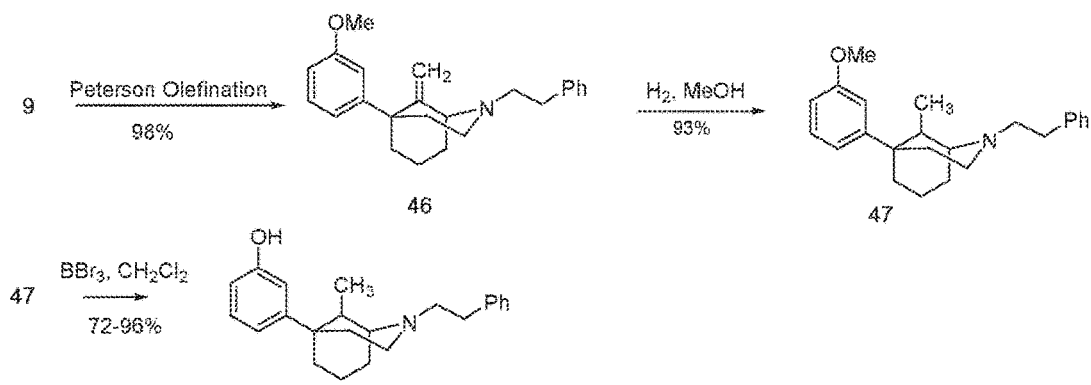

(+)-48 and (-)-48 (see reference)

General structures 46-48 include all possible stereoisomers/isomers/enantiomers/diasteromers (+)-48 and (-)-48 are described in Hiebel, A. C.; Lee, Y. S.; Bilsky, E. J.; Giuvelis, D.; Deschamps, J. R.; Parrish, D. A.; Aceto, M. D.; May, E. L.; Harris, E. M.; Coop, A.; Dersch, C. M.; Partilla, J. S.; Rothman, R. B.; Jacobson, A. E.; Rice, K. C. Probes for narcotic receptor mediated phenomena. 34. Synthesis and structure-activity relationships of a potent N-phenylethylmorphan series. *J.Med.Chem.* 2007, *50*, 3765-3776. The experimental details for these two compounds are shown in the reference.

The synthesis of compound 49 was reported in: Truong, P. M., Hassan, S., Lee, Y.-S., Kopajtic, T. A., Katz, J. L., Chadderdon, A. M., Traynor, J.R., Deschamps, J. R.; Jacobson, A. E.; Rice, K. C.: Modulation of Opioid Receptor Affinity and Efficacy via N-Substitution of 9-*Hydroxy-5-(3-hydroxyphenyl)morphan: Synthesis and Computer Simulation Study*. *Bioorg. Med. Chem.*, 2017, 25, 2406-2422.

The synthesis of compounds 53-66 was published in: Tadic, D.; Linders, J. T. M.; Flippen-Anderson, J. L.; Jacobson, A. E.; Rice, D. C.: Probes for narcotic receptor mediated phenomena. 31. Synthesis of rac-(3R,6aS,11aS)-2-methyl-1,3,4,5,6,11a-hexahydro-2H-3,6a-methanobenzofuro[2,3-c]azocine-10-ol, and azocine-8-ol, the ortho-c and the para-c oxide-bridged phenylmorphan isomers. Tetrahedron 59:4603-4614 (2003).

FIG. 13
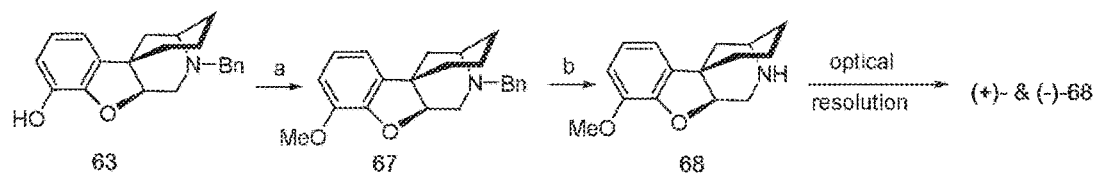
Reagents & conditions: a) MeI, K₂CO₃, DMF, rt, overnight, 88%; b) H₂, 5% Pd/C, 50 °C, MeO/AcOH (10:1, v/v, overnight, 93%
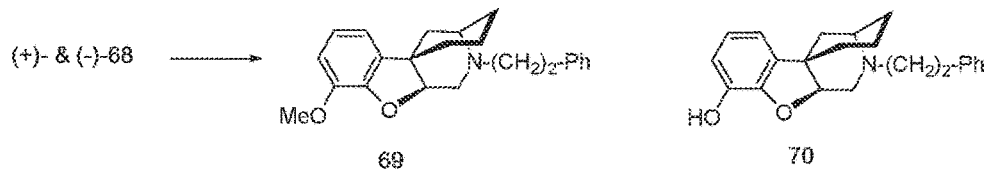
Reagents & conditions: a) Ph(CH₂)₂Br, K₂CO₃, CH₃CN, 80 °C, overnight, 85%; b) BBr₃, CHCl₃, -78 °C to rt, 1 h, 87%

BIASED POTENT OPIOID-LIKE AGONISTS AS IMPROVED MEDICATIONS TO TREAT CHRONIC AND ACUTE PAIN AND METHODS OF USING THE SAME

CROSS-REFERENCE TO RELATED APPLICATIONS

This Application is a U.S. National Stage Application of PCT/US2019/022701 filed Mar. 18, 2019 which claims benefit of U.S. Provisional Application No. 62/644,791 filed Mar. 19, 2018, both of which are incorporated by reference in their entirety.

FIELD OF THE INVENTION

The present invention relates to conformationally constrained 4-aryl-piperidine compounds, pharmaceutical compositions containing these compounds, and methods of their use.

BRIEF DESCRIPTION OF THE ART

Opioid-like analgesics (opiates) are widely used to treat acute and chronic pain in patients. They are known to target three types of endogenous opioid receptors—μ (mu), δ (delta), and κ (kappa) receptors. Many opiates are mu-opioid agonists that are often used for treatment of severe pain due to activation of mu-opioid receptors in the brain and central nervous system (CNS). However, opioid receptors are not limited to CNS, and may be found in other tissues throughout the body. Activation of these "peripheral" receptors by opioid drugs may cause various side effects. Specifically, opioids are generally known to cause nausea and vomiting, as well as inhibition of normal propulsive gastrointestinal function in human and animals which results in constipation.

From molecular biology perspective, classic opioid-like analgesics, such as morphine, activate both G-protein signaling pathways and beta-arrestin signaling pathways. It is generally known that G-protein pathway activation mediates the desirable effects of morphine (analgesia), whereas the beta-arrestin pathway mediates the undesirable effects, such as respiratory depression, constipation, tolerance, and dependence. It has been postulated that the compounds activating only the G-protein pathway would retain the desired analgesic effects of opioids, while producing only minor or no adverse manifestations. Currently, only two compounds ("TRV-130" and "PZM-21") have been shown to conform to this profile, and only one of them ("TRV-130", having clinical name "Oliceridine") is being investigated in human patients. There still remains a need for an efficacious analgesics without undesirable side effects.

SUMMARY OF THE INVENTION

In one aspect, the present invention is directed to a compound having Formula (I) and its enantiomer:

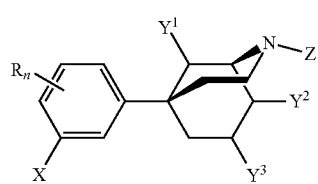

(I)

wherein in Formula (I),
X is —OR$^1$, —NR$^1$R$^2$, —CO$_2$R$^1$, —CONR$^1$R$^2$, or —(CR$^1$R$^2$)$_{m1}$OH; wherein
each R is H, a substituted or unsubstituted C$_3$-C$_{30}$ alkyl, a substituted or unsubstituted C$_3$-C$_{30}$ cycloalkyl, or a substituted or unsubstituted C$_6$-C$_{30}$ aryl; and
each R$^2$ is H, a substituted or unsubstituted C$_1$-C$_{30}$ alkyl, a substituted or unsubstituted C$_3$-C$_{30}$ cycloalkyl, a substituted or unsubstituted C$_2$-C$_{30}$ alkanoyl, a substituted or unsubstituted C$_4$-C$_{30}$ cycloalkanoyl, or a substituted or unsubstituted C$_6$-C$_{30}$ aryl; and
m1 is an integer of 1 to 10;
Y$^1$, Y$^2$, and Y$^3$ are each independently H, C$_1$-C$_{10}$ alkyl, —(CR$^3$R$^4$)$_{m2}$V, —O(CR$^3$R$^4$)$_{m2}$V, or —N(CR$^3$R$^4$)$_{m2}$V, provided that at least one selected from Y$^1$, Y$^2$, and Y$^3$ is —(CR$^3$R$^4$)$_{m2}$V, —O(CR$^3$R$^4$)$_{m2}$V, or —N(CR$^3$R$^4$)$_{m2}$V;
wherein
R$^3$ and R$^4$ are each independently H, a substituted or unsubstituted C$_1$-C$_{30}$ alkyl, a substituted or unsubstituted C$_1$-C$_{30}$ alkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted C$_3$-C$_{30}$ cycloalkyl, a substituted or unsubstituted C$_3$-C$_{30}$ cycloalkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted C$_6$-C$_{30}$ aryl, or a substituted or unsubstituted C$_1$-C$_{30}$ heteroaryl;
V is —COR$^5$, —C(O)OR$^5$, —OC(O)OR$^5$, —OR$^5$, —C(O)NR$^5$R$^6$, —OC(O)NR$^5$R$^6$, —NR$^5$R$^6$, wherein each R$^5$ is H, a substituted or unsubstituted C$_1$-C$_{30}$ alkyl, a substituted or unsubstituted C$_1$-C$_{30}$ alkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted C$_3$-C$_{30}$ cycloalkyl, a substituted or unsubstituted C$_3$-C$_{30}$ cycloalkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, or a substituted or unsubstituted C$_6$-C$_{30}$ aryl; and each R$^6$ is H, a substituted or unsubstituted C$_1$-C$_{30}$ alkyl, a substituted or unsubstituted C$_3$-C$_{30}$ cycloalkyl, a substituted or unsubstituted C$_2$-C$_{30}$ alkanoyl, a substituted or unsubstituted C$_4$-C$_{30}$ cycloalkanoyl, or a substituted or unsubstituted C$_6$-C$_{30}$ aryl; and
m2 is an integer of 1 to 10; and
is H, -L-W, or —(CR$^7$R$^8$)$_{m3}$W; wherein
L is a substituted or unsubstituted C$_2$-C$_{10}$ alkenylene or a substituted or unsubstituted C$_2$-C$_{10}$ alkynylene;
R$^7$ and R$^8$ are each independently H, a substituted or unsubstituted C$_1$-C$_{30}$ alkyl, a substituted or unsubstituted C$_3$-C$_{30}$ cycloalkyl, a substituted or unsubstituted C$_6$-C$_{30}$ aryl, or a substituted or unsubstituted C$_1$-C$_{30}$ heteroaryl, wherein any two selected from $R^7$ and $R^8$ are optionally bonded together to form a ring;

W is H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl; and m3 is an integer of 1 to 10;

R is halogen or a substituted or unsubstituted $C_1$-$C_{30}$ alkyl; and n is an integer of 1 to 4.

In another aspect, the present invention is directed to a pharmaceutical composition, including a therapeutically effective amount of the above compound or its enantiomer together with a pharmaceutically acceptable carrier.

In yet another aspect, the present invention is directed to a method of binding an opioid receptor in a patient in need thereof, comprising administering to the patient a composition comprising a therapeutically effective amount of the above compound or its enantiomer, optionally in combination with one or more additional active ingredients.

These and other aspects will become apparent upon reading the following detailed description of the invention.

BRIEF DESCRIPTION OF THE DRAWINGS

The following description of the invention will be better understood when taken in conjunction with the following drawings in which:

FIG. 2 shows a synthesis of exemplary compound 10;

FIG. 10 shows a synthesis of exemplary compound (+)-48 and (−)-48;

FIG. 13 shows a synthesis of exemplary compound 70;

DETAILED DESCRIPTION

Terminology

Figure 1:
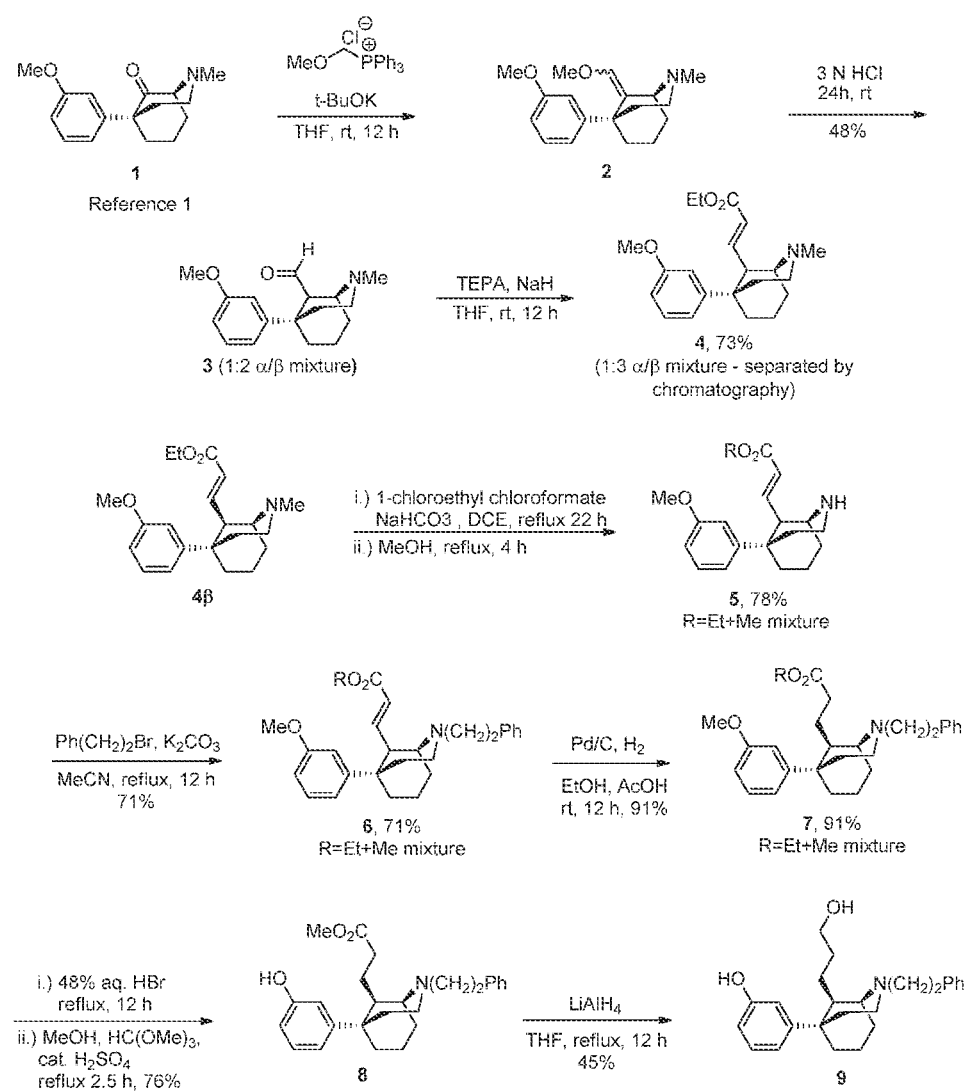
FIG. 1 shows a synthesis of exemplary compounds 8 and 9.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}C$, $^{13}C$, and $^{14}C$. Accordingly, the compounds disclosed herein may include heavy or radioactive isotopes in the structure of the compounds or as substituents attached thereto. Examples of useful heavy or radioactive isotopes include 18F, $^{15}N$, $^{18}O$, 76Br, 125I, and Formulae I, Ia, Ib, II, III, IV, V, and VI include all pharmaceutically acceptable salts of Formulae I, Ia, Ib, II, III, IV, V, and VI.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" refers to a group derived from a straight or branched chain saturated aliphatic hydrocarbon having the specified number of carbon atoms and having a valence of one, optionally substituted with one or more substituents where indicated, provided that the valence of the alkyl group is not exceeded.

"Cycloalkyl" refers to a group that comprises one or more saturated and/or partially saturated rings in which all ring members are carbon, the group having the specified number of carbon atoms. Cycloalkyl groups do not include an aromatic ring or a heterocyclic ring.

"Alkanoyl" refers to a group having formula "alkyl-C(=O)—", wherein "alkyl" is the same as defined above.

"Cycloalkanoyl" refers to a group having formula "cycloalkyl-C(=O)—", wherein "cycloalkyl" is the same as defined above.

"Aryl" refers to a cyclic group in which all ring members are carbon and all rings are aromatic, the group having the specified number of carbon atoms, and having a valence of one, optionally substituted with one or more substituents where indicated, provided that the valence of the aryl group is not exceeded. More than one ring may be present, and any additional rings may be fused, pendant, spirocyclic, or a combination thereof.

"Heteroaryl" means a monovalent carbocyclic ring group that includes one or more aromatic rings, in which at least one ring member (e.g., one, two or three ring members) is a heteroatom selected from nitrogen (N), oxygen (O), sulfur (S), and phosphorus (P), the group having the specified number of carbon atoms.

"Halogen" means fluoro, chloro, bromo, or iodo, and are defined herein to include all isotopes of the same, including heavy isotopes and radioactive isotopes. Examples of useful halo isotopes include $^{18}F$, $^{76}Br$, and $^{131}I$. Additional isotopes will be readily appreciated by one of skill in the art.

"Substituted" means that the compound or group is substituted with at least one (e.g., 1, 2, 3, or 4) substituent independently selected from a halogen (—F, Cl, —Br, —I), a hydroxyl (—OH), a $C_1$-$C_9$ alkoxy, a $C_1$-$C_9$ haloalkoxy, an oxo (=O), a nitro (—NO$_2$), a cyano (—CN), an amino (—NR$_2$, wherein each R is independently hydrogen or $C_1$-$C_{10}$ alkyl), an azido (—N$_3$), an amidino (—C(=NH)NH$_2$), a hydrazino (—NHNH$_2$), a hydrazono (—C(=NNH$_2$)—), a carbonyl (—C(=O)—), a carbamoyl group (—C(O)NH$_2$), a sulfonyl (—S(=O)$_2$—), a thiol (—SH), a thiocyano (—SCN), a tosyl (CH$_3$C$_6$H$_4$SO$_2$—), a carboxylic acid (—C(=O)OH), a carboxylic $C_1$-$C_6$ alkyl ester (—C(=O)OR wherein R is $C_1$-$C_{10}$ alkyl), a carboxylic acid salt (—C(=O)OM) wherein M is an organic or inorganic anion, a sulfonic acid (—SO$_3$H$_2$), a sulfonic mono- or dibasic salt (—SO$_3$MH or —SO$_3$M$_2$ wherein M is an organic or inorganic anion), a phosphoric acid (—PO$_3$H$_2$), a phosphoric acid mono- or dibasic salt (—PO$_3$MH or —PO$_3$M2 wherein M is an organic or inorganic anion), a $C_1$-$C_{12}$ alkyl, a $C_3$-$C_{12}$ cycloalkyl, a $C_2$-$C_{12}$ alkenyl, a $C_5$-$C_{12}$ cycloalkenyl, a $C_2$-$C_{12}$ alkynyl, a $C_6$-$C_{12}$ aryl, a $C_7$-$C_{13}$ arylalkylene, a $C_4$-$C_{12}$ heterocycloalkyl, and a $C_3$-$C_{12}$ heteroaryl instead of hydrogen, provided that the substituted atom's normal valence is not exceeded.

"Pharmaceutical composition" means a composition comprising at least one active agent, such as a compound or salt of Formula (I), and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "therapeutically effective amount" of a pharmaceutical composition means an amount effective, when administered to a patient, to provide a therapeutic benefit such as an amelioration of symptoms, decrease disease progression, or cause disease regression.

A "therapeutic compound" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where $p<0.05$.

Chemical Description

Compounds of Formulae I, Ia, Ib, II, III, IV, V, and VI may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Accept-*

*able Salts: Properties, Selection and Use*, P. Heinrich Stahl and Camille G. Wermuth, Editors, Wiley-VCH, 2002.

Embodiments

An aspect of the present invention encompasses a compound having Formula (I) illustrated below and its enantiomer, or a pharmaceutically acceptable solvate or salt thereof:

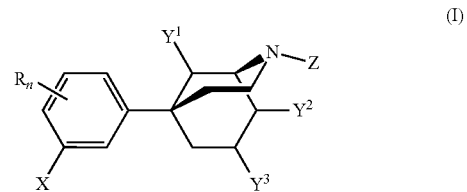

(I)

In Formula (I), X may be —$OR^1$, —$NR^1R^2$, —$CO_2R^1$, —$CONR^1R^2$, or —$(CR^1R^2)_{m1}OH$, wherein each $R^1$ is H, a substituted or unsubstituted $C_1$-$C_{30}$ alkyl, a substituted or unsubstituted $C_3$-$C_{30}$ cycloalkyl, or a substituted or unsubstituted $C_6$-$C_{30}$ aryl, wherein each $R^2$ is H, a substituted or unsubstituted $C_1$-$C_{30}$ alkyl, a substituted or unsubstituted $C_3$-$C_{30}$ cycloalkyl, a substituted or unsubstituted $C_2$-$C_{30}$ alkanoyl, a substituted or unsubstituted $C_4$-$C_{30}$ cycloalkanoyl, or a substituted or unsubstituted $C_6$-$C_{30}$ aryl, and wherein m is an integer of 1 to 10.

In Formula (I), $Y^1$, $Y^2$, and $Y^3$ may each independently be $C_1$-$C_{10}$ alkyl, —$(CR^3R^4)_{m2}V$, provided that at least one selected from $Y^1$, $Y^2$, and $Y^3$ is —$(CR^3R^4)_{m2}V$, —O$(CR^3R^4)_{m2}V$, or —$N(CR^3R^4)_{m2}V$, wherein $R^3$ and $R^4$ are each independently H, a substituted or unsubstituted $C_1$-$C_{30}$ alkyl, a substituted or unsubstituted $C_1$-$C_{30}$ alkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, a substituted or unsubstituted $C_3$-$C_{30}$ cycloalkyl, a substituted or unsubstituted $C_3$-$C_{30}$ cycloalkyl wherein at least one —$CH_2$— is replaced with —$S(=O)_2$—, —$C(=O)$—, —O—, —S—, —$S(=O)$—, —$C(=O)O$—, —$C(=O)$NR'— wherein R' is hydrogen or a C1 to C10 linear or branched alkyl group, —NR'— wherein R' is hydrogen or a C1 to C10 linear or branched alkyl group, a substituted or unsubstituted $C_6$-$C_{30}$ aryl, or a substituted or unsubstituted $C_1$-$C_{30}$ heteroaryl, and wherein m2 is an integer of 1 to 10. V is a functional group, which may be —$COR^5$, —$C(O)$$OR^5$, —$OC(O)OR^5$, —$OR^5$, —$C(O)NR^5R^6$, —$OC(O)$$NR^5R^6$, —$NR^5R^6$, wherein each $R^5$ is H, a substituted or unsubstituted $C_1$-$C_{30}$ alkyl, a substituted or unsubstituted $C_1$-$C_{30}$ alkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, a substituted or unsubstituted $C_3$-$C_{30}$ cycloalkyl, a substituted or unsubstituted $C_3$-$C_{30}$ cycloalkyl wherein at least one —$CH_2$— is replaced with —$S(=O)_2$—, —$C(=O)$—, —O—, —S—, —$S(=O)$—, —$C(=O)O$—, —$C(=O)$NR'— wherein R' is hydrogen or a C1 to C10 linear or branched alkyl group, —NR'— wherein R' is hydrogen or a C1 to C10 linear or branched alkyl group, a substituted or unsubstituted $C_6$-$C_{30}$ aryl, and wherein each $R^6$ is H, a substituted or unsubstituted $C_1$-$C_{30}$ alkyl, a substituted or unsubstituted $C_3$-$C_{30}$ cycloalkyl, a substituted or unsubstituted $C_2$-$C_{30}$ alkanoyl, a substituted or unsubstituted $C_4$-$C_{30}$ cycloalkanoyl, or a substituted or unsubstituted $C_6$-$C_{30}$ aryl.

In Formula (I), Z is H, -L-W, or —$(CR^7R^8)_{m3}$W, wherein L is a substituted or unsubstituted $C_2$-$C_{10}$ alkenylene or a substituted or unsubstituted $C_2$-$C_{10}$ alkynylene, $R^7$ and $R^8$ are each independently H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl, wherein any two selected from $R^7$ and $R^8$ are optionally bonded together to form a ring, W is H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl, and m3 is an integer of 1 to 10.

In Formula (I), R may be halogen or a substituted or unsubstituted $C_1$-$C_{30}$ alkyl, for example, a substituted or unsubstituted $C_1$-$C_{20}$ alkyl, a substituted or unsubstituted $C_1$-$C_{10}$ alkyl, or a substituted or unsubstituted $C_1$-$C_5$ alkyl, and n may be an integer of 1 to 10. For example, R may be H or halogen.

The "enantiomer" of the compound having Formula (I) refers to a compound having Formula (I-ent) illustrated below:

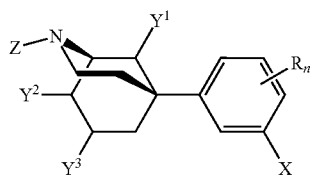
(I-ent)

As one can see, the compound having Formula (I-ent) is a non-superimposable mirror image of the compound having Formula (I).

In an embodiment, the compound having Formula (I) may be represented by Formula (I-1):

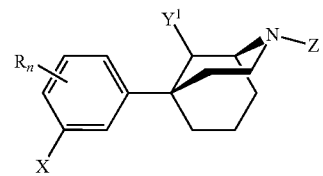
(I-1)

The "enantiomer" of the compound having Formula (I-1) refers to a compound having Formula (I-1-ent) illustrated below:

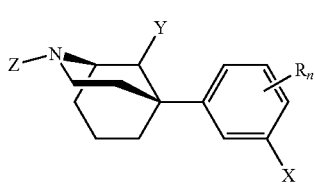
(I-1-ent)

In an embodiment, the compound having Formula (I) may be represented by Formula (Ia):

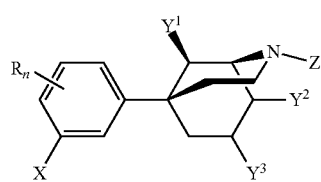
(Ia)

The "enantiomer" of the compound having Formula (Ia) refers to a compound having Formula (Ia-ent) illustrated below:

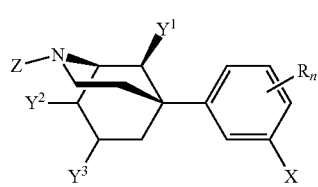
(Ia-ent)

In another embodiment, the compound having Formula (I) may be represented by Formula (Ib):

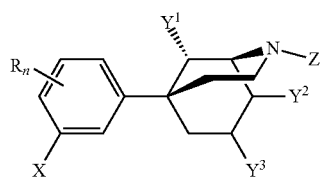
(Ib)

The "enantiomer" of the compound having Formula (Ib) refers to a compound having Formula (Ib-ent) illustrated below:

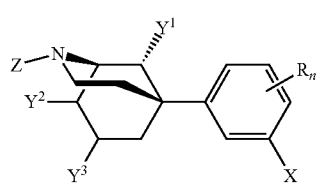
(Ib-ent)

In an embodiment, the compound having Formula (I) may be represented by Formula (Ia-1):

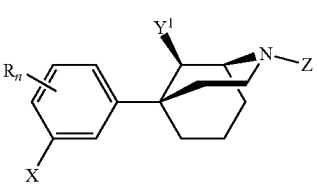
(Ia-1)

The "enantiomer" of the compound having Formula (Ia-1) refers to a compound having Formula (Ia-1-ent) illustrated below:

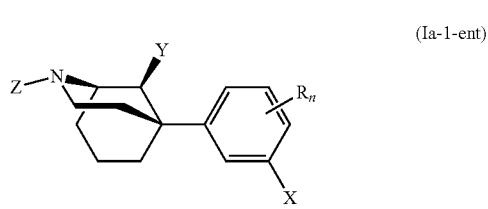
(Ia-1-ent)

In another embodiment, the compound having Formula (I) may be represented by Formula (Ib-1):

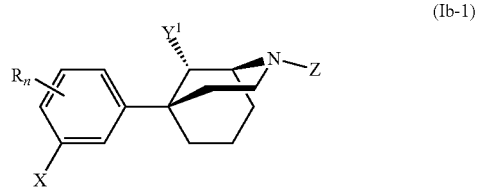
(Ib-1)

The "enantiomer" of the compound having Formula (Ib-1) refers to a compound having Formula (Ib-1-ent) illustrated below:

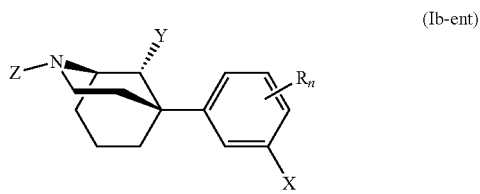
(Ib-ent)

In Formulae (I-1), (I-1-ent), (Ia), (Ia-ent), (Ib), (Ib-ent), (Ia-1), (Ia-1-ent), (Ib-1), and (Ib-1-ent), R, X, $Y^1$, $Y^2$, $Y^3$, Z, and n are the same as in Formula (I).

As noted above, group Z may be —$(CR^7R^8)_{m3}$W, wherein $R^7$, $R^8$, m3, and W are the same as in Formula (I). For example, $R^7$ and $R^8$ may be each H. m3 may be an integer of 1 to 5, for example, 2, 3, or 4. Group W may be a substituted or unsubstituted $C_6$-$C_{30}$ aryl, for example, a substituted or unsubstituted $C_6$-$C_{18}$ aryl, or a substituted or unsubstituted $C_6$-$C_{12}$ aryl.

In an embodiment, Z may be —$CH_2CH_2$W, wherein W may be unsubstituted $C_6$-$C_{30}$ aryl, $C_6$-$C_{30}$ aryl substituted with —F, —Cl, —Br, —OH, —$NH_2$ or —$NO_2$, unsubstituted $C_1$-$C_{30}$ heteroaryl, or $C_1$-$C_{30}$ heteroaryl substituted with —F, —Cl, —Br, —OH, —$NH_2$ or —$NO_2$.

In another embodiment, the compound represented by Formula (I) may be represented by Formula (II):

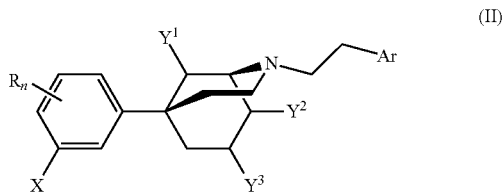
(II)

The "enantiomer" of the compound having Formula (II) refers to a compound having Formula (II-ent) illustrated below:

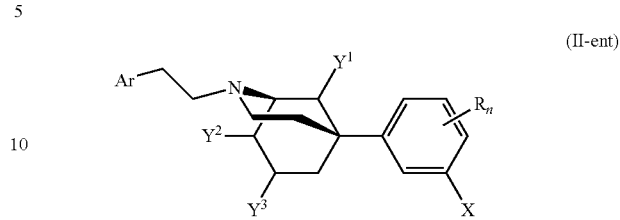
(II-ent)

In Formulae (II) and (II-ent), R, X, $Y^1$, $Y^2$, $Y^3$, and n are the same as in Formula (I), and Ar is a substituted or unsubstituted $C_6$-$C_{30}$ aryl.

In another embodiment, X may be —OH, so the compound represented by Formula (I) may be represented by Formula (III):

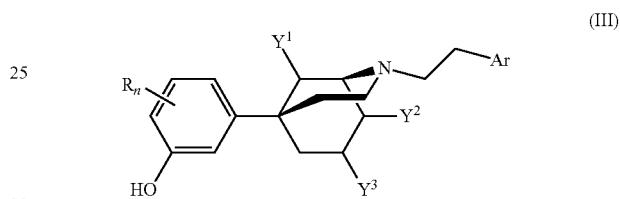
(III)

The "enantiomer" of the compound having Formula (III) refers to a compound having Formula (III-ent) illustrated below:

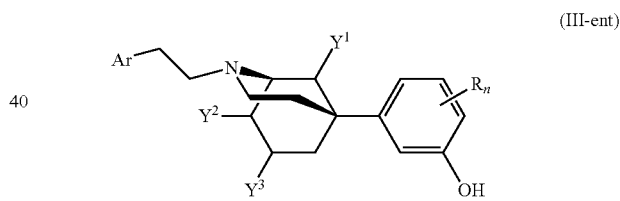
(III-ent)

In Formulae (III) and (III-ent), R, $Y^1$, $Y^2$, $Y^3$, and n are the same as in Formula (I), and Ar is a substituted or unsubstituted $C_6$-$C_{30}$ aryl.

As stated above, $Y^1$, $Y^2$, $Y^3$ are each independently —$(CR^3R^4)_{m2}$V, —$O(CR^3R^4)_{m2}$V, or —$N(CR^3R^4)_{m2}$V, wherein $R^3$ and $R^4$ are each independently H, a substituted or unsubstituted $C_1$-$C_{30}$ alkyl, a substituted or unsubstituted $C_1$-$C_{30}$ alkyl wherein at least one —$CH_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted $C_3$-$C_{30}$ cycloalkyl, a substituted or unsubstituted $C_3$-$C_{30}$ cycloalkyl wherein at least one —$CH_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted $C_6$-$C_{30}$ aryl, or a substituted or unsubstituted $C_1$-$C_{30}$ heteroaryl. In an embodiment, $R^3$ and $R^4$ may each be H. m2 may be an integer of 1 to 5, for example, 2, 3, or 4. V may be —C(O)OR$^5$ or —OR$^5$, wherein R$^5$ is H or a substituted or unsubstituted C$_1$-C$_{30}$ alkyl, for example, a substituted or unsubstituted C$_1$-C$_{20}$ alkyl, a substituted or unsubstituted C$_1$-C$_{10}$ alkyl, or a substituted or unsubstituted C$_1$-C$_5$ alkyl. In an embodiment, R$^5$ may be a substituted or unsubstituted C$_1$-C$_{30}$ alkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, a substituted or unsubstituted C$_3$-C$_{30}$ cycloalkyl, a substituted or unsubstituted C$_3$-C$_{30}$ cycloalkyl wherein at least one —CH$_2$— is replaced with —S(=O)$_2$—, —C(=O)—, —O—, —S—, —S(=O)—, —C(=O)O—, —C(=O)NR'— wherein R' is hydrogen or a C1 to C10 linear or branched alkyl group, —NR'— wherein R' is hydrogen or a C1 to C10 linear or branched alkyl group, or a substituted or unsubstituted C$_6$-C$_{30}$ aryl; and each R$^6$ is H, a substituted or unsubstituted C$_1$-C$_{30}$ alkyl, a substituted or unsubstituted C$_3$-C$_{30}$ cycloalkyl, a substituted or unsubstituted C$_2$-C$_{30}$ alkanoyl, a substituted or unsubstituted C$_4$-C$_{30}$ cycloalkanoyl, or a substituted or unsubstituted C$_6$-C$_{30}$ aryl. In another embodiment, V may be —OH or —CO$_2$CH$_3$.

In another embodiment, X may be —OH, so the compound represented by Formula (I) may be represented by Formula (IV):

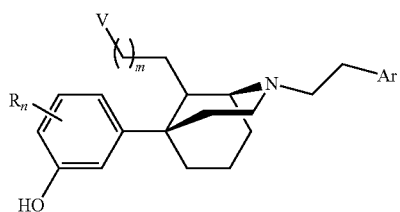

(IV)

The "enantiomer" of the compound having Formula (IV) refers to a compound having Formula (IV-ent) illustrated below:

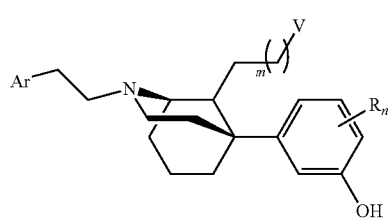

(IV-ent)

In Formulae (IV) and (IV-ent), R, V, and n are the same as in Formula (I), m is an integer of 1 to 10, and Ar is a substituted or unsubstituted C$_6$-C$_{30}$ aryl.

In Formula (IV), V may be —C(O)OR$^5$ and m may be 1. In this embodiment, Formula (IV) may be represented by Formula (V):

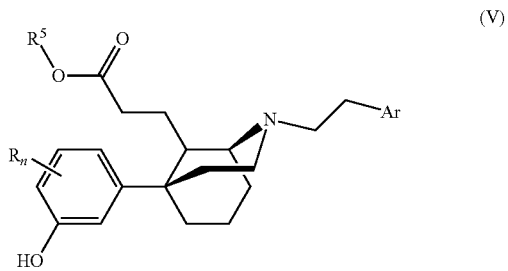

(V)

The "enantiomer" of the compound having Formula (V) refers to a compound having Formula (V-ent) illustrated below:

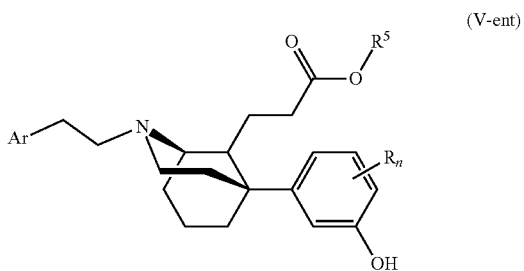

(V-ent)

In Formulae (V) and (V-ent), R and n are the same as in Formula (I), Ar is a substituted or unsubstituted C$_6$-C$_{12}$ aryl, and R$^5$ is a substituted or unsubstituted C$_1$-C$_5$ alkyl.

In Formula (IV), V may also be —OH and m may be 2. In this embodiment, Formula (IV) may be represented by Formula (VI):

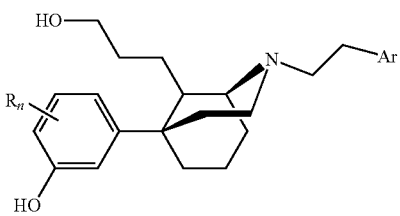

(VI)

The "enantiomer" of the compound having Formula (VI) refers to a compound having Formula (VI-ent) illustrated below:

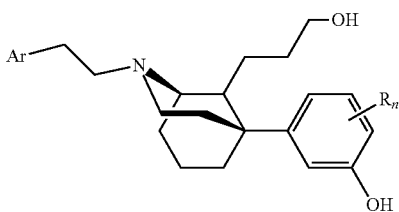

In Formula (VI), R and n are the same as in Formula (I), and Ar is a substituted or unsubstituted C$_6$-C$_{12}$ aryl.

Another aspect of the present invention encompasses a compound having Formulae (VII) or (VIII) illustrated below and their enantiomer, or a pharmaceutically acceptable solvate or salt thereof:

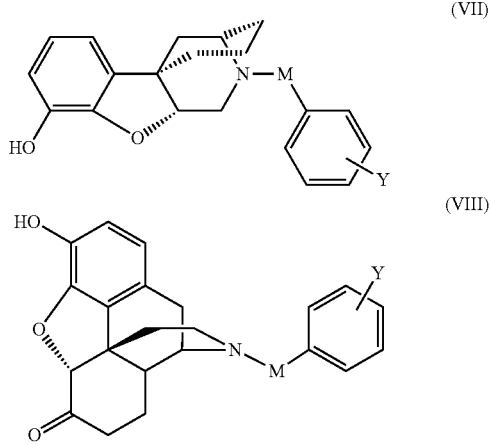

(VII)

(VIII)

In Formulae (VII) and (VIII), M may be a substituted or unsubstituted $C_2$-$C_{10}$ alkenylene, a substituted or unsubstituted $C_2$-$C_{10}$ alkynylene, or —$(CR^7R^8)_{m3}$—, wherein $R^7$ and R may each independently be H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl, wherein any two selected from $R^7$ and $R^8$ may be optionally bonded together to form a ring, and m3 is an integer of 1 to 10.

In Formulae (VII) and (VIII), Y may be —F, Cl, —Br, —I, —OH, —$NO_2$, —CN, —$NR_2$ wherein each R is independently hydrogen or $C_1$-$C_{10}$ alkyl, —C(=O)OH, —C(=O)OR wherein R is $C_1$-$C_{10}$ alkyl, —C(=O)OM wherein M is an organic or inorganic anion, a $C_1$-$C_{12}$ alkyl, a $C_1$-$C_9$ alkoxy, a $C_1$-$C_9$ haloalkoxy, a $C_3$-$C_{12}$ cycloalkyl, a $C_2$-$C_{12}$ alkenyl, a $C_5$-$C_{12}$ cycloalkenyl, a $C_2$-$C_{12}$ alkynyl, a $C_6$-$C_{12}$ aryl, a $C_7$-$C_{13}$ arylalkylene, a $C_4$-$C_{12}$ heterocycloalkyl, and a $C_3$-$C_{12}$ heteroaryl.

The "enantiomer" of the compound having Formulae (VII) or (VIII) refers to a compound having Formulae (VII-ent) or (VIII-ent) illustrated below:

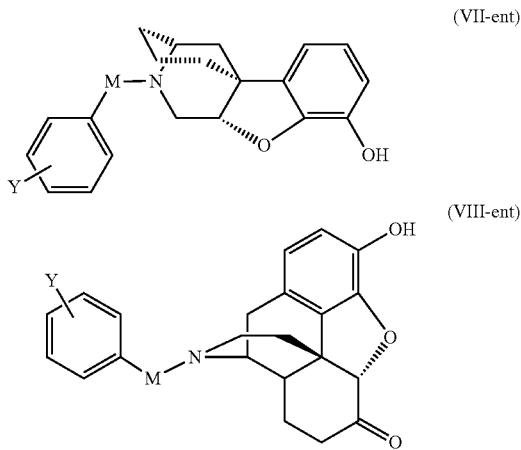

(VII-ent)

(VIII-ent)

In Formulae (VII-ent) and (VIII-ent), M and Y are the same as in Formulae (VII) and (VIII).

The compounds of the present invention may be used in methods to bind opioid receptors, including μ, κ and δ opioid receptors. Such binding may be accomplished by contacting the receptor with an effective amount of the compound of the invention. Preferably, the contacting step conducted in an aqueous medium, preferably at physiologically relevant ionic strength, pH, and the like.

In some embodiments of the invention, the compounds agonize the activity of the opioid receptors. In other embodiments, the compounds prevent or treat a condition or disease caused by an opioid (either endogenous or exogenous). In certain embodiments, particularly where the opioid are exogenous, the compounds of the invention preferably do not substantially cross the blood-brain barrier.

The compounds of the present invention may be used in methods to agonize μ, κ, or δ or any combinations or subcombinations of those opioid receptors, particularly where undesirable symptoms or conditions are side effects of administering exogenous opioids. As explained below, the compounds of the invention may be used as to treat patients having disease states that are ameliorated by binding opioid receptors or in any treatment wherein temporary suppression of the μ, κ or both types of opioid receptor system is desired.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 3d. Ed., Wiley & Sons, 1991.

Pharmaceutical Preparations

Reference to a formula includes references to all subformulae, for example, Formula (I) includes compounds of Formula (Ia), (Ib), (Ia-1), (Ib-1), (II), (III), (IV), (V), (VI), (VII), and (VIII). Compounds disclosed herein can be administered as the neat chemical, but are preferably administered as a pharmaceutical composition. Accordingly, the invention encompasses pharmaceutical compositions comprising a therapeutically effective amount of a compound or pharmaceutically acceptable salt of a compound, such as the compound of Formula (I), the compound of Formula (VII), or the compound of Formula (VIII), together with at least one pharmaceutically acceptable carrier. The pharmaceutical composition may contain a therapeutically effective amount of the compound or salt of Formula (I), Formula (VII), or Formula (VIII), as the only active agent, but is preferably contains at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula (I), a compound of Formula (VII), or a compound of Formula (VIII), and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound, such as a compound of Formula (I), a compound of Formula (VII), or a compound of Formula (VIII), and an additional active agent. For example the pharmaceutical composition may contain a molar ratio of about 0.5:1, about 1:1, about 2:1, about 3:1 or from about 1.5:1 to about 4:1 of an additional active agent to a compound of Formula (I), a compound of Formula (VII), or a compound of Formula (VIII).

The pharmaceutical composition may further include a therapeutically effective amount of an opioid. The opioid may be selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, or a combination thereof.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., a therapeutically effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt %) of a compound of Formula (I), a compound of Formula (VII), or a compound of Formula (VIII), and usually at least about 5 wt. % of a compound of Formula (I), a compound of Formula (VII), or a compound of Formula (VIII). Some embodiments contain from about 25 wt % to about 50 wt % or from about 5 wt % to about 75 wt % of the compound of Formula (I), the compound of Formula (VII), or the compound of Formula (VIII).

Treatment Methods

The compounds of Formula (I), Formula (VII), and Formula (VIII), as well as pharmaceutical compositions comprising the compounds, are useful for treatment of pain. According to the present invention, a method of treating pain comprises providing to a patient in need of such treatment a therapeutically effective amount of a compound of Formula (I), a compound of Formula (VII), or a compound of Formula (VIII). In an embodiment, the patient is a mammal, and more specifically, a human. As will be understood by one skilled in the art, the invention also encompasses methods of treating non-human patients such as companion animals, e.g., cats, dogs, and livestock animals.

A therapeutically effective amount of a pharmaceutical composition is preferably an amount sufficient to reduce or ameliorate the symptoms of a disease or condition. For example, a therapeutically effective amount may be an amount sufficient to reduce or ameliorate acute or chronic pain. A therapeutically effective amount of a compound or pharmaceutical composition described herein will also provide a sufficient concentration of a compound of Formula (I), a compound of Formula (VII), or a compound of Formula (VIII), when administered to a patient. A sufficient concentration is preferably a concentration of the compound in the patient's body necessary to prevent or combat the feeling of pain. Such an amount may be ascertained experimentally, for example by assaying blood concentration of the compound, or theoretically, by calculating bioavailability.

According to the invention, the methods of treatment disclosed herein include providing certain dosage amounts of a compound of Formula (I), a compound of Formula (VII), or a compound of Formula (VIII) to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula (I), a compound of Formula (VII), or a compound of Formula (VIII) are provided daily to a patient. Frequency of dosage may also vary depending on the compound used and the particular degree of pain. However, for most treatments, a dosage regimen of 4 times daily or less can be used, and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination, and the severity of the particular disease undergoing therapy.

A compound of Formula (I), a compound of Formula (VII), or a compound of Formula (VIII) may be administered singularly (i.e., sole therapeutic agent of a regime) to treat or prevent pain, or may be administered in combination with another active agent. One or more compounds of Formula (I), Formula (VII), or Formula (VIII) may be administered in coordination with a regime of one or more opioid-like analgesics. In an embodiment, a method of treating pain in a mammal includes administering to said mammal a therapeutically effective amount of a compound of Formula (I), a compound of Formula (VII), or a compound of Formula (VIII), optionally, in combination with one or more additional active ingredients.

As will be appreciated by one skilled in the art, the methods of treatment provided herein are also useful for treatment of mammals other than humans, including for veterinary applications such as to treat horses and livestock, e.g., cattle, sheep, cows, goats, swine and the like, and pets (companion animals) such as dogs and cats.

For diagnostic or research applications, a wide variety of mammals will be suitable subjects including rodents (e.g., mice, rats, hamsters), rabbits, primates, and swine such as inbred pigs and the like. Additionally, for in vitro applications, such as in vitro diagnostic and research applications, body fluids (e.g., blood, plasma, serum, cellular interstitial fluid, saliva, feces, and urine) and cell and tissue samples of the above subjects will be suitable for use.

In an embodiment, the invention provides a method of treating pain in a patient identified as in need of such treatment, the method comprising providing to the patient a therapeutically effective amount of a compound of Formula (I). The compounds of Formula (I) provided herein may be administered alone, or in combination with one or more other active agents.

In another embodiment, the method of treating pain may additionally include administering the compound of Formula (I), the compound of Formula (VII), or the compound of Formula (VIII), in combination with one or more additional compounds, wherein at least one of the additional compounds is an active agent, to a patient in need of such treatment. The one or more additional compounds may include additional therapeutic compounds, including an opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, or a combination thereof.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

The opioid component of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference*, 1999, the disclosure of which is hereby incorporated herein by reference, in its entirety.

The compounds employed in the methods of the present invention may exist in prodrug form. As used herein, "prodrug" is intended to include any covalently bonded carriers which release the active parent drug, for example, as according to Formula (I), Formula (VII), or Formula (VIII), or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example, Formula (I), Formula (VII), or Formula (VIII), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, iso-butyl, sec-butyl, tert-butyl, cyclopropyl, phenyl, benzyl, and phenethyl esters, and the like.

While not intending to be bound by any theory or theories of operation, it is contemplated that opioid side effects, such as constipation, vomiting and nausea, may result from undesirable interaction of the opioid with peripheral opioid receptors, such as peripheral receptors. Administration of the compounds of Formula (I), the compound of Formula (VII), or the compound of Formula (VIII), according to one aspect of the present invention may block interaction of the opioid compounds with the peripheral receptors, thereby preventing and/or inhibiting the side effects, while preferably not interfering with the therapeutic effect of the opioid in the CNS.

The compounds of the present invention may be used in methods to agonize μ, κ, or δ or any combinations or subcombinations of those opioid receptors, particularly where undesirable symptoms or conditions are side effects of administering exogenous opioids. Furthermore, the compounds of the invention may be used as to treat patients having disease states that are ameliorated by binding opioid receptors or in any treatment wherein temporary suppression of the μ, κ or both types of opioid receptor system is desired.

Such symptoms, conditions or diseases include the complete or partial agonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); prevention of sudden infant death syndrome; treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the invention present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

In certain embodiments, the compounds of the invention may be used in methods for preventing or treating postoperative or opioid-induced ileus.

EXAMPLES

The present invention is further described in detail by means of the following Examples. All parts and percentages are by weight and all temperatures are degrees Celsius unless explicitly stated otherwise.

Melting points were determined on a Mettler Toledo MP70 and are uncorrected. Proton and carbon nuclear magnetic resonance ($^1$H and $^{13}$C NMR) spectra were recorded on a Varian Gemini-400 spectrometer in CDCl$_3$ (unless otherwise noted) with the values given in ppm (TMS as internal standard) and J (Hz) assignments of H resonance coupling. Mass spectra (HRMS) were recorded on a VG 7070E spectrometer or a JEOL SX102a mass spectrometer. The optical rotation data were obtained on a PerkinElmer polarimeter model 341. Thin layer chromatography (TLC) analyses were carried out on Analtech silica gel GHLF 0.25 mm plates using various gradients of CHCl$_3$/MeOH containing 1% NH$_4$OH or gradients of EtOAc/n-hexane. Visualization was accomplished under UV light or by staining in an iodine chamber. Flash column chromatography was performed with Fluka silica gel 60 (mesh 220-400). Robertson Microlit Laboratories, Ledgewood, N.J., performed elemental analyses, and the results were within ±0.4% of the theoretical values.

Exemplary compounds 8 and 9 were prepared according to a synthetic scheme shown in FIG. 1. The synthetic procedures for preparing compounds 8 and 9 are described below.

5-(3-Methoxyphenyl)-2-methyl-2-azabicyclo[3.3.1]nonane-9-carbaldehyde (3). A 100 mL round-bottomed flask was charged with (methoxymethyl)triphenylphosphonium chloride (51.42 g, 150 mmol), evacuated, backfilled with Ar, and charged with THF (125 mL). Potassium tert-butoxide (16.8 g, 150 mmol) was added in one portion, and the deep red solution was stirred for 30 min. The l-tartrate salt of 1 (20.46 g, 50 mmol, prepared according to the procedure reported by Hiebel et al. in *Journal of Medicinal Chemistry*, 2007, 50, 3765-3776; hereinafter "Reference 1") was free based in water (300 mL) with saturated aqueous NH$_4$OH (18 mL) extracted with toluene (3×200 mL), dried over MgSO$_4$, filtered, and concentrated under reduced pressure. The residue was added to the reaction flask via syringe, rinsing with dry THF (25 mL), and the mixture stirred for 16 h at room temperature. The bulk of the THF was removed under vacuum. The residue was taken up in EtOAc (200 mL) and washed with 1 N aqueous HCl (3×100 mL). The combined aqueous layers were washed an additional time with EtOAc (1×100 mL) and then made basic by the addition of saturated aqueous NH$_4$OH (25 mL). The aqueous layer was extracted with DCM (3×250 mL), dried over MgSO$_4$, filtered, and concentrated under vacuum. The residue was purified via flash chromatography eluting with CHCl$_3$/MeOH/NH$_4$OH (99:0.9:0.1 to 80:20:2) to afford methyl vinyl ether intermediate 2 as a green oil. This material was immediately taken up in 3 N aqueous HCl (180 mL) and stirred under argon for 24 h at room temperature. The reaction was cooled to 0° C., quenched with aqueous saturated NH$_4$OH (50 mL), and extracted with CHCl$_3$ (3×150 mL). The combined organic layers were dried over MgSO$_4$, filtered, and concentrated under vacuum. The residue was purified via flash chromatography eluting with CHCl$_3$/MeOH/NH$_4$OH (99:0.9:0.1 to 80:20:2) to afford aldehyde 3 as a green oil (6.57 g, 48%) and as a 2:1 mixture of diasteromers. Less polar, major diastereomer: R$_f$=0.47 (95:4.5:0.5 CHCl$_3$:MeOH:sat. aq. NH$_4$OH) $^1$H-NMR (400 MHz; CDCl$_3$): δ 9.69 (s, 1H), 7.23 (d, J=7.9 Hz, 1H), 6.88-6.84 (m, 2H), 6.74 (d, J=8.4 Hz, 1H), 3.79 (s, 3H), 3.41 (s, 1H), 3.15 (td, J=12.0, 5.4 Hz, 1H), 2.91 (dd, J=11.7, 8.2 Hz, 1H), 2.79 (s, 1H), 2.61 (td, J=12.6, 8.1 Hz, 1H), 2.37 (s, 3H), 2.31 (td, J=12.8, 5.1 Hz, 2H), 2.05-1.93 (m, 1H), 1.85 (dd, J=12.6, 5.9 Hz, 1H), 1.72-1.63 (m, 2H), 1.54-1.41 (m, 1H). HRMS-ESI (m/z): [M+H]$^+$ calcd for C$_{17}$H$_{24}$NO$_2$ 274.1807, found 274.1811.

Methyl (E)-3-((1S,5R,9R)-5-(3-methoxyphenyl)-2-methyl-2-azabicyclo[3.3.1]nonan-9-yl)acrylate (4β). A single-neck 500 mL round-bottomed flask was charged with 60% NaH dispersion in mineral oil (4.81 g, 120.2 1 mmol) followed by dry THF (300 mL). Triethylphosphonoacetate (23.8 mL, 120.1 mmol) was added dropwise over 10 min, and stirred for 30 min to afford a clear solution. A solution of 3 as a 1:2 mixture of diastereomers (6.57 g, 24.0 mmol) was taken up in THF (20 mL) and added dropwise to the reaction mixture. The reaction was allowed to stir under argon for 22 h at room temperature. The bulk of the THF was removed under vacuum, and the residue was taken up in $Et_2O$ (100 mL) and 2N aqueous HCl (100 mL). The organic layer was separated, and the aqueous phase was basified by the addition of aqueous saturated $NH_4OH$. The aqueous phase was extracted with $CHCl_3$ (3×100 mL), dried over $MgSO_4$, filtered, and concentrated under vacuum. The residue was taken up in $Et_2O$ (50 mL) and 4 N aqueous NaOH (50 mL) and stirred for 12 h under argon at room temperature. The organic layer was separated and the aqueous layer was extracted with $Et_2O$ (3×50 mL). The combined organic layers were washed with 2 N aqueous HCl (1×150 mL). The acidic aqueous layer was extracted with $Et_2O$ (3×150 mL) and then basified by the addition of saturated aqueous $NH_4OH$. The alkaline aqueous layer was extracted with $CHCl_3$ (3×100 mL), dried over $MgSO_4$, filtered, and concentrated under vacuum. The residue was purified via flash chromatography eluting with $CHCl_3$/MeOH/saturated aqueous $NH_4OH$ (99:0.9:0.1 isocratic) to afford enone 4 as a 1:3 mixture of diastereomers favoring the less polar R isomer. The less polar β isomer (4.46 g, 13.0 mmol, 54%) was isolated as a green oil. $R_f$=0.55 (95:4.5:0.5 $CHCl_3$:MeOH: sat. aq. $NH_4OH$).

Methyl (E)-3-5-(3-methoxyphenyl)-2-azabicyclo[3.3.1]nonan-9-yl)acrylate (5). A single-neck 100 mL round-bottomed flask was charged with enone 4 (2.85 g, 8.3 mmol), DCE (21 mL), 1-chloroethyl chloroformate (5.35 mL, 49.8 mmol), and $NaHCO_3$ (4.88 g, 58.1 mmol). The resulting mixture was refluxed for 22 h under argon. The reaction mixture was cooled to room temperature and filtered through a sintered glass filter. The reaction flask was washed with $CHCl_3$ (3×10 mL) and the washings were used to rinse the solids remaining on top of the filter. The filtrate was concentrated under vacuum and taken up in MeOH (165 mL) and refluxed under argon for 5 h. The reaction mixture was allowed to cool to room temperature and concentrated under vacuum. The residue was purified via flash chromatography eluting with $CHCl_3$/MeOH/$NH_4OH$ (99:0.9:0.1 to 80:18:2) to afford the mixture of N-nor phenylmorphans 5 (2.14 g, 6.5 mmol, 78%).

Methyl (E)-3-((1S,5R,9R)-5-(3-methoxyphenyl)-2-phenethyl-2-azabicyclo[3.3.1]nonan-9-yl)acrylate (6). A single-neck 200 mL round-bottomed flask was charged with a mixture N-nor phenylmorphans 5 (2.14 g, 6.51 mmol) from the previous step, $K_2CO_3$ (1.80 g, 13.03 mmol), phenethyl bromide (1.33 mL, 9.77 mmol), and MeCN (65 mL). The reaction flask was fitted with a reflux condenser, and the reaction was heated to reflux for 12 h under argon. The reaction was cooled to room temperature and the bulk of the MeCN was removed under vacuum. The residue was taken up in deionized $H_2O$ and extracted with $CHCl_3$ (3×50 mL). The combined organic layers were washed with brine (1×150 mL), dried over $Na_2SO_4$, decanted, and concentrated under vacuum. The residue was purified via flash chromatography eluting with EtOAc/hexanes (1:9 to 1:1) to afford a mixture of phenylmorphans 6 (1.97 g, 4.6 mmol, 71%) as an amber oil.

Methyl 3-(5-(3-methoxyphenyl)-2-azabicyclo[3.3.1]nonan-9-yl)propanoate (7). A mixture of phenylmorphans 6 (1.97 g, 4.6 mmol) from the previous step was dissolved in EtOH (46 mL) and transferred to a 250 mL pressure tested reaction bottle. The vessel was charged with aqueous AcOH (0.26 mL, 4.56 mmol) and Escat 103 5% Pd/C (0.20 g, 10% w/w of the 6 mixture). The vessel was pressurized to 50 psi $H_2$ in a Parr shaker and shaken for 12 at room temperature. The reaction mixture was filtered through Celite, and concentrated under vacuum to afford a yellow oil. The residue was purified via flash chromatography eluting with $CHCl_3$/MeOH/$NH_4OH$ (99:0.9:0.1 isocratic) to afford a mixture of phenylmorphans 7 (1.80 g, 4.6 mmol, 91%) as an amber oil.

Methyl 3-((1S,5R,9R)-5-(3-hydroxyphenyl)-2-phenethyl-2-azabicyclo[3.3.1]nonan-9-yl)propanoate (8). A 200 mL round-bottomed flask was charged with a mixture of phenylmorphans 7 (1.243 g, 2.86 mmol) from the previous step and 48% aqueous HBr (57 mL). A small amount of MeOH (7 mL) was added to the reaction to help solubilize the phenylmorphans. The reaction flask was equipped with a reflux condenser and refluxed under argon for 12 h. The reaction was cooled to room temperature and the reflux condenser was removed and replaced with a short-path distillation head. The bulk of the 48% aqueous HBr was removed by vacuum distillation (40 mbar, 90° C.) to afford a yellow oil. The oil was taken up in MeOH (57 mL), and the flask was charged with trimethyl orthoformate (0.94 mL, 8.57 mmol) and a catalytic amount of $H_2SO_4$ (0.2 mL). The reaction flask was equipped with a reflux condenser and heated to reflux under argon for 2.5 h. The reaction mixture was cooled to 0° C. and quenched by the addition of 7 N methanolic ammonia (0.8 mL). The crude reaction mixture was concentrated in vacuo and purified via flash chromatography eluting with $CHCl_3$/MeOH/$NH_4OH$ (99:0.9:0.1 to 80:18:2) to afford 8 as a yellow oil (76%, 0.881 g, 216 mmol). $R_f$=0.78 (85:13.5:1.5 $CHCl_3$:MeOH:sat. aq. $NH_4OH$). $^1$H-NMR (400 MHz; DMSO-$d_6$): δ 9.17 (s, 1H), 7.26-7.17 (m, 4H), 7.17-7.10 (m, 1H), 7.08 (t, J=7.9 Hz, 1H), 6.72 (d, J=7.8 Hz, 1H), 6.68 (s, 1H), 6.54 (d, J=8.3 Hz, 1H), 3.54-3.47 (m, 3H), 3.00 (d, J=8.4 Hz, 2H), 2.82 (s, 1H), 2.79-2.64 (m, 4H), 2.22 (d, J=12.7 Hz, 1H), 2.17-1.98 (m, 2H), 1.99-1.80 (m, 4H), 1.80-1.65 (m, 3H), 1.65-1.52 (m, 2H), 1.45-1.29 (m, 1H), 1.01 (q, J=8.5 Hz, 1H), 1.06-0.95 (m, 1H). $^{13}$C NMR (101 MHz; DMSO-$d_6$): δ 173.4, 157.0, 151.5, 140.6, 128.8, 128.5, 127.9, 125.4, 115.8, 112.26, 112.07, 56.2, 52.2, 50.9, 48.3, 43.9, 42.3, 38.4, 33.4, 31.4, 29.2, 25.6, 22.8, 21.7. HRMS-ESI (m/z): [M+H]$^+$ cald for $C_{26}H_{34}NO_3$ 408.2539, found 408.2546. The free base was converted into its HCl salt for analysis. Anal. Calcd for $C_{26}H_{34}ClNO_3 \cdot 0.25H_2O$ C, 69.63%; H, 7.75%; N, 3.12%. Found C, 69.95%, H, 7.54%, N, 3.10%.

3-((1S,5R,9R)-9-(2-hydroxyethyl)-2-phenethyl-2-azabicyclo[3.3.1]nonan-5-yl)phenol (9). A 50 mL single-neck round-bottomed flask was charged with 8 (0.542 g, 1.33 mmol) and THF (27 mL). The flask was cooled to 0° C. and $LiAlH_4$ (2.66 mL, 2.66 mmol, 1 M in THF) was added dropwise via syringe. The flask stirred for 30 min gradually warming to room temperature. The flask was equipped with a reflux condenser, and the reaction was heated to reflux for 20 h under argon. The reaction was cooled to 0° C. and quenched by the drop-wise addition of 2 M aqueous Rochelle salt (25 mL). The crude reaction mixture was stirred for 4 h affording a cloudy 2 phase mixture. The less dense THF layer was separated and the aqueous layer was basified to pH 9 with saturated aqueous $NH_4OH$. The aqueous layer was extracted with $CHCl_3$ (3×25 mL) and the combined organic layers including the previously separated THF layer were combined and dried over $MgSO_4$, filtered, and concentrated under vacuum. The resulting residue was purified via flash chromatography eluting with $CHCl_3$/MeOH/$NH_4OH$ (99:0.9:0.1 to 80:18:2) to afford 9 (0.220 g, 0.58 mmol, 44%) as a yellow foam. $R_f$=0.41 (90:0.9:0.1 CHCl$_3$:MeOH:sat. aq. NH$_4$OH). H NMR (400 MHz; DMSO-d$_6$): δ 9.14 (s, 1H), 7.27-7.20 (m, 4H), 7.20-7.12 (m, 1H), 7.06 (t, J=7.9 Hz, 1H), 6.72 (d, J=8.1 Hz, 1H), 6.68 (s, 1H), 6.53 (d, J=8.1 Hz, 1H), 4.18 (t, J=4.9 Hz, 1H), 3.20-3.08 (m, 2H), 3.04-2.94 (m, 2H), 2.91 (s, 1H), 2.80-2.64 (m, 4H), 2.24 (d, J=14.5 Hz, 1H), 2.09 (q, J=11.1 Hz, 1H), 1.94-1.77 (m, 3H), 1.78-1.66 (m, 1H), 1.66-1.54 (m, 2H), 1.54-1.25 (m, 3H), 1.22-1.05 (m, 1H), 0.85-0.63 (m, 1H). $^{13}$C NMR (101 MHz; DMSO-d$_6$): δ 157.5, 152.4, 141.2, 129.3, 129.0, 128.5, 126.1, 116.3, 112.8, 112.5, 61.7, 56.8, 52.9, 49.0, 45.4, 42.7, 39.1, 34.0, 31.6, 29.8, 26.3, 23.5, 23.1. HRMS-ESI (m/z): [M+H]$^+$ calcd. for C$_{25}$H$_{34}$NO$_2$ 380.2590, found 380.2592. The free base was converted to the HBr salt for analysis. mp: 259-262° C. Anal. Calcd. For C$_{25}$H$_{34}$BrNO$_2$.0.05H$_2$O C, 65.09%; H, 7.45; N, 3.04%. Found C, 65.09%; H, 7.27%; N, 3.00%.

The results of in vitro testing of Compounds 8 and 9 are shown in Table 1 below (binding constant $K_i$, nM).

Figure 3:
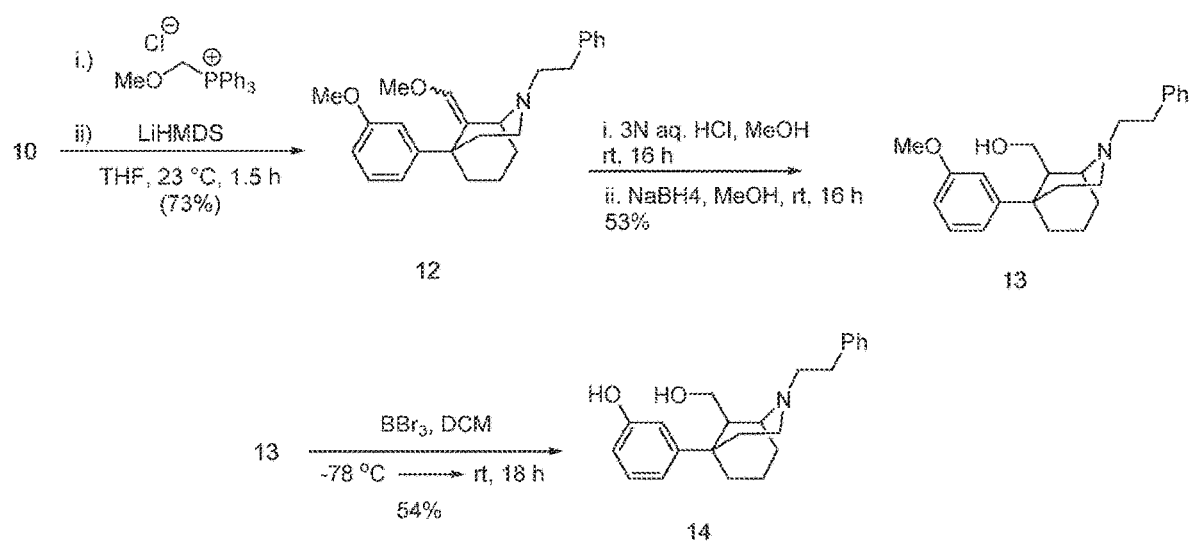
FIG. 3 shows a synthesis of exemplary compound 14.

Exemplary compound 12 was prepared according to a synthetic scheme shown in FIG. 3. The synthetic procedures for preparing compound 12 are described in FIG. 3.

3-(9-(Methoxymethylene)-2-phenethyl-2-azabicyclo [3.3.1]nonan-5-yl)phenol (12). A 25 mL flame-dried round-bottomed flask was equipped with a magnetic stir bar and charged with methoxymethyltriphenylphosphonium chloride (4.789 g, 13.97 mmol) and phenylmorphan 11 (1.69 g, 4.66 mmol) The flask was cooled to 0° C. in an ice/water bath and charged with 1 M LiHMDS solution in THF (18.64 mL, 18.64 mmol) dropwise over 15 min. The color of the reaction changed from white to deep red over the course of the LiHMDS addition. The reaction was stirred for 1.5 h under argon and allowed to gradually warm to room temperature. The reaction mixture was cooled to 0° C. and quenched with MeOH (8 mL) and stirred for 10 min. The bulk of the solvent was stripped off via rotary evacuator (bath temp 40° C.), and the residue was taken up in H$_2$O (15 mL) and CHCl$_3$ (15 mL). The pH of the aqueous layer was

TABLE 1

| Compound# | 3H DAMGO μ | 3H DADLE δ | 3H U69,593 κ | MOR cAMP Agonist Potency ± SEM (nM) (% Efficacy) | MOR Mediated β-arrestin Recruitment (% Control, Emax DAMGO), nM | MOR cAMP Antagonist Potency KB ± SEM (nM) | KOR cAMP Agonist Potency ± SEM (nM) | KOR cAMP AntagonistPotency ± SEM (nM) | DOR cAMP Agonist Potency ± SEM (nM) (% Efficacy) |
|---|---|---|---|---|---|---|---|---|---|
| 8 | 0.90 ± 0.04 | 118 ± 7.41 | 23.2 ± 3.11 | 0.31 ± 0.04 (ca 100%) | >25000 $^a$ | NA | >10000 | 2.0 ± 0.4 | NA |
| 9 | 5.43 ± 0.09 | I | I | 4.7 ± 0.5 (64 ± 2%) | >25000 $^a$ | NA | NA | NA | NA |
| Morphine | 3.26 ± 0.39 | I | I | 2.22 ± 0.01 (ca 100%) | 160 ± 20 (32 ± 3%) | NA | NA | NA | NA |

Binding assays were carried out in triplicate using rat tissue; K$_i$ ± SEM (nM).
I = <50% activity at 100 nM concentration (displaced less than half of radioligand) in exploratory assay.
cAMP studies were carried out by Dr. Prisinzano & Dr. Rachel Saylor Crowley, University of Kansas. Where % efficacy is not listed, the efficacy was 100% for the active compounds and 0% for the inactive compounds.
$^a$ EMax = 0%;
NA = assay not run, insufficient activity.

The MOR Mediated beta-arrestin Recruitment column contains the important difference between morphine and Compounds 8 and 9. Morphine recruits beta-arrestin, while Compounds 8 and 9 do not. Current theory holds that analgesics which do not recruit beta-arrestin will have fewer or no side-effects attributed to normal opioids (respiratory depression, constipation, tolerance, dependence, etc.). There are only two other compounds that are reportedly lack beta-arrestin recruitment and are biased towards the G-protein, "TRV130" and "PZM21". It has been noted that "TRV130" does recruit beta-arrestin slightly, and that "PZM21" may not be a particularly effective analgesic. The present in vitro data suggests that Compound 8 is a full agonist, and a very potent compound that acts via the mu-receptor. It is also a kappa-receptor antagonist, and that may be helpful. Compound 9 is a less potent partial agonist and does not interact with the kappa-receptor. Neither of them recruit beta-arrestin at all; as both compounds are fully biased towards the G-protein.

Exemplary compound 10 was prepared according to a synthetic scheme shown in FIG. 2. The synthetic procedures for preparing compound 10 are described in "Probes for Narcotic Receptor Mediated Phenomena. 34. Synthesis and Structure-Activity Relationships of a Potent mu-Agonist δ-Antagonist and an Exceedingly Potent Antinociceptive in the Enantiomeric C9-Substituted 5-(3-Hydroxyphenyl)-N-phenylethylmorphan Series", J. Med. Chem. 2007, 50, 3765-3776.

adjusted to ~9 (litmus) with aqueous saturated NH$_4$Cl. The aqueous phase was extracted with 9:1 CHCl$_3$/MeOH (3×15 mL) and the combined organic layers were dried over MgSO$_4$, filtered, and concentrated under vacuum. The resulting residue was purified via flash chromatography eluting with CHCl$_3$/MeOH/sat. aq. NH$_4$OH (99:0.9:0.1 to 95:4.5:0.5) to afford methyl vinyl ether 12 (1.26 g, 3.45 mmol, 74%) as tan foam. $R_f$=0.54 (90:10:1 CHCl$_3$:MeOH: sat. aq. NH$_4$OH). $^1$H-NMR (400 MHz; CDCl$_3$+MeOD): δ 7.22 (s, 6H), 7.11 (t, J=7.9 Hz, 1H), 6.95 (d, J=7.7 Hz, 1H), 6.86 (s, 1H), 6.64 (d, J=7.8 Hz, 1H), 5.83 (s, 1H), 3.18 (s, 1H), 3.08 (s, 3H), 2.93-2.74 (m, 5H), 2.35 (dt, J=13.6, 6.8 Hz, 1H), 2.13-2.05 (m, 3H), 2.05-1.96 (m, 1H), 1.91-1.88 (m, 1H), 1.76 (d, J=13.8 Hz, 1H), 1.51-1.47 (m, 1H); $^{13}$C-NMR (101 MHz; CDCl$_3$): $^{13}$C NMR (101 MHz; CDCl$_3$+MeOD): δ 155.2, 151.9, 140.4, 139.7, 128.7, 128.4, 127.9, 126.0, 120.3, 118.5, 114.3, 112.4, 60.5, 59.0, 58.6, 49.1, 41.1, 38.9, 37.7, 34.3, 31.2, 21.2; HRMS-ESI (m/z): [M+H]+ calcd. for C$_{24}$H$_{30}$NO$_2$ 364.2277, found 364.2277.

Figure 4:
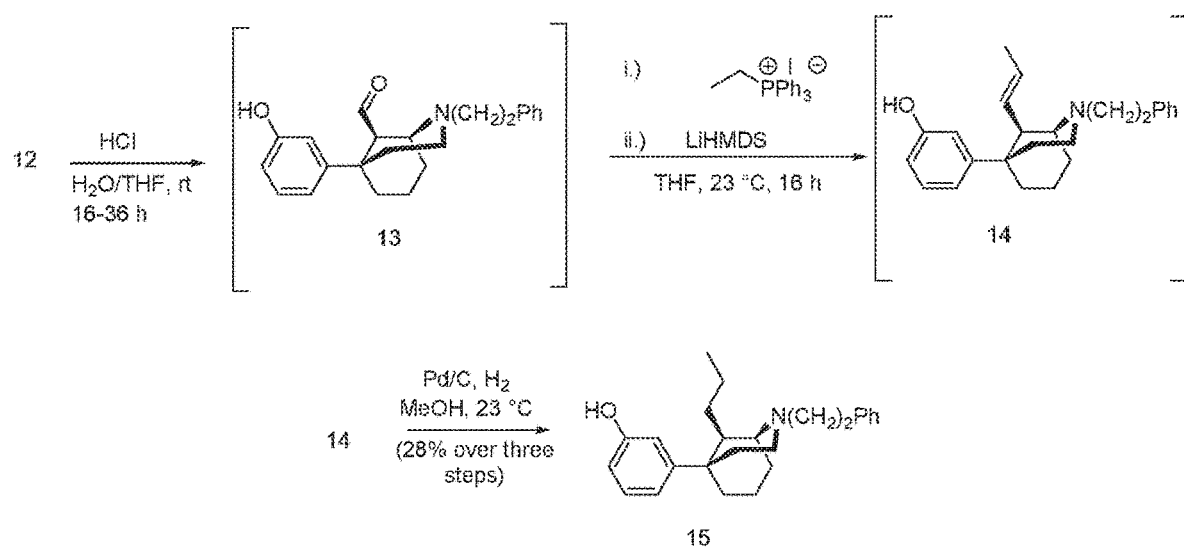
FIG. 4 shows a synthesis of exemplary compound 15.

Exemplary compound 15 was prepared according to a synthetic scheme shown in FIG. 4. The synthetic procedures for preparing compound 15 are described in FIG. 4.

3-(9-(Hydroxymethyl)-2-phenethyl-2-azabicyclo[3.3.1] nonan-5-yl)phenol (14). Hydrolysis of (Z)-12 or (E)-12 in (9:1) 3N aqueous HCl/THF provides the C-9 formyl phenylmorphan as a mixture of epimers. THF is used a cosolvent to improve the solubility of the protonated phenylmorphans. When a 1:1 ratio of 3N aqueous HCl/THF was used, the hydrolysis slowed down significantly resulting in epimerization of the product aldehydes. Isomerization of the more polar (E)-6 isomer to the less polar (Z)-6 isomer was observed when a pure sample (E)-6 was subjected to hydrolysis in (9:1) 3N aqueous HCl/THF. The diastereoselectivity of protonation at C-9 is poor compared to the hydrolysis of N-methyl analogs; dr has ranged from 1:1 to 3:1 favoring beta. The poor selectivity likely stems from the prolonged reaction times required for full conversion of starting material to product.

The intermediate aldehydes are not stable to air or silica and should be used immediately after workup. These aldehydes decompose producing unknown species with an intense blue/green color. An aliquot of the crude reaction mixture from the hydrolysis of (Z)-6 and (E)-6 in (9:1) 3N aqueous HCl/THF was made basic with ammonia water and extracted with chloroform. The left and center lanes were spotted and the TLC developed in 85:15 EtOAc/hexanes. This TLC plate was left out on the bench top for 30 min before a color change was observed.

The intermediate aldehydes were reduced in one pot by simply adding in $NaCNBH_3$ (Caution: HCN gas liberated!). 9-Hydroxymethyl phenylmorphans 7 and 8 were isolated in 69% combined yield with a dr of 1.5:1 favoring the beta epimer. O-demethylation of either epimer proceeds smoothly with $BBr_3$. The beta epimer of 14 was isolated in 81% yield compared to 70% for the alpha epimer of 14. The absolute configuration of 14 was determined by x-ray crystallographic analysis of its HBr salt.

3-(2-Phenethyl-9-propyl-2-azabicyclo[3.3.1]nonan-5-yl) phenol 15 (EG-1-203). A 10 mL round-bottomed flask was charged with enol ether 5 (0.360 g, 0.99 mmol) and taken up in 3N aqueous HCl (1.5 mL) and THF (1.5 mL). The reaction was stirred for 16 h at room temperature before being cooled to 0° C. and made basic by addition of chilled saturated aqueous $NH_4OH$. The bulk of the THF was stripped off on rotovap and the aqueous layer transferred to a separatory funnel. The aqueous phase was extracted with 9:1 $CHCl_3$/MeOH (3×5 mL) and the combined organic layers were dried over $MgSO_4$, filtered, and concentrated under vacuum to afford the epimeric aldehydes as a blue oil. The mixtures of aldehydes were used immediately in the subsequent step. A separate 10 mL round-bottomed flask was flame-dried under vacuum and charged with ethyltriphenylphosphonium iodide (1.24 g, 2.97 mmol) followed by a solution of the epimeric aldehydes from the first stage in THF (0.5 mL). The suspension was stirred for 5 min before being charged with LiHMDS (3.96 mL, 3.96 mmol, 1M solution in THF) dropwise over 15 min at 0° C. The color of the reaction changed from amber to deep red over the course of the LiHMDS addition. The reaction was stirred for 1.5 h at 0° C. and then 16 h at room temperature before being quenched by the addition of MeOH (2 mL). The bulk of the solvent was stripped off via rotary evacuator (bath temp 40° C.) and the residue was taken up in $H_2O$ (10 mL) and $CHCl_3$ (10 mL). The aqueous phase was extracted with 9:1 $CHCl_3$:MeOH (3×10 mL) and the combined organic layers were combined and dried over $MgSO_4$, filtered, and concentrated under vacuum. The resulting residue was purified via flash chromatography eluting with EtOAc/hexanes (0 to 100%) to afford the intermediate olefinic material as a mixture of alpha and beta epimers as well as E/Z isomers. This mixture of stereoisomers was taken up in MeOH (10 mL) and transferred to a 100 mL pressure tested reaction bottle. The vessel was charged with Escat 103 5% Pd/C (0.050 g, 10% w/w of phenylmorphan mixture). The vessel was pressurized to 50 psi $H_2$ in a Parr shaker and shaken for 16 h at room temperature. The reaction mixture was filtered through Celite and concentrated under vacuum to afford a yellow oil. The residue was purified by column chromatography eluting with EtOAc/hexanes (0 to 100%) to afford phenylmorphan 14 as a teal foam (0.103 g, 0.28 mmol, 28%). $R_f$=077 (1:1 EtOAc/hexanes); $^1$H-NMR (400 MHz; DMSO-$d_6$): δ 9.09 (s, 1H), 7.23-7.17 (m, 4H), 7.15-7.09 (m, 1H), 7.03 (t, J=7.9 Hz, 1H), 6.68 (d, J=8.0 Hz, 1H), 6.65 (t, J=1.8 Hz, 1H), 6.49 (dd, J=7.9, 1.8 Hz, 1H), 2.97-2.94 (m, 2H), 2.84-2.82 (m, 1H), 2.74-2.62 (m, 4H), 2.20 (d, J=14.6 Hz, 1H), 2.05 (q, J=10.9 Hz, 1H), 1.86-1.76 (m, 3H), 1.75-1.64 (m, 1H), 1.59-1.52 (m, 2H), 1.51-1.42 (m, 1H), 1.41-1.30 (m, 1H), 1.14-1.04 (m, 1H), 0.96-0.86 (m, 1H), 0.61 (t, J=7.3 Hz, 3H), 0.58-0.53 (m, 1H); $^{13}$C NMR (101 MHz; DMSO-$d_6$): δ 157.0, 151.9, 140.8, 128.8, 128.5, 127.9, 125.5, 115.8, 112.3, 112.0, 56.7, 56.2, 52.5, 48.4, 47.2, 44.8, 42.3, 42.0, 38.6, 33.4, 29.4, 28.4, 25.9, 23.0, 20.4, 14.2. HRMS-ESI (m/z): [M+H]$^+$ calcd. for $C_{25}H_{34}NO$ 364.2640, found 364.2645. The freebase was converted to its HBr salt for analysis. The HBr salt crystallized from i-PrOH/$Et_2O$. mp: 261-263° C.; $^1$H-NMR (400 MHz; DMSO-$d_6$): δ 9.32 (s, 1H), 8.54 (s, 1H), 7.39-7.30 (m, 4H), 7.29 (m, 1H), 7.13 (t, J=7.8 Hz, 1H), 6.77 (d, J=7.7 Hz, 1H), 6.70 (s, 1H), 6.61 (d, J=7.8 Hz, 1H), 3.76 (s, 1H), 3.58-3.43 (m, 3H), 3.13 (td, J=11.9, 4.6 Hz, 1H), 2.93 (td, J=11.9, 3.5 Hz, 1H), 2.36 (d, J=13.1 Hz, 1H), 2.29 (d, J=11.4 Hz, 1H), 2.25-2.13 (m, 2H), 2.06-1.86 (m, 3H), 1.74-1.66 (m, 2H), 1.53-1.33 (m, 2H), 1.14-1.06 (m, 1H), 0.91-0.82 (m, 1H), 0.78 (t, J=7.1 Hz, 3H). Anal. Calcd. For $C_{25}H_{34}BrNO\cdot 0.05C_3H_8O\cdot 0.4H_2O$ C, 66.44%; H, 7.80; N, 3.08%. Found C, 66.47%; H, 7.83%; N, 3.06%.

Figure 5:
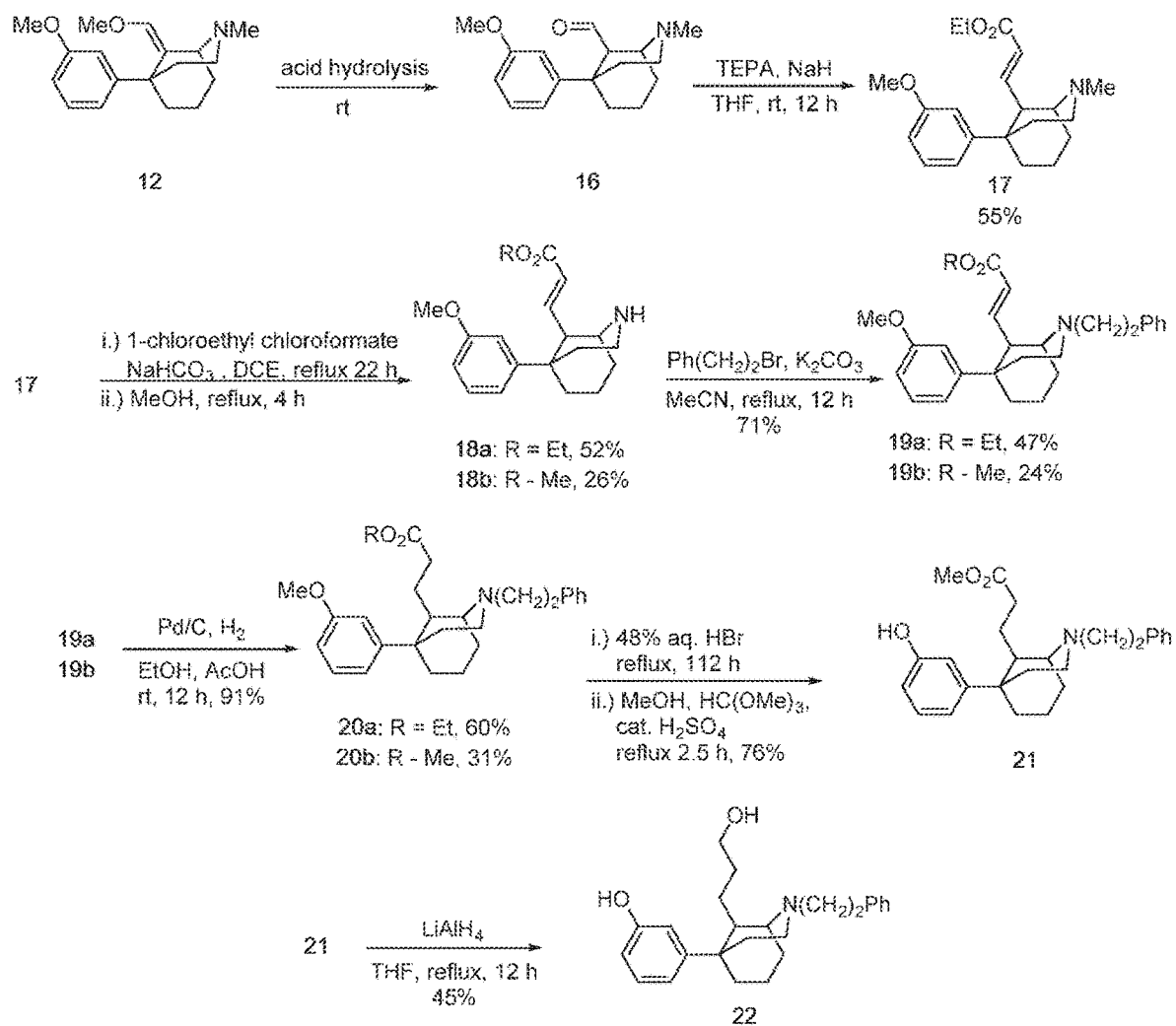
FIG. 5 shows a synthesis of exemplary compound 22.

Exemplary compound 22 was prepared according to a synthetic scheme shown in FIG. 5. The synthetic procedures for preparing compound 22 are described in FIG. 5.

Ethyl 3-(5-(3-methoxyphenyl)-2-methyl-2-azabicyclo [3.3.1]nonan-9-yl)acrylate (17 a/b). A single-neck 500 mL round-bottomed flask was charged with 60% NaH dispersion in mineral oil (4.81 g, 120.2 1 mmol) followed by dry THF (300 mL). Triethylphosphonoacetate (23.8 mL, 120.1 mmol) was added dropwise over 10 min., and stirred for 30 min affording a clear solution. A solution of 16 as a 1:2 mixture of diastereomers (6.57 g, 24.0 mmol) was taken up in THF (20 mL) and added dropwise to the reaction mixture. The reaction was allowed to stir under argon for 22 h at room temperature. The bulk of the THF was removed under vacuum and the residue was taken up in $Et_2O$ (100 mL) and 2N aqueous HCl (100 mL). The organic was separated and the aqueous phase basified by the addition of aqueous saturated $NH_4OH$. The alkaline aqueous layer was extracted with $CHCl_3$ (3×100 mL), dried over $MgSO_4$, filtered, and concentrated under vacuum. The residue was purified via flash chromatography eluting with $CHCl_3$/MeOH/saturated aqueous $NH_4OH$ (99:0.9:0.1 isocratic) to afford enone 17 as a 1:3 (/P) mixture of diastereomers favoring the less polar β isomer. The less polar β isomer (4.46 g, 13.0 mmol, 54%) was isolated as a green oil. $R_f$=0.55 (95:4.5:0.5 $CHCl_3$:MeOH:saturated aqueous $NH_4OH$). Spectral data matches that of previous reports*. More polar α isomer isolated as a dark oil: $R_f$=0.26 (95:4.5:0.5 $CHCl_3$:MeOH:saturated aqueous $NH_4OH$). $^1$H-NMR (400 MHz; CDCl$_3$): δ $^1$H NMR (400 MHz; CDCl$_3$): δ 7.20 (t, J=8.0 Hz, 1H), 6.92-6.87 (m, 3H), 6.70 (d, J=8.1 Hz, 1H), 5.81 (d, J=15.8 Hz, 1H), 4.10 (q, J=7.1 Hz, 3H), 3.77 (s, 3H), 3.25-3.23 (m, 3H), 3.09 (td, J=12.2, 4.9 Hz, 1H), 2.92 (s, 1H), 2.85 (dd, J=11.5, 7.7 Hz, 1H), 2.51 (s, 3H), 2.19-2.11 (m, 3H), 2.05-1.92 (m, 2H), 1.87-1.79 (m, 2H), 1.55-1.47 (m, 1H), 1.23 (q, J=6.4 Hz, 3H). HRMS-ESI (m/z): [M+H]$^+$ cald for $C_{21}H_{29}NO_3$ 344.2226, found 344.2232.

Methyl 3-(5-(3-methoxyphenyl)-2-azabicyclo[3.3.1]nonan-9-yl)acrylate (18a and 18b). A single-neck 100 mL round-bottomed flask was charged with enone 17 α/β (2.85 g, 8.3 mmol), DCE (21 mL), 1-chloroethyl chloroformate (5.35 mL, 49.8 mmol), and NaHCO$_3$ (4.88 g, 58.1 mmol). The resulting mixture was refluxed for 22 h under argon. The reaction mixture was cooled to room temperature and filtered through a sintered glass filter. The reaction flask was washed with CHCl$_3$ (3×10 mL) and the washings were used to rinse the solids remaining on top of the filter. The filtrate was concentrated under vacuum and taken up in MeOH (165 mL) and refluxed under argon for 5 h. The reaction mixture was allowed to cool to room temperature and concentrated under vacuum. The residue was purified via flash chromatography eluting with CHCl$_3$/MeOH/NH$_4$OH (99:0.9:0.1 to 80:18:2) to afford N-nor phenylmorphans 18a and 18b (2.14 g, 6.5 mmol, 78%). The product ratios shown above arise from $^1$H NMR analysis of the crude reaction mixture.

N-nor phenylmorphan (18). R$_f$=0.46 (90:9:1 CHCl$_3$:MeOH:sat. aq. NH$_4$OH). ($^1$H-NMR (400 MHz; DMSO-d$_6$): δ 7.19 (t, J=7.9 Hz, 1H), 6.98 (dd, J=15.7, 8.5 Hz, 1H), 6.90 (d, J=7.9 Hz, 1H), 6.83 (s, 1H), 6.71 (d, J=7.9 Hz, 1H), 5.82 (d, J=15.8 Hz, 1H), 4.00 (q, J=7.0 Hz, 2H), 3.72 (s, 3H), 3.57-3.49 (m, 1H), 3.05 (s, 1H), 3.05-2.96 (m, 2H), 2.16-1.62 (m, 9H), 1.14 (t, J=7.1 Hz, 3H). $^{13}$C NMR (101 MHz; DMSO-d$_6$): δ 165.6, 158.9, 151.6, 151.3, 128.9, 121.6, 117.7, 111.7, 110.4, 59.5, 54.8, 52.3, 46.4, 41.45, 41.44, 38.4, 33.0, 29.7, 22.6, 14.0. HRMS-ESI (m/z): [M+H]$^+$ cald for $C_{20}H_{27}NO_3$ 330.2069, found 330.2073.

Methyl 3-(5-(3-methoxyphenyl)-2-phenethyl-2-azabicyclo[3.3.1]nonan-9-yl)acrylate (19a and 19b). A single-neck 200 mL round-bottomed flask was charged with a mixture N-nor phenylmorphans 17a/17b (2.14 g, 6.51 mmol) from the previous step, K$_2$CO$_3$ (1.80 g, 13.03 mmol), phenethyl bromide (1.33 mL, 9.77 mmol), and MeCN (65 mL). The reaction flask was fitted with a reflux condenser and the reaction was heated to reflux for 12 h under argon. The reaction was cooled to room temperature and the bulk of the MeCN was removed under vacuum. The residue was taken up in deionized H$_2$O and extracted with CHCl$_3$ (3×50 mL). The combined organic layers were washed with brine (1×150 mL), dried over Na$_2$SO$_4$, decanted, and concentrated under vacuum. The residue was purified via flash chromatography eluting with EtOAc/hexanes (1:9 to 1:1) to afford phenylmorphans 19a and 19b (1.97 g, 4.6 mmol, 71%) as an amber oil. The product ratios shown above arise from $^1$H NMR analysis of the crude reaction mixture.

Phenylmorphan 19a. $^1$H-NMR (400 MHz; CDCl$_3$): δ 7.32-7.05 (m, 7H), 6.87 (d, J=7.9 Hz, 1H), 6.82 (s, 1H), 6.69 (dd, J=8.1, 1.7 Hz, 1H), 5.72 (d, J=15.8 Hz, 1H), 4.09 (q, J=6.7 Hz, 2H), 3.79 (s, 3H), 3.19-3.08 (m, 3H), 2.85 (d, J=8.4 Hz, 1H), 2.81-2.70 (m, 4H), 2.41 (q, J=10.7 Hz, 1H), 2.30 (dd, J=13.6, 4.8 Hz, 1H), 2.08 (dd, J=12.8, 3.8 Hz, 1H), 2.03-1.89 (m, 1H), 1.86-1.77 (m, 2H), 1.73-1.64 (m, 1H), 1.55-1.45 (m, 1H), 1.23 (t, J=7.1 Hz, 3H). $^{13}$C NMR (101 MHz; CDCl$_3$): δ 166.7, 159.4, 151.2, 150.8, 140.9, 129.0, 128.8, 128.2, 125.8, 121.9, 118.2, 112.4, 110.3, 59.9, 57.9, 57.1, 55.2, 49.07, 49.02, 42.1, 38.7, 34.3, 30.4, 25.7, 23.1, 14.3. HRMS-ESI (m/z): [M+H]$^+$ cald for $C_{28}H_{36}NO_3$ 434.2695, found 434.2698.

Ethyl 3-(5-(3-methoxyphenyl)-2-phenethyl-2-azabicyclo[3.3.1]nonan-9-yl)propanoate 18ab. A mixture of phenylmorphans 19a/19b (1.97 g, 4.6 mmol) from the previous step was dissolved in EtOH (46 mL) and transferred to a 250 mL pressure tested reaction bottle. The vessel was charged with aqueous AcOH (0.26 mL, 4.56 mmol) and Escat 103 5% Pd/C (0.20 g, 10% w/w). The vessel was pressurized to 50 psi H$_2$ in a Parr shaker and shaken for 12 at room temperature. The reaction mixture was filtered through Celite and concentrated under vacuum to afford a yellow oil. The residue was purified via flash chromatography eluting with CHCl$_3$/MeOH/NH$_4$OH (99:0.9:0.1 isocratic) to afford phenylmorphans 20a and 20b (1.80 g, 4.6 mmol, 91%) as an amber oil. The product ratios shown above arise from $^1$H NMR analysis of the crude reaction mixture. $^1$H-NMR (400 MHz; CDCl$_3$): δ 7.28-7.20 (m, 5H), 7.16 (t, J=6.9 Hz, 1H), 6.90 (d, J=7.8 Hz, 1H), 6.86 (s, 1H), 6.71 (dd, J=8.1, 1.6 Hz, 1H), 4.06 (qd, J=7.1, 2.2 Hz, 2H), 3.81 (s, 3H), 3.07 (d, J=7.7 Hz, 2H), 2.89 (s, 1H), 2.80-2.73 (m, 4H), 2.37-2.28 (m, 2H), 2.13-2.06 (m, 1H), 2.02-1.60 (m, 9H), 1.46-1.36 (m, 1H), 1.22 (t, J=7.1 Hz, 3H). $^{13}$C NMR (101 MHz; CDCl$_3$): δ 166.7, 166.3, 159.5, 150.4, 149.0, 148.7, 129.1, 123.1, 122.8, 118.13, 118.11, 112.1, 110.8, 60.1, 59.91, 59.87, 55.1, 51.34, 51.20, 48.86, 48.80, 42.9, 41.2, 37.7, 29.6, 22.0, 18.9, 14.2. HRMS-ESI (m/z): [M+H]$^+$ calcd for $C_{28}H_{38}NO_3$ 436.2852, found 436.2851.

Methyl 3-((5-(3-hydroxyphenyl)-2-phenethyl-2-azabicyclo[3.3.1]nonan-9-yl)propanoate (21). A 200 mL round-bottomed flask was charged with a mixture of phenylmorphans 19a/19b (1.243 g, 2.86 mmol) from the previous step and 48% aqueous HBr (57 mL). A small amount of MeOH (7 mL) was added to the reaction to help solubilize the phenylmorphans. The reaction flask was equipped with a reflux condenser and refluxed under argon for 12. The reaction was cooled to room temperature and the reflux condenser was removed and replaced with a short-path distillation head. The bulk of the 48% aqueous HBr was removed by vacuum distillation (40 mbar, 90° C.) affording a yellow oil. The oil was taken up in MeOH (57 mL) and the flask was charged with trimethyl orthoformate (0.94 mL, 8.57 mmol) and a catalytic amount of H$_2$SO$_4$ (0.2 mL). The reaction flask was equipped with a reflux condenser and heated to reflux under argon for 2.5 h. The reaction mixture was cooled to 0° C. and quenched by the addition of 7 N methanolic ammonia (0.8 mL). The crude reaction mixture was concentrated in vacuo and purified via flash chromatography eluting with CHCl$_3$/MeOH/NH$_4$OH (99:0.9:0.1 to 80:18:2) to afford 21 as a yellow oil. R$_f$=0.78 (85:13.5:1.5 CHCl$_3$:MeOH:sat. aq. NH$_4$OH). $^1$H-NMR (400 MHz; DMSO-d$_6$): δ 9.17 (s, 1H), 7.26-7.17 (m, 4H), 7.17-7.10 (m, 1H), 7.08 (t, J=7.9 Hz, 1H), 6.72 (d, J=7.8 Hz, 1H), 6.68 (s, 1H), 6.54 (d, J=8.3 Hz, 1H), 3.54-3.47 (m, 3H), 3.00 (d, J=8.4 Hz, 2H), 2.82 (s, 1H), 2.79-2.64 (m, 4H), 2.22 (d, J=12.7 Hz, 1H), 2.17-1.98 (m, 2H), 1.99-1.80 (m, 4H), 1.80-1.65 (m, 3H), 1.65-1.52 (m, 2H), 1.45-1.29 (m, 1H), 1.01 (q, J=8.5 Hz, 1H), 1.06-0.95 (m, 1H). $^{13}$C NMR (101 MHz; DMSO-d$_6$): δ 173.4, 157.0, 151.5, 140.6, 128.8, 128.5, 127.9, 125.4, 115.8, 112.26, 112.07, 56.2, 52.2, 50.9, 48.3, 43.9, 42.3, 38.4, 33.4, 31.4, 29.2, 25.6, 22.8, 21.7. HRMS-ESI (m/z): [M+H]$^+$ cald for $C_{26}H_{34}NO_3$ 408.2539, found 408.2546. The free base was converted into its HCl salt for analysis. Anal. Calcd for $C_{26}H_{34}ClNO_3 \cdot 0.25H_2O$ C, 69.63%; H, 7.75%; N, 3.12%. Found C, 69.95%, H, 7.54%, N, 3.10%.

3-(9-(2-Hydroxyethyl)-2-phenethyl-2-azabicyclo[3.3.1]nonan-5-yl)phenol (22). A 50 mL single-neck round-bottomed flask was charged with 21 (0.542 g, 1.33 mmol) and THF (27 mL). The flask was cooled to 0° C. and LiAlH$_4$ (2.66 mL, 2.66 mmol, 1 M in THF) was added dropwise via syringe. The flask stirred for 30 min gradually warming to room temperature. The flask was equipped with a reflux condenser and the reaction was heated to reflux for 20 h under argon. The reaction was cooled to 0° C. and quenched by the drop-wise addition of 2M aqueous Rochelle salt (25 mL). The crude reaction mixture was stirred for 4 h affording a cloudy 2 phase mixture. The less dense THF layer was separated and the aqueous layer was basified to pH 9 with saturated aqueous $NH_4OH$. The aqueous layer was extracted with $CHCl_3$ (3×25 mL) and the combined organic layers including the previously separated THF layer were combined and dried over $MgSO_4$, filtered, and concentrated under vacuum. The resulting residue was purified via flash chromatography eluting with $CHCl_3/MeOH/NH_4OH$ (99:0.9:0.1 to 80:18:2) to afford 22 (0.220 g, 0.58 mmol, 44%) as a yellow foam. $R_f$=0.41 (90:0.9:0.1 $CHCl_3$:MeOH:saturated aqueous $NH_4OH$). H NMR (400 MHz; DMSO-$d_6$): δ 9.14 (s, 1H), 7.27-7.20 (m, 4H), 7.20-7.12 (m, 1H), 7.06 (t, J=7.9 Hz, 1H), 6.72 (d, J=8.1 Hz, 1H), 6.68 (s, 1H), 6.53 (d, J=8.1 Hz, 1H), 4.18 (t, J=4.9 Hz, 1H), 3.20-3.08 (m, 2H), 3.04-2.94 (m, 2H), 2.91 (s, 1H), 2.80-2.64 (m, 4H), 2.24 (d, J=14.5 Hz, 1H), 2.09 (q, J=11.1 Hz, 1H), 1.94-1.77 (m, 3H), 1.78-1.66 (m, 1H), 1.66-1.54 (m, 2H), 1.54-1.25 (m, 3H), 1.22-1.05 (m, 1H), 0.85-0.63 (m, 1H). $^{13}$C NMR (101 MHz; DMSO-$d_6$): δ 157.5, 152.4, 141.2, 129.3, 129.0, 128.5, 126.1, 116.3, 112.8, 112.5, 61.7, 56.8, 52.9, 49.0, 45.4, 42.7, 39.1, 34.0, 31.6, 29.8, 26.3, 23.5, 23.1. HRMS-ESI (m/z): [M+H]$^+$ calcd. for $C_{25}H_{34}NO_2$ 380.2590, found 380.2592. The free base was converted to the HBr salt for analysis. mp: 259-262° C. Anal. Calcd. For $C_{25}H_{34}BrNO_2$. 0.05$H_2O$ C, 65.09%; H, 7.45; N, 3.04%. Found C, 65.09%; H, 7.27%; N, 3.00%.

Figure 6:
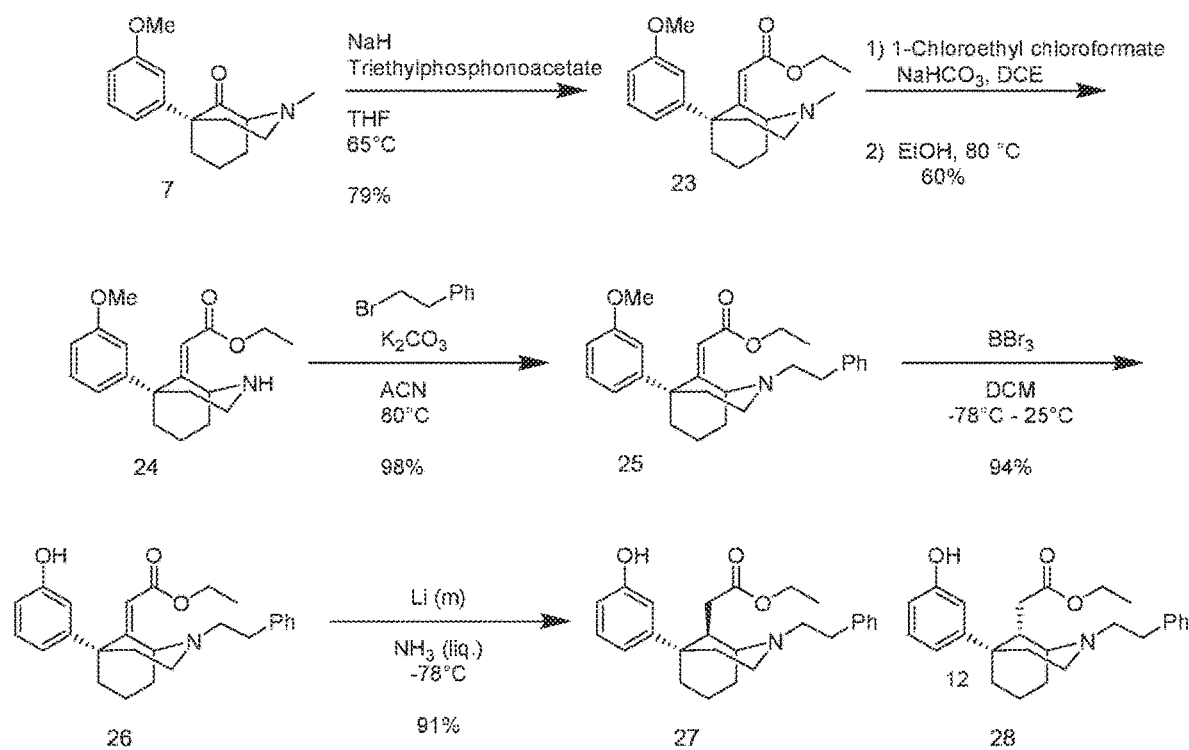
FIG. 6 shows a synthesis of exemplary compound 26-28.

Exemplary compounds 27 and 28 were prepared according to a synthetic scheme shown in FIG. 6. The synthetic procedures for preparing compounds 27 and 28 are described in FIG. 6.

Ethyl (Z)-2-(5-(3-methoxyphenyl)-2-methyl-2-azabicyclo[3.3.1]nonan-9-ylidene)acetate ((−)-23). Triethyl phosphonoacetate (40.5 mmol, 8.0 mL) was slowly added to a cooled suspension of sodium hydride (40.5 mmol, 1.55 g, 60% suspension in mineral oil) in anhydrous THF (50 mL), and stirred until the solution became clear. A solution of 7 (13.5 mmol, 3.5 g) in anhydrous THF (50 mL) was then added and the reaction heated to reflux and stirred for 16 h. The reaction was cooled, quenched with $H_2O$, extracted with EtOAc (3×50 mL), dried with $Na_2SO_4$, filtered and concentrated in vacuo. The resultant oil was dissolved in warm (50° C.) acetone (50 mL), and a solution of oxalic acid (13.5 mmol, 1.22 g) in acetone (10 mL). The reaction was allowed to cool to room temperature, during which time crystals began forming. After 1 h at room temperature, the reaction was stirred at 0° C. for 1 h, and crystals collected by filtration, washed with acetone and ether, sequentially, to give the oxalate salt of 30. The salt was free-based with $NH_4OH/H_2O$, extracted with $CHCl_3$ (3×50 mL), dried with $Na_2SO_4$, filtered and concentrated in vacuo to afford 23 as a clear oil (4.1 g, 92% yield). $^1$H-NMR (400 MHz; CDCl$_3$): δ 7.24 (s, 1H), 6.93-6.88 (m, 2H), 6.77 (dd, J=8.0, 1.8 Hz, 1H), 5.15 (s, 1H), 4.92 (s, 1H), 4.04 (q, J=7.1 Hz, 2H), 3.79 (s, 3H), 3.15 (ddd, J=12.2, 8.6, 4.2 Hz, 1H), 2.70 (dt, J=11.8, 5.9 Hz, 1H), 2.50 (s, 4H), 2.16 (d, J=12.0 Hz, 4H), 2.05 (dt, J=13.8, 5.2 Hz, 1H), 1.70 (d, J=3.4 Hz, 1H), 1.60-1.57 (m, 1H), 1.17 (t, J=7.1 Hz, 3H). $^{13}$C-NMR (101 MHz; CDCl$_3$): δ 166.91 (s, 1C), 166.59 (s, 1C), 159.28 (s, 1C), 148.45 (s, 1C), 128.96 (s, 1C), 120.10 (s, 1C), 114.24 (s, 1C), 114.00 (s, 1C), 111.06 (s, 1C), 59.69 (s, 1C), 56.37 (s, 1C), 55.20 (s, 1C), 50.16 (s, 1C), 45.23 (s, 1C), 43.92 (s, 1C), 40.18 (s, 1C), 38.87 (s, 1C), 29.60 (s, 1C), 20.66 (s, 1C), 14.18 (s, 1C). HRMS (TOF MS ES+) calc for $C_{20}H_{27}NO_3$ (M+H$^+$), 330.2069 found 330.2072. $[\alpha]^{20}_D$ −20.3° (c 1.21, CHCl$_3$). For (1R,5R)-(+)-23, $[\alpha]^{20}_D$ −20.2° (c 1.82, CHCl$_3$).

Ethyl (Z)-2-(5-(3-methoxyphenyl)-2-azabicyclo[3.3.1]nonan-9-ylidene)acetate ((+)-24). To a suspension of $NaHCO_3$ (56.8 mmol, 4.77 g) in anhydrous DCE (50 mL) was added 23 (8.12 mmol, 3.40 g) and 1-chloroethyl chloroformate (48.72 mmol, 5.30 mL) and heated to 60° C. After 18 h, the reaction was cooled, filtered through celite and concentrated in vacuo. The resultant oil was dissolved in EtOH (50 mL) and refluxed for 3 h, then cooled and concentrated in vacuo. The resultant crude oil was purified by flash column chromatography on silica gel (10% $NH_4OH/EtOH$ in $CHCl_3$, gradient 0-10%) to afford 24 as a yellow oil (1.44 g, 56% yield) and some recovered starting material (0.38 g, 15%). $^1$H-NMR (400 MHz; CDCl$_3$): δ 7.24 (s, 1H), 6.91 (d, J=7.9 Hz, 1H), 6.86 (s, 1H), 6.76 (d, J=8.1 Hz, 1H), 5.17 (s, 1H), 5.12 (s, 1H), 4.04 (q, J=7.1 Hz, 2H), 3.79 (s, 3H), 3.46 (ddd, J=13.5, 9.2, 4.5 Hz, 1H), 2.96 (dt, J=12.8, 6.1 Hz, 1H), 2.39 (td, J=13.4, 7.2 Hz, 1H), 2.33-2.22 (m, 1H), 2.17 (dd, J=8.9, 6.2 Hz, 2H), 2.13-2.04 (m, 2H), 1.94 (s, 1H), 1.88 (dt, J=12.4, 6.1 Hz, 1H), 1.74-1.71 (m, 1H), 1.17 (t, J=7.1 Hz, 3H). $^{13}$C-NMR (101 MHz; CDCl$_3$): δ 169.19 (s, 1C), 166.62 (s, 1C), 159.31 (s, 1C), 148.58 (s, 1C), 128.98 (s, 1C), 119.99 (s, 1C), 113.98 (s, 1C), 113.37 (s, 1C), 110.84 (s, 1C), 59.73 (s, 1C), 55.18 (s, 1C), 49.06 (s, 1C), 46.13 (s, 1C), 42.25 (s, 1C), 41.53 (s, 1C), 40.07 (s, 1C), 34.39 (s, 1C), 20.52 (s, 1C), 14.18 (s, 1C). HRMS (TOF MS ES+) calc for $C_{19}H_{25}NO_3$ (M+H$^+$), 316.1913 found 316.1913. $[\alpha]^{20}_D$+44.5° (c 2.40, CHCl$_3$). For (1R,5R)-(−)-24, $[\alpha]^{20}_D$ −43.9° (c 2.12, CHCl$_3$).

Ethyl (Z)-2-(5-(3-methoxyphenyl)-2-phenethyl-2-azabicyclo[3.3.1]nonan-9-ylidene)acetate ((−)-25). To solution of 24 (4.44 mmol, 1.40 g) and (2-bromoethyl)benzene (6.66 mmol, 0.91 mL) in anhydrous acetonitrile (50 mL), $K_2CO_3$ (8.88 mmol, 1.23 g) was added and the reaction refluxed for 18 hours. The reaction was then cooled, filtered and concentrated in vacuo. The crude oil was purified by flash column chromatography on silica gel (10% $NH_4OH/MeOH$ in $CHCl_3$, gradient 0-10%) to afford 25 as a clear oil (1.71 g, 92% yield). $^1$H-NMR (400 MHz; CDCl$_3$): δ 7.23 (ddt, J=22.6, 14.7, 7.3 Hz, 6H), 6.94-6.88 (m, 2H), 6.78 (d, J=8.2 Hz, 1H), 5.16 (d, J=3.9 Hz, 2H), 4.07 (q, J=7.1 Hz, 2H), 3.80 (s, 3H), 3.14 (dt, J=11.7, 5.9 Hz, 1H), 2.89-2.76 (m, 5H), 2.44 (dt, J=13.6, 6.6 Hz, 1H), 2.23-2.07 (m, 5H), 1.69-1.55 (m, 2H), 1.19 (t, J=7.1 Hz, 3H). $^{13}$C-NMR (101 MHz; CDCl$_3$): δ 167.52 (s, 1C), 166.61 (s, 1C), 159.31 (s, 1C), 148.89 (s, 1C), 140.61 (s, 1C), 128.98 (s, 1C), 128.78 (s, 1C), 128.25 (s, 1C), 125.85 (s, 1C), 120.13 (s, 1C), 114.64 (s, 1C), 114.04 (s, 1C), 110.92 (s, 1C), 59.71 (s, 1C), 58.88 (s, 1C), 55.20 (s, 1C), 54.79 (s, 1C), 48.57 (s, 1C), 45.79 (s, 1C), 40.19 (s, 1C), 39.01 (s, 1C), 34.52 (s, 1C), 31.83 (s, 1C), 19.91 (s, 1C), 14.22 (s, 1C). HRMS (TOF MS ES+) calc for $C_{27}H_{34}NO_3$ (M+H$^+$), 420.2539 found 420.2538. $[\alpha]^{20}_D$ −18.0° (c 2.86, CHCl$_3$). For (1R,5R)-(+)-25, $[\alpha]^{20}_D$+ 17.9° (c 1.55, CHCl$_3$).

Ethyl (Z)-2-(5-(3-hydroxyphenyl)-2-phenethyl-2-azabicyclo[3.3.1]nonan-9-ylidene)acetate ((−)-26, EWB-2-189). To a cooled (−78° C.) solution of 25 (1.19 mmol, 0.50 g) in anhydrous DCM (25 mL), was added BBr$_3$ (5.96 mmol, 0.57 mL) dropwise over 10 min. The reaction was stirred at −78° C. for 30 min, and allowed to warm to room temperature by removing the dry ice bath. After 1 h at room temperature, the reaction was quenched with EtOH, then $H_2O$ and 28% $NH_4OH$, and extracted with DCM (3×25 mL), dried over $Na_2SO_4$, filtered and concentrated in vacuo. The crude product was purified by flash column chromatography on silica gel (10% $NH_4OH/MeOH$ in $CHCl_3$, gradient 0-10%)

to afford 26 as a white foam (0.48 g, 99% yield). ¹H-NMR (400 MHz; CDCl₃): δ 7.26 (t, J=7.5 Hz, 2H), 7.21-7.16 (m, 3H), 6.87 (d, J=7.9 Hz, 1H), 6.81 (s, 1H), 6.70 (dd, J=8.0, 2.2 Hz, 1H), 5.23 (s, 1H), 5.20 (s, 1H), 4.09-3.97 (m, 2H), 3.20 (ddd, J=11.9, 7.7, 4.5 Hz, 1H), 2.90-2.81 (m, 4H), 2.47 (dt, J=14.5, 6.9 Hz, 1H), 2.19-2.07 (m, 4H), 1.71-1.61 (m, 2H), 1.15 (t, J=7.1 Hz, 2H). ¹³C-NMR (101 MHz; CDCl₃): δ 166.70 (s, 1C), 155.84 (s, 1C), 148.75 (s, 1C), 140.26 (s, 1C), 129.19 (s, 1C), 128.79 (s, 1C), 128.32 (s, 1C), 125.97 (s, 1C), 119.50 (s, 1C), 119.47 (s, 1C), 115.08 (s, 1C), 114.94 (s, 1C), 113.71 (s, 1C), 59.84 (s, 1C), 58.68 (s, 1C), 54.63 (s, 1C), 48.44 (s, 1C), 45.59 (s, 1C), 40.16 (s, 1C), 38.44 (s, 1C), 34.20 (s, 1C), 31.15 (s, 1C), 20.15 (s, 1C), 14.16 (s, 1C). HRMS (TOF MS ES+) calc for $C_{27}H_{34}NO_3$ (M+H⁺), 406.2382 found 406.2377. $[\alpha]^{20}_D$ –18.4° (c 2.31, CHCl₃). For (1R,5R)-(+)-262, $[\alpha]^{20}_D$+18.7° (c 2.17, CHCl₃).

Ethyl 2-(5-(3-hydroxyphenyl)-2-phenethyl-2-azabicyclo [3.3.1]nonan-9-yl)acetate (27 and 28, EWB-2-190 alpha and EWB 2-177 beta). To a suspension of lithium wire (2.0 mmol, 14.0 mg) in liq NH₃ (50 mL) at –78° C., was added 26 (0.5 mmol, 210 mg) in anhydrous ether (3 mL), and stirred under argon for 5 min. The reaction was then quenched by rapidly adding NH₄Cl (10 mmol, 535 mg), and allowed to warm to room temperature slowly, allowing the liquid NH₃ to evaporate. The solids were then dissolved in H₂O and 28% NH₄OH and extracted with CHCl₃ (3×25 mL), dried over Na₂SO₄, and concentrated in vacuo. The crude products were purified by flash column chromatography on silica gel (10% NH₄OH/MeOH in CHCl₃, gradient 0-10%) to afford 27 as a clear oil (130 mg, 62% yield) and 28 as a clear oil (61 mg, 29% yield). For 27: ¹H-NMR (400 MHz; CDCl₃): δ 7.21 (dq, J=20.7, 7.5 Hz, 5H), 6.92 (d, J=7.8 Hz, 1H), 6.87 (s, 1H), 6.70 (d, J=8.1 Hz, 1H), 4.01 (q, J=7.1 Hz, 2H), 3.78 (s, 3H), 3.08 (td, J=12.0, 5.2 Hz, 1H), 3.02-2.95 (m, 2H), 2.85-2.70 (m, 5H), 2.62 (d, J=9.9 Hz, 1H), 2.26 (d, J=14.0 Hz, 1H), 2.16-2.07 (m, 1H), 1.99 (dd, J=13.4, 4.6 Hz, 1H), 1.93-1.81 (m, 3H), 1.75-1.65 (m, 2H), 1.58-1.51 (m, 1H), 1.17 (t, J=7.0 Hz, 3H). ¹³C-NMR (101 MHz, CDCl₃): δ 174.26, 159.58, 151.53, 129.19, 128.68, 128.13, 125.70, 117.85, 111.81, 110.49, 59.88, 56.69, 55.11, 54.43, 48.92, 42.55, 41.75, 38.65, 34.35, 32.70, 30.12, 25.68, 23.33, 14.21. HRMS (TOF MS ES+) calc for $C_{26}H_{34}NO_3$ (M+H⁺), 408.2539 found 408.2538. For 28: ¹H-NMR (400 MHz; CDCl₃): δ 7.24 (tq, J=14.6, 7.4 Hz, 6H), 7.01-6.96 (m, 2H), 6.72 (d, J=8.1 Hz, 1H), 4.03 (q, J=7.1 Hz, 2H), 3.79 (s, 3H), 3.00 (d, J=6.8 Hz, 3H), 2.88-2.78 (m, 5H), 2.24 (dd, J=14.8, 11.3 Hz, 2H), 2.08-1.92 (m, 6H), 1.78 (d, J=12.7 Hz, 2H), 1.55-1.50 (m, 1H), 1.18 (t, J=7.1 Hz, 3H), 0.85 (q, J=7.6 Hz, 2H). ¹³C-NMR (101 MHz, CDCl₃): δ 173.01, 159.61, 150.91, 140.66, 129.22, 128.72, 128.30, 125.92, 118.05, 111.92, 110.87, 60.18, 58.05, 55.14, 54.41, 49.69, 42.01, 41.22, 38.22, 34.54, 33.43, 28.95, 21.58, 18.61, 14.21. HRMS (TOF MS ES+) calc for $C_{26}H_{34}NO_3$ (M+H⁺), 408.2539 found 408.2545.

Figure 7:
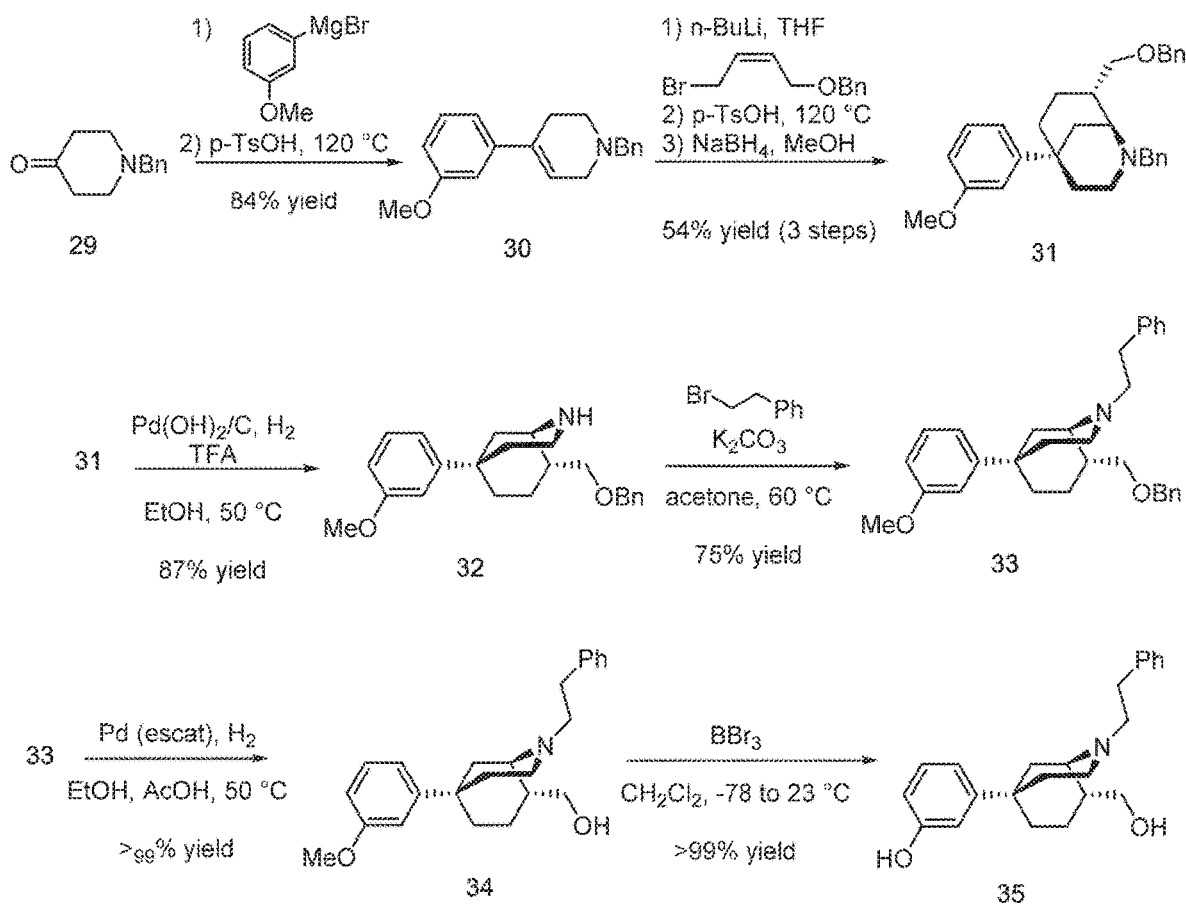
FIG. 7 shows a synthesis of exemplary compounds 35.

Exemplary compound 35 was prepared according to a synthetic scheme shown in FIG. 7. The synthetic procedures for preparing compound 35 is described in FIG. 7.

2-Benzyl-8-((benzyloxy)methyl)-5-(3-methoxyphenyl)-2-azabicyclo[3.3.1]nonane (31). Tetrahydropyridine 30 was synthesized from 29 following our previously reported procedure. Following that procedure, to a stirred solution of 1-benzyl-4-(3-methoxyphenyl)-1,2,3,6-tetrahydropyridine 29 (5.30 g, 19.0 mmol) in THF (55 mL) at –78° C. was added n-BuLi (9.00 mL, 22.5 mmol, 2.5 M solution in hexanes) dropwise. The mixture was stirred for 15 min. then warmed to 0° C. over 1 h. The reaction mixture was cooled to –50° C., and freshly prepared (Z)-(((4-bromobut-2-en-1-yl)oxy)methyl)benzene (4.60 g, 19.0 mmol, prepared according to Hirano, K.; Biju, A. T.; Piel, I.; Glorius, F. *J. Am. Chem. Soc.* 2009, 131, 14190-14191) was added in one portion and the mixture was allowed to warm to room temperature over 1 h. The mixture was quenched with brine (50 mL) and the organic layer was separated. The aqueous layer was extracted with EtOAc (3×30 mL) and the combined organic layers were washed with brine (80 mL) and dried over MgSO₄. The solvent was removed via rotary evaporation and the crude intermediate was carried directly to the next transformation without further purification. The crude oil was dissolved in toluene (150 mL) and treated with p-TsOH.H₂O (4.70 g, 24.7 mmol). The reaction vessel was fitted with a Dean-Stark apparatus and refluxed for 2 d. The reaction mixture was cooled to ambient temperature and diluted with MeOH/CHCl₃ (2:1, 75 mL). The resulting solution was directly reduced by adding NaBH₄ (1.50 g, 39.5 mmol) in small portions over 1 h and the mixture was stirred at ambient temperature for 2 h. The solution was diluted with water (100 mL) and the layers were separated. The aqueous layer was extracted with EtOAc (3×100 mL) and the combined organic layers were washed with brine (200 mL) and dried over MgSO₄. The crude product was purified by gradient column chromatography (100% hexanes-→9:1 hexanes/EtOAc) to give 31, visualized by iodine stain. H NMR (400 MHz, CDCl₃): δ 7.40-7.18 (comp. m, 11H), 6.91 (d, J=7.5 Hz, 1H), 6.86 (br. s, 1H), 6.72 (d, J=7.5 Hz, 1H), 4.48 (s, 2H), 3.80 (s, 3H), 3.79 (d, J=13.3 Hz, 1H), 3.62 (d, J=13.3 Hz, 1H), 3.35 (d, J=6.9 Hz, 2H), 3.07 (br. s, 1H), 2.95-2.85 (m, 1H), 2.79-2.69 (m, 1H), 2.39-2.29 (m, 1H), 1.49-2.04 (comp. m, 8H); ¹³C NMR (100 MHz, CDCl₃): δ 159.6, 138.6, 129.3, 129.1, 129.0, 128.9, 128.7, 128.5, 128.4, 127.64, 127.61, 117.4, 111.5, 110.4, 73.1, 55.3, 55.0, 47.1, 34.79, 34.77, 34.7, 31.7, 31.6, 24.2, 14.3. HRMS (ESI+) m/z calc. for (M+H)⁺[$C_{30}H_{35}NO_2$+H]+: 442.2746, found: 442.2754.

8-((Benzyloxy)methyl)-5-(3-methoxyphenyl)-2-azabicyclo[3.3.1]nonane (32). Benzyl ether 31 (6.30 g, 14.3 mmol) was dissolved in ethanol (140 mL) in a shaker hydrogenation apparatus. To the solution was added Pd(OH)₂/C (630 mg, 10% w/w of starting material), and trifluoroacetic acid (0.50 mL, 5.72 mmol, 0.4 equiv). Bernotas, R. C.; Cube, R. V. *Synth. Comm.* 1990, 20, 1209-1212. The reaction vessel was securely placed onto a Parr instrument shaker and heated at 50° C. under a hydrogen atmosphere overnight. The reaction mixture was allowed to cool to room temperature, purged with nitrogen, and filtered through celite (EtOH eluent). The volatiles were removed via rotary evaporation and nor compound 32 was obtained as a colorless oil (4.40 g, 87% yield). $R_f$=0.30 in CMA, visualized by iodine stain. ¹H NMR (400 MHz, CDCl₃): δ 7.37-7.27 (comp. m, 5H), 7.23 (d, J=8.0 Hz, 1H), 6.89 (ddd, J=8.0, 2.1, 0.8 Hz, 1H), 6.82 (t, J=2.1 Hz, 1H), 6.74 (ddd, J=8.0, 2.1, 0.8 Hz, 1H), 4.52 (d, J=12.1 Hz, 1H), 4.49 (d, J=12.1 Hz, 1H), 3.80 (s, 3H), 3.57 (br. s, 1H), 3.52-3.38 (comp. m, 3H), 3.10 (dd, J=13.5, 6.9 Hz, 1H), 2.27 (app. dt, J=12.5, 6.1 Hz, 1H), 2.15-2.04 (m, 1H), 2.03-1.74 (comp. m, 6H), 1.54 (app. td, J=13.0, 7.4 Hz, 1H; ¹³C NMR (100 MHz, CDCl₃): δ 159.7, 153.3, 138.4, 129.5, 128.6, 127.8, 127.7, 117.2, 111.4, 110.7, 77.4, 73.1, 72.9, 55.3, 51.6, 49.9, 40.0, 37.5, 34.4, 32.6, 23.7. HRMS (free base) (ESI+) m/z calc. for (M+H)⁺ [$C_{23}H_{29}NO_2$+H]⁺: 352.2277, found: 352.2278.

8-((Benzyloxy)methyl)-5-(3-methoxyphenyl)-2-phenethyl-2-azabicyclo[3.3.1]nonane (33). Nor compound 32 (380 mg, 1.08 mmol) was dissolved in acetone (2.0 mL), treated with potassium carbonate (448 mg, 3.24 mmol), and stirred for 15 minutes at which point phenethyl bromide (0.20 mL, 1.19 mmol) was added dropwise and the suspension was refluxed overnight. Next day the reaction mixture was filtered through celite, concentrated, and purified via flash chromatography (100% hexanes→3:1 hexanes/EtOAc) to yield phenethylamine 33 as a light yellow oil (369 mg, 75% yield). $R_f$=0.33 in 3:1 hexanes/EtOAc eluent. $^1$H NMR (400 MHz, CDCl$_3$): δ 7.34-7.16 (comp. m, 11H), 6.91 (d, J=8.0 Hz, 1H0, 6.87 (br. s, 1H), 6.73 (dd, J=8.0, 2.4 Hz, 1H), 4.51 (s, 2H), 3.80 (s, 3H), 3.39 (app. quintet, 2H), 3.20 (br. s, 1H), 2.94-2.62 (comp. m, 6H), 2.32-2.22 (m, 1H), 2.07-1.70 (comp. m, 7H), 1.57-1.46 (m, 1H); $^{13}$C NMR (100 MHz, DMSO-d$_6$): δ 159.6, 138.3, 129.3, 129.1, 128.9, 128.7, 128.5, 127.73, 127.67, 126.2, 117.4, 111.5, 110.5, 73.3, 56.8, 55.3, 54.9, 47.7, 37.8, 34.54, 34.52, 33.6, 31.3, 29.4, 23.9, 21.2. HRMS (ESI+) m/z calc. for (M+H)$^+$ [C$_{31}$H$_{37}$NO$_2$+H]$^+$: 456.2903, found: 456.2903.

5-(3-Methoxyphenyl)-2-phenethyl-2-azabicyclo[3.3.1] nonan-8-yl)methanol (34). To a solution of benzyl ether 33 (3.00 g, 6.60 mmol) in ethanol (66.0 mL) was added acetic acid (0.189 mL, 3.30 mmol) and Pd/C Escat (76 mg per mmol of 33) then heated in a Parr shaker apparatus overnight at ca. 50° C. The next day the black suspension was allowed to cool to room, purged with nitrogen, and filtered through celite (EtOH eluent). The volatiles were removed via rotary evaporation and primary alcohol 34 was obtained as a colorless oil (2.40 g, >99% yield). $R_f$=0.32 in 90:9:1 CHCl$_3$/MeOH/conc. NH$_4$OH, visualized with iodine stain. $^1$H NMR (400 MHz, CDCl$_3$): δ 7.31-7.18 (comp. m, 6H), 6.90 (d, J=8.0 Hz, 1H), 6.85 (t, J=2.1 Hz, 1H), 6.74 (dd, J=8.0, 2.1 Hz, 1H), 3.81 (s, 3H), 3.62 (dd, J=10.5, 6.6 Hz, 1H), 3.56-3.48 (m, 2H), 3.10 (app. dd, J=8.1, 5.1 Hz, 1H), 3.00-2.85 (comp. m, 4H), 2.21 (app. dt, J=13.4, 7.0 Hz, 1H), 2.06-1.76 (comp. m, 8H), 1.47 (app. dq, J=13.3, 6.7 Hz, 1H); $^{13}$C NMR (100 MHz, DMSO-d$_6$): δ 159.3, 154.3, 140.8, 129.2, 128.8, 128.2, 125.8, 117.0, 111.0, 110.5, 64.4, 56.6, 54.9, 53.7, 48.7, 47.1, 37.8, 34.6, 34.4, 33.9, 33.1, 23.5. HRMS (ESI+) m/z calc. for (M+H)$^+$[C$_{24}$H$_{31}$NO$_2$+H]$^+$: 366.2433, found: 366.2429.

3-(8-(Hydroxymethyl)-2-phenethyl-2-azabicyclo[3.3.1] nonan-5-yl)phenol (35). Methoxy arene 34 (567 mg, 1.55 mmol) was dissolved in methylene chloride (13 mL) and cooled to −78° C. BBr$_3$ (0.50 mL, 4.65 mmol) was added slowly dropwise to the reaction mixture and the reaction flask was removed from the dry-ice acetone bath to allow for gradual warming to ambient temperature over an hour. The reaction mixture was quenched with methanol (5 mL) at 0° C. and transferred to a separatory funnel while diluting with water (10 mL) and chloroform (5 mL). Concentrated NH$_4$OH was added and the aqueous layer was extracted with a 9:1 mixture of CHCl$_3$/MeOH (5×15 mL). The combined organic layers were washed with brine, dried over Na$_2$SO$_4$, filtered and concentrated. The crude residue was purified via flash chromatography (90:9:1 CHCl$_3$/MeOH/conc. NH$_4$OH) to yield phenol 35 (544 mg, >99% yield) as colorless oil that solidified upon standing. 35 was further converted to its HBr salt by dissolving in minimum amounts of acetone and treating with aqueous HBr, mp 228-230° C. (HBr salt). $R_f$ (free base)=0.32 in 90:9:1 CHCl$_3$/MeOH/conc. NH$_4$OH, visualized with iodine stain. $^1$H NMR (free base) (400 MHz, CDCl$_3$): δ 7.31-7.12 (comp. m, 6H), 6.88 (d, J=7.8 Hz, 1H), 6.80 (br. s, 1H), 6.65 (dd, J=7.8, 2.1 Hz, 1H), 3.57 (d, J=7.3 Hz, 2H), 3.24 (br. s, 1H), 3.02-2.68 (comp. m, 6H), 2.11 (app. dt, J=11.3, 6.0 Hz, 1H), 2.03-1.71 (comp. m, 7H), 1.50 (app. td, J=13.0, 7.0 Hz, 1H); $^{13}$C NMR (HBr salt) (100 MHz, DMSO-d$_6$): δ 157.3, 151.6, 137.1, 129.4, 128.9, 128.8, 128.64, 128.56, 126.8, 115.2, 113.0, 111.7, 62.8, 55.8, 53.7, 48.1, 34.7, 33.7, 33.0, 31.9, 30.8, 29.7, 22.1. HRMS (free base) (ESI+) m/z calc. for (M+H)$^+$[C$_{23}$H$_{29}$NO$_2$+H]$^+$: 352.2277, found: 352.2272. Anal. Calc. for C$_{23}$H$_{30}$BrNO$_2$.0.1C$_3$H$_6$O.0.1H$_2$O$^+$: C, 63.6; H, 7.06; N, 3.18, found: C, 63.45; H, 6.88; N, 3.00.

Figure 8:
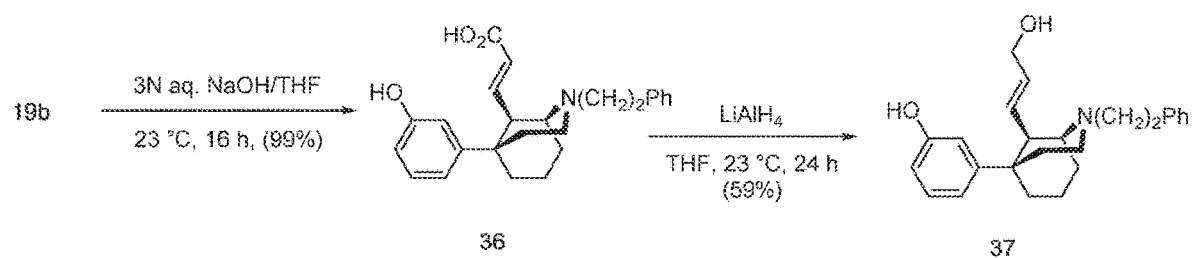
FIG. 8 shows a synthesis of exemplary compound 37.

Exemplary compound 37 was prepared according to a synthetic scheme shown in FIG. 8. The synthetic procedures for preparing compound 37 is described in FIG. 8.

Methyl (E)-3-((1S,5R,9R)-5-(3-hydroxyphenyl)-2-phenethyl-2-azabicyclo[3.3.1]nonan-9-yl)acrylate (36). A 10 mL round-bottomed flask was charged with phenylmorphan 19b (0.235 g, 0.58 mmol) and taken up in 3N aqueous NaOH (1.5 mL) and THF (1.5 mL). The reaction was stirred for 16 h at room temperature. The pH was adjusted to ~4 (litmus) with AcOH. The aqueous layer was extracted with 9:1 CHCl$_3$/MeOH (5×5 mL). The combined organic layers were dried over MgSO$_4$, filtered, and concentrated under vacuum to afford acid 36 (0.225 g, 0.57, 99%) as a white solid. $R_f$=0.18 (80:18:2 CHCl$_3$:MeOH:sat. aq. NH$_4$OH).

3-((1S,5R,9R)-9-((E)-3-Hydroxyprop-1-en-1-yl)-2-phenethyl-2-azabicyclo[3.3.1]nonan-5-yl)phenol (37, EB-1-230): A 10 mL flame-dried round-bottomed flask was charged with acid 36 (0.100 g, 0.256 mmol) and THF (5.5 mL). The flask was cooled to 0° C. and charged with LiAlH$_4$ (0.38 mL, 0.77 mmol, 2M solution in THF). The reaction was stirred at room temperature for 24 h and then cooled to 0° C. and quenched by careful addition of Na$_2$SO$_4$.10H$_2$O. The solids were then filtered through celite and the celite pad washed with 9:1 CHCl$_3$/MeOH (3×10 mL). The filtrate was concentrated and the residue was purified via flash chromatography eluting with CHCl$_3$/MeOH/sat. aq. NH$_4$OH (99:0.9:0.1 to 80:18:2) to afford phenylmorphan 37 as a white foam (0.057 g, 0.151, 59%). $R_f$=0.66 (80:18:2 CHCl$_3$/MeOH/sat. aq. NH$_4$OH); $^1$H-NMR (400 MHz; CDCl$_3$+MeOD): δ 7.32-7.23 (m, 2H), 7.19-7.14 (m, 3H), 7.10 (t, J=7.8 Hz, 1H), 6.80 (d, J=7.8 Hz, 1H), 6.75 (s, 1H), 6.59 (d, J=8.0 Hz, 1H), 5.75 (dd, J=15.3, 7.9 Hz, 1H), 5.55 (dt, J=14.5, 6.7 Hz, 1H), 3.80-3.69 (m, 2H), 3.14-3.04 (m, 3H), 2.74-2.65 (m, 5H), 2.39 (q, J=11.3 Hz, 1H), 2.30 (d, J=14.2 Hz, 1H), 2.08 (d, J=13.2 Hz, 1H), 1.92-1.86 (m, 1H), 1.84-1.69 (m, 2H), 1.69-1.61 (m, 1H), 1.56-1.53 (m, 1H); $^{13}$C NMR (101 MHz; CDCl$_3$+MeOD): δ 156.0, 151.2, 140.4, 134.3, 129.9, 129.1, 128.8, 128.3, 126.0, 117.6, 113.6, 112.8, 63.4, 58.5, 57.1, 49.6, 48.1, 42.0, 38.1, 33.4, 30.2, 25.4, 23.1; HRMS-ESI (m/z): [M+H]$^+$; [α]$^{20}_D$=+15.0° (c 0.16, CHCl$_3$). The freebase was converted to the HBr salt for analysis. Anal. Calcd. For C$_{25}$H$_{32}$BrNO$_2$.0.15H$_2$O C, 65.12%; H, 7.06%; N, 3.04%. Found C, 65.12%; H, 6.97%; N, 2.90%.

Figure 9:
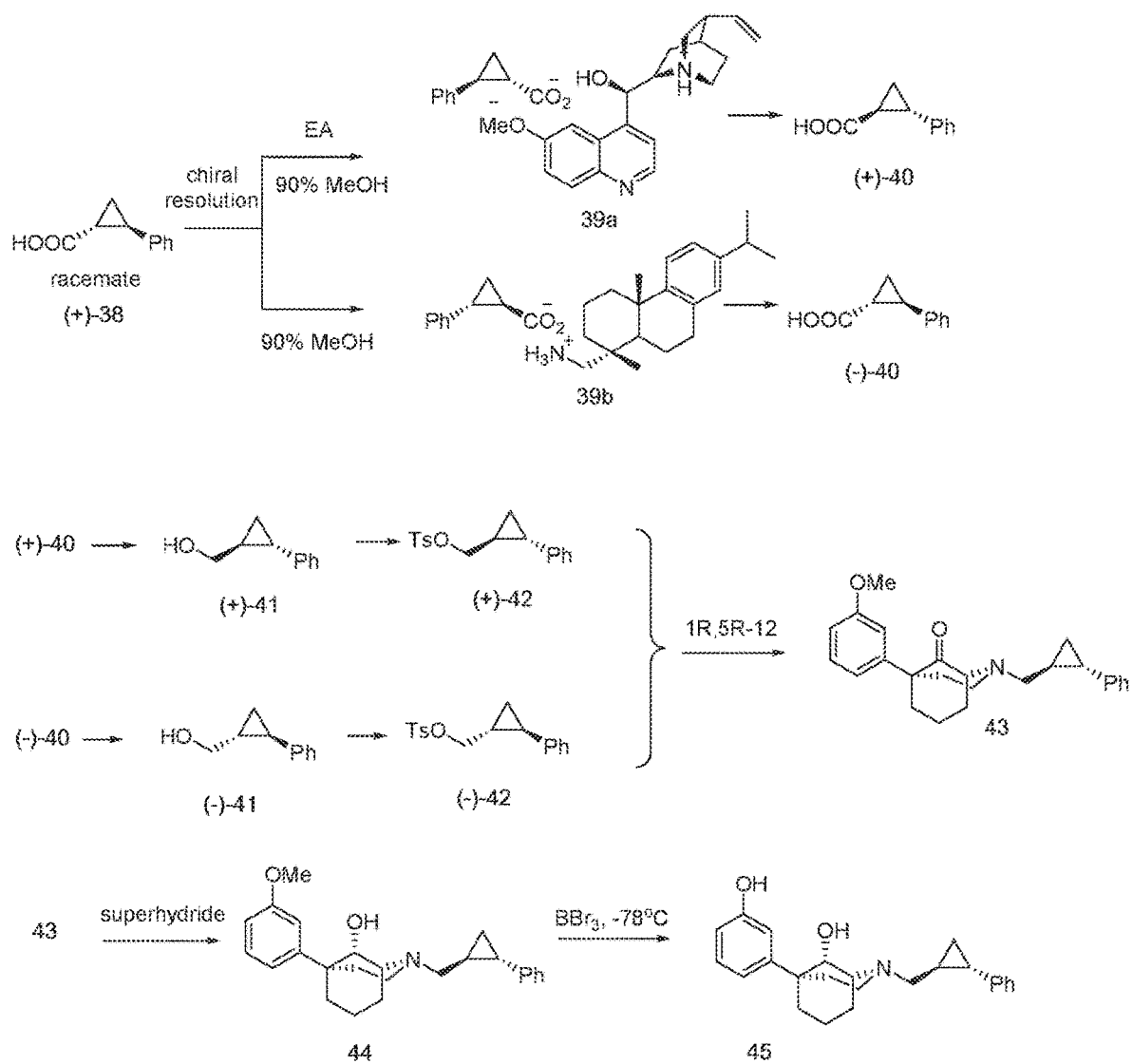
FIG. 9 shows a synthesis of exemplary compound 45.

Exemplary compound 45 was prepared according to a synthetic scheme shown in FIG. 9. The synthetic procedures for preparing compound 45 is described in FIG. 9.

(1R,5S)-5-(3-methoxyphenyl)-2-(((1S,2S)-2-phenylcyclopropyl)methyl)-2-azabicyclo[3.3.1]nonan-9-one (43). A solution of LiAlH$_4$ (1 equiv) in ether (10 mL) was added to a solution of (+)-40 or (−)-40 (3-4 mmol) in ether (10 mL) under N$_2$ at 0° C. The mixture was warmed to room temperature and stirred for 2 h. The mixture was then quenched with water and 10% aqueous NaOH solution, and extracted with ether. The organic layer was concentrated in vacuo to give crude product (+)-41 or (−)-41.

The crude product (+)-41 or (−)-41 (3-4 mmol) was dissolved in DCM (10 mL) and added trimethylamine (1.3 equiv), followed by a solution of 4-toluenesulfonyl chloride (1 equiv) and DMAP (0.1 equiv) in DCM (5 mL). The mixture was stirred at room temperature for 1 h and quenched with aqueous NH$_4$Cl solution, then extracted with ethyl acetate. The organic layer was concentrated in vacuo to give crude product 42.

A solution of 42 (3-4 mmol) and 1R,5R-8 (1.2 equiv) was dissolved in DMF (12 mL) and stirred for 2 h. The mixture was concentrated in vacuo and purified by silica gel chromatography with hexanes/EtOAc (2/1) to give 43 as a colorless oil. H NMR (400 MHz, DMSO-D$_6$) δ 7.24 (t, J=7.6 Hz, 3H), 7.14 (t, J=7.4 Hz, 2H), 7.05 (d, J=7.6 Hz, 1H), 6.83-6.76 (m, 3H), 3.78 (s, 3H), 3.41 (s, 1H), 3.31-3.26 (m, 1H), 2.83-2.76 (m, 2H), 2.59 (dd, J=12.8 Hz, 7.2 Hz, 1H), 2.47-2.32 (m, 4H), 2.24-2.12 (m, 2H), 1.77-1.62 (m, 3H), 1.27-1.20 (m, 1H), 1.01-0.96 (m, 1H), 0.87-0.82 (m, 1H); $^{13}$C NMR (100 MHz, DMSO-D$_6$) δ 214.3, 159.1, 145.9, 142.6, 128.8, 128.3, 125.6, 125.5, 119.7, 113.7, 111.2, 68.5, 61.0, 55.2, 52.8, 48.7, 40.7, 39.3, 33.5, 22.8, 21.9, 19.2, 14.7; HRMS (TOF MS ES$^+$) calcd for C$_{25}$H$_{30}$NO$_2$ (M+H$^+$) 376.2277, found 376.2278.

(1R,5S,9R)-5-(3-methoxyphenyl)-2-((trans-2-phenylcyclopropyl)methyl)-2-azabicyclo[3.3.1]nonan-9-ol (44). 1M LiBEt$_3$ solution in THF (1.5 equiv) was added to a solution of 43 (0.5-1 mmol) in dry THF (8 mL) dropwise under N$_2$ at −78° C. and stirred for 3 h. The mixture was then quenched with aqueous NH$_4$Cl solution, basified with ammonia solution, and then extracted with ether. The organic layer was concentrated in vacuo and purified by silica gel chromatography with hexanes/EtOAc (4/1 to 1/2) to give 44 as colorless oil. H NMR (400 MHz, DMSO-D$_6$) δ 7.24 (t, J=7.6 Hz, 3H), 7.13 (t, J=7.8 Hz, 2H), 7.05-7.00 (m, 3H), 6.95 (s, 1H), 6.71 (dd, J=8.2 Hz, 1.4 Hz, 1H), 4.07 (d, J=2.8 Hz, 1H), 3.78 (s, 3H), 3.17 (s, 1H), 3.02-2.99 (m, 2H), 2.71 (dd, J=12.6 Hz, 5.8 Hz, 1H), 2.54 (dd, J=12.6 Hz, 7.0 Hz, 1H), 2.37-2.22 (m, 2H), 2.05-2.01 (m, 1H), 1.91-1.79 (m, 2H), 1.73-1.66 (m, 2H), 1.62-1.49 (m, 2H), 1.21-1.16 (m, 1H), 1.00-0.95 (m, 1H), 0.86-0.81 (m, 1H); $^{13}$C NMR (100 MHz, DMSO-D$_6$) δ 159.5, 150.8, 142.7, 129.1, 128.3, 125.7, 125.5, 117.8, 112.1, 110.4, 71.5, 59.2, 58.2, 55.1, 48.4, 40.8, 40.7, 29.8, 24.5, 22.8, 22.7, 22.1, 14.5; HRMS (TOF MS ES$^+$) calcd for C$_{25}$H$_{32}$NO$_2$ (M+H$^+$) 378.2433, found 378.2428.

(1R,5S,9R)-5-(3-hydroxyphenyl)-2-((trans-2-phenylcyclopropyl)methyl)-2-azabicyclo[3.3.1]nonan-9-ol (45). 1M BBr$_3$ solution in DCM (4 equiv) was added to a solution of 44 (0.3-0.5 mmol) in dry DCM (4 mL) dropwise under N$_2$ at −78° C. The mixture was warmed to room temperature and stirred for 1 h. The mixture was then quenched with ammonia solution, heated until DCM evaporated, and then extracted with DCM. The organic layer was concentrated in vacuo and purified by silica gel chromatography with CHCl$_3$/MeOH/28% NH$_4$OH (95/4/1) to give 45 as colorless oil. $^1$H NMR (400 MHz, DMSO-D$_6$) δ 7.24 (t, J=7.6 Hz, 3H), 7.12 (dd, J=14.2 Hz, 7.0 Hz, 2H), 7.04 (d, J=7.6 Hz, 2H), 6.89 (d, J=8.0 Hz, 1H), 6.85 (s, 1H), 6.56 (d, J=7.6 Hz, 1H), 4.08 (d, J=3.6 Hz, 1H), 3.17 (s, 1H), 3.00-2.97 (m, 2H), 2.71 (dd, J=12.6 Hz, 5.8 Hz, 1H), 2.54 (dd, J=12.8 Hz, 7.2 Hz, 1H), 2.33-2.21 (m, 2H), 1.99 (d, J=13.2 Hz, 1H), 1.88-1.76 (m, 2H), 1.73-1.45 (m, 4H), 1.22-1.15 (m, 1H), 1.00-0.95 (m, 1H), 0.86-0.81 (m, 1H); $^{13}$C NMR (100 MHz, DMSO-D$_6$) δ 155.8, 150.6, 142.7, 129.3, 128.3, 125.7, 125.5, 117.5, 112.8, 112.7, 71.5, 59.2, 58.2, 48.3, 40.7, 40.6, 29.7, 24.4, 22.9, 22.6, 22.0, 14.5; HRMS (TOF MS ES$^+$) calcd for C$_{24}$H$_{30}$NO$_2$ (M+H$^+$) 364.2277, found 364.2279.

45 oxalate: The oxalate salt was formed with oxalic acid in 2-propanol; mp 188-192° C.; Calcd for C$_{24}$H$_{29}$NO$_2$·C$_2$H$_2$O$_4$·0.75C$_3$H$_8$O: C, 68.05; H, 7.48; N, 2.81; found: C, 67.67; H, 7.11; N, 2.91.

Exemplary compounds (+)-48 and (−)-48 was prepared according to a synthetic scheme shown in FIG. 10. The synthetic procedures for preparing compounds (+)-48 and (−)-48 are described in "Probes for Narcotic Receptor Mediated Phenomena. 34. Synthesis and Structure-Activity Relationships of a Potent mu-Agonist δ-Antagonist and an Exceedingly Potent Antinociceptive in the Enantiomeric C9-Substituted 5-(3-Hydroxyphenyl)-N-phenylethylmorphan Series", *J. Med. Chem.* 2007, 50, 3765-3776.

Figure 11:
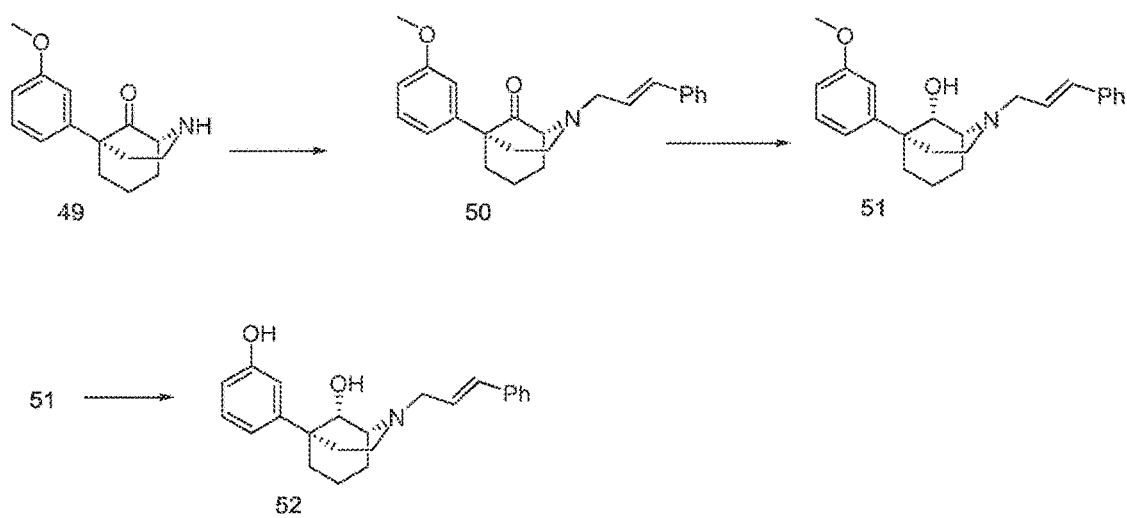
FIG. 11 shows a synthesis of exemplary compound 52.

Exemplary compound 52 was prepared according to a synthetic scheme shown in FIG. 11. The synthetic procedures for preparing compound 52 is described in FIG. 11.

The synthesis of compound 49 was reported in "Modulation of Opioid Receptor Affinity and Efficacy via N-Substitution of 9β-Hydroxy-5-(3-hydroxyphenyl)morphan: Synthesis and Computer Simulation Study", *Bioorg. Med. Chem.* 2017, 25, 2406-2422.

(1R,5R)-2-Cinnamyl-5-(3-methoxyphenyl)-2-azabicyclo[3.3.1]nonan-9-one (50). To a suspension of K$_2$CO$_3$ (12.24 mmol, 1.69 g) in anhydrous acetonitrile (50 mL) was added 49 (6.12 mmol, 1.50 g) and cooled to 0° C. Cinnamyl bromide (6.73 mmol, 1.00 mL) was then added dropwise over 15 min, and then further stirred at 0° C. for 15 min. The reaction was then quenched with H$_2$O, and extracted with DCM (3×50 mL), dried with Na$_2$SO$_4$, filtered and concentrated in vacuo. The resultant crude oil was purified by flash column chromatography on silica gel (EtOAc in hexanes, gradient 0-50%) to afford 50 as a yellow oil (1.0 g, 45% yield). $^1$H-NMR (400 MHz; CDCl$_3$): δ 7.39-7.36 (m, 2H), 7.32-7.21 (m, 4H), 6.85-6.76 (m, 3H), 6.55 (d, J=15.9 Hz, 1H), 6.25 (dt, J=15.8, 6.7 Hz, 1H), 3.79 (s, 3H), 3.48-3.38 (m, 2H), 3.35 (t, J=3.1 Hz, 1H), 3.27 (dt, J=12.0, 5.9 Hz, 1H), 2.76 (dt, J=12.6, 6.4 Hz, 1H), 2.44-2.37 (m, 4H), 2.29-2.15 (m, 2H), 1.80-1.75 (m, 1H), 1.72-1.67 (m, 1H). $^{13}$C-NMR (101 MHz; CDCl$_3$): δ 214.14 (s, 1C), 159.16 (s, 1C), 145.91 (s, 1C), 136.80 (s, 1C), 132.85 (s, 1C), 128.83 (s, 1C), 128.54 (s, 1C), 127.54 (s, 1C), 126.77 (s, 1C), 126.34 (s, 1C), 119.70 (s, 1C), 113.72 (s, 1C), 111.23 (s, 1C), 68.17 (s, 1C), 59.20 (s, 1C), 55.17 (s, 1C), 52.88 (s, 1C), 48.66 (s, 1C), 40.65 (s, 1C), 39.28 (s, 1C), 33.57 (s, 1C), 19.30 (s, 1C). [α]$^{20}_D$ +29.6° (c 1.15, CHCl$_3$).

(1R,5R,9S)-2-Cinnamyl-5-(3-methoxyphenyl)-2-azabicyclo[3.3.1]nonan-9-ol (51). To a cooled (−78° C.) solution of 50 (2.49 mmol, 900 mg) in anhydrous THF (50 mL) was added 1.0 M solution of superhydride in THF (4.15 mmol, 4.15 mL) dropwise, and stirred for 1 h. After 1 h, reaction was warmed to room temp over 1 h, then quenched with H$_2$O, and concentrated in vacuo. The resultant crude oil was dissolved in H$_2$O and CHCl$_3$, the layer separated and the aqueous extracted with CHCl$_3$ (3×50 mL), dried with Na$_2$SO$_4$, filtered and concentrated in vacuo. The resultant crude oil was purified by flash column chromatography on silica gel (10% NH$_4$OH/MeOH in CHCl$_3$, gradient 0-10%) to afford 51 as a yellow oil (630 mg, 70% yield). $^1$H-NMR (400 MHz; CDCl$_3$): δ 7.38-7.20 (m, 6H), 7.01 (d, J=7.9 Hz, 1H), 6.96 (s, 1H), 6.72 (dd, J=8.1, 2.2 Hz, 1H), 6.54 (d, J=15.9 Hz, 1H), 6.20 (dt, J=15.8, 6.7 Hz, 1H), 4.09 (s, 1H), 3.79 (s, 3H), 3.73-3.59 (m, 1H), 3.38 (d, J=6.5 Hz, 2H), 3.12 (d, J=1.7 Hz, 1H), 3.02 (dd, J=12.3, 5.1 Hz, 1H), 2.91 (dd, J=11.2, 8.4 Hz, 1H), 2.38-2.29 (m, 2H), 2.05 (t, J=7.0 Hz, 1H), 1.92-1.82 (m, 2H), 1.71-1.52 (m, 3H). $^{13}$C-NMR (101 MHz; CDCl$_3$): δ 159.53 (s, 1C), 150.70 (s, 1C), 136.89 (s, 1C), 132.11 (s, 1C), 129.13 (s, 1C), 128.53 (s, 1C), 127.62 (s, 1C), 127.44 (s, 1C), 126.28 (s, 1C), 117.87 (s, 1C), 112.19 (s, 1C), 110.41 (s, 1C), 71.61 (s, 1C), 58.04 (s, 1C), 57.36 (s, 1C), 55.11 (s, 1C), 48.37 (s, 1C), 40.87 (s, 1C), 40.69 (s, 1C), 29.79 (s, 1C), 24.57 (s, 1C), 22.73 (s, 1C). [α]$^{20}_D$ −18.0° (c 2.86, CHCl$_3$). For (1R,5R)-(+)-51, [α]$^{20}_D$ −60.5° (c 3.20, CHCl$_3$).

(1R,5R,9S)-2-Cinnamyl-5-(3-hydroxyphenyl)-2-azabicyclo[3.3.1]nonan-9-ol (52). To a cooled (−78° C.) solution of 51 (1.65 mmol, 0.60 g) in anhydrous DCM (30 mL), was added BBr$_3$ (8.26 mmol, 0.78 mL) dropwise over 10 min. The reaction was stirred at −78° C. for 30 min, and allowed to warm to room temperature by removing the dry ice bath. After 1 h at room temperature, the reaction was quenched with MeOH, then H$_2$O and 28% NH$_4$OH, and extracted with DCM (3×25 mL), dried over Na$_2$SO$_4$, filtered and concentrated in vacuo. The crude product was purified by flash column chromatography on silica gel (EtOAc in hexanes, gradient 0-100%) to afford 52 as a white foam (0.25 g, 44% yield). The oxalic acid salt was formed in 2-propanol; mp 177-181° C. $^1$H-NMR (400 MHz; CDCl$_3$): δ 7.38-7.36 (m, 2H), 7.32-7.28 (m, 2H), 7.24-7.20 (m, 1H), 7.12 (t, J=7.9 Hz, 1H), 6.89-6.86 (m, 2H), 6.58-6.52 (m, 2H), 6.21 (dt, J=15.9, 6.7 Hz, 1H), 4.14-4.09 (m, 1H), 3.38 (dd, J=6.7, 1.0 Hz, 2H), 3.13 (d, J=2.5 Hz, 1H), 3.01 (td, J=12.3, 5.2 Hz, 1H), 2.91 (dd, J=11.7, 7.9 Hz, 1H), 2.34-2.25 (m, 2H), 2.02-1.99 (m, 1H), 1.85 (td, J=10.5, 5.0 Hz, 2H), 1.68-1.47 (m, 3H). $^{13}$C-NMR (101 MHz; CDCl$_3$): δ 156.01 (s, 1C), 150.39 (s, 1C), 136.80 (s, 1C), 132.43 (s, 1C), 129.30 (s, 1C), 128.55 (s, 1C), 127.51 (s, 1C), 127.20 (s, 1C), 126.32 (s, 1C), 117.29 (s, 1C), 112.91 (s, 1C), 112.75 (s, 1C), 71.68 (s, 1C), 57.89 (s, 1C), 57.32 (s, 1C), 48.40 (s, 1C), 40.61 (s, 1C), 40.60 (s, 1C), 29.60 (s, 1C), 24.40 (s, 1C), 22.61 (s, 1C). $[α]^{20}_D$ −70.3° (c 1.74, CHCl$_3$). Calcd for C$_{23}$H$_{29}$NO$_6$·0.15C$_3$H$_8$O·0.5H$_2$O: C, 66.81; H, 6.87; N, 3.06; found: C, 66.69; H, 6.73; N, 2.92.

Figure 12:
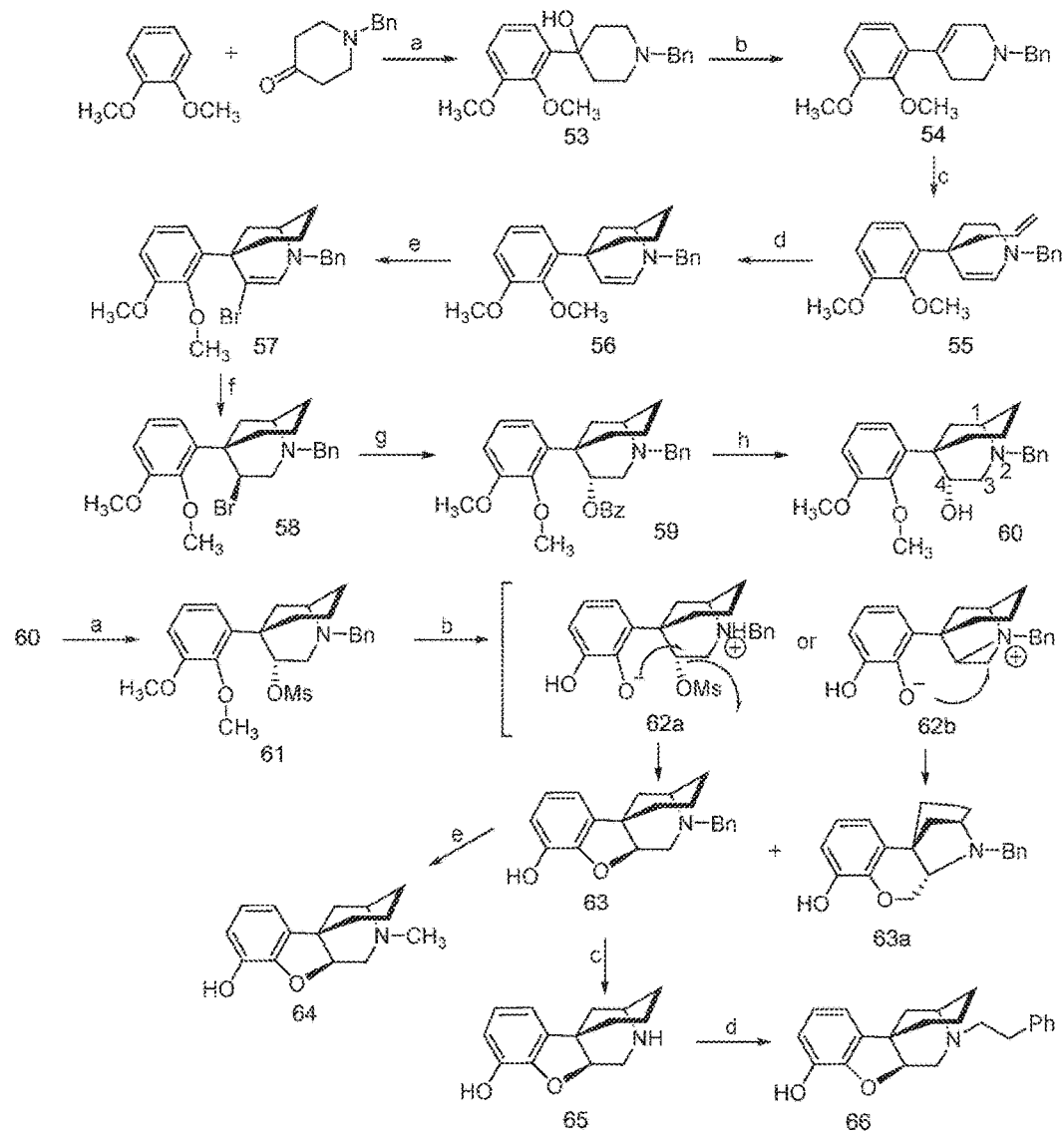
FIG. 12 shows a synthesis of exemplary compound 66.

Exemplary compound 66 was prepared according to a synthetic scheme shown in FIG. 12. The synthetic procedures for preparing compound 66 are described in "Probes for Narcotic Receptor Mediated Phenomena. 31. Synthesis of rac-(3R,6aS,11aS)-2-methyl-1,3,4,5,6,11a-hexahydro-2H-3,6a-methanobenzofuro[2,3-c]azocine-10-ol, and azocine-8-ol, the ortho-c and the para-c oxide-bridged phenylmorphan isomers", Tetrahedron 2003, 59, 4603-4614.

Exemplary compound 70 was prepared according to a synthetic scheme shown in FIG. 13. The synthetic procedures for preparing compound 70 is described in FIG. 13.

(3R*,6aS*,11aS*)-2-Benzyl-10-methoxy-1,3,4,5,6,11a-hexahydro-2H-3,6a-methano-benzofuro[2,3-c]azocine (±)-67. To a stirred suspension of compound (±)-63 (3.72 g, 11.6 mmol) and K$_2$CO$_3$ (3.2 g, 23.2 mmol) in DMF (200 mL) was added a solution of MeI (1.81 g, 0.79 mL, 12.8 mmol) dropwise and the mixture was stirred at room temperature overnight. The solvent was removed under reduced pressure and the residue was treated with H$_2$O. The mixture was extracted with CH$_2$Cl$_2$ (3×30 mL) and the combined extracts were washed with brine and dried over anhydrous Na$_2$SO$_4$. After filtration and evaporation, the crude product was purified by flash chromatography (0-10% EtOAc in hexane) to give racemic (3R*,6aS*,11aS*)-2-benzyl-10-methoxy-1,3,4,5,6,11a-hexahydro-2H-3,6a-methanobenzofuro[2,3-c]azocine (±)-67 (3.41 g, 87.7%) as white solid. $^1$H NMR (400 MHz, CDCl$_3$): δ 7.34 (d, J=6.8 Hz, 2H), 7.29 (t, J=6.8 Hz, 2H), 7.22 (d, J=8.0 Hz, 1H), 6.85 (t, J=7.6 Hz, 1H), 6.72 (t, J=7.6 Hz, 2H), 4.30 (m, 1H), 3.92 (d, J=13.6 Hz, 1H), 3.84 (s, 3H), 3.80 (d, J=14.0 Hz, 1H), 3.42 (t, J=11.2 Hz, 1H), 3.29 (m, 1H), 3.10 (s, 1H), 2.24 (d, J=12.8 Hz, 1H), 2.08 (d, J=12.0 Hz, 1H), 1.99 (t, J=12.0 Hz, 1H), 1.82 (m, 2H), 1.63 (m, 1H), 1.43 (m, 2H); $^1$H NMR (100 MHz, CDCl$_3$) δ 147.4, 145.1, 139.9, 139.5, 128.4 (2), 128.2 (2), 126.9, 121.8, 114.1, 111.2, 89.3, 58.6, 55.9, 52.4, 51.0, 44.5, 36.7, 31.9, 26.6, 21.8; ESI-MS 336.2 (M+H)$^+$; HRMS (ES$^+$) calcd for C$_{22}$H$_{26}$NO$_2$ (M+H)$^+$ 336.1958; found 336.1958.

(3R*,6aS*,11aS*)-10-Methoxy-1,3,4,5,6,11a-hexahydro-2H-3,6a-methanobenzofuro-[2,3-c]azocine (±)-68. A flask charged with compound (±)-67 (3.82 g, 11.4 mmol), 10% Pd/C (0.8 g), AcOH (10 mL) and MeOH (100 mL) was evacuated and backfilled with H$_2$ three times. The mixture was hydrogenated under H$_2$ (50 psi) at 50° C. overnight. The mixture was filtered and the filtrate was concentrated. The residue was basified with 28% NH$_4$OH and extracted with CH$_2$Cl$_2$ (3×30 mL) and the combined extracts were washed with brine and dried over anhydrous Na$_2$SO$_4$. After filtration and evaporation, the crude product was purified by flash chromatography (CHCl$_3$:MeOH:NH$_4$OH=90:9:1) to give racemic (3R*,6aS*,11aS*)-10-methoxy-1,3,4,5,6,11a-hexahydro-2H-3,6a-methanobenzofuro-[2,3-c]azocine (±)-68 (2.6 g, 92.9%) as clear oil. $^1$H NMR (400 MHz, CDCl$_3$): δ 6.85 (t, J=7.6 Hz, 1H), 6.7 (d, J=8.0 Hz, 1H), 6.69 (d, J=7.2 Hz, 1H), 4.10 (dd, J=12.0, 5.2 Hz, 1H), 3.85 (s, 3H), 3.71 (t, J=12.0 Hz, 1H), 3.35 (dd, J=12.0, 5.6 Hz, 1H), 3.27 (s, 1H), 2.16 (d, J=12.0 Hz, 1H), 2.02 (m, 1H), 1.86 (m, 2H), 1.81 (m, 2H), 1.67 (m, 2H), 1.44 (m, 1H); H NMR (100 MHz, CDCl$_3$) δ 146.7, 145.1, 139.9, 121.8, 114.0, 111.1, 90.3, 55.9, 47.7, 45.8, 44.6, 38.8, 33.2, 32.0, 21.7; ESI-MS 246.1 (M+H)$^+$; HRMS (ES$^+$) calcd for C$_{15}$H$_{20}$NO$_2$ (M+H)$^+$ 246.1489; found 246.1489.

Optical resolution of (3R*,6aS*,11aS*)-10-methoxy-1,3,4,5,6,11a-hexahydro-2H-3,6a-methano-benzofuro[2,3-c]azocine (±)-68. To a solution of the racemate (±)-68 (3.3 g, 13.4 mmol) in acetone (30 mL) was added (S)-(+)-p-methylmandelic acid (2.24 g, 13.5 mmol) and a clear solution was obtained. The solvent was evaporated under reduced pressure and the salt was treated with EtOAc (40 mL). The solution was heated up to reflux and the solvent was distilled with a Dean-Stark trap until around 20 mL of EtOAc was distilled off and a white solid appeared. The solution was cooled to room temperature overnight. A foam solid was collected (2.1 g, 37.9%). The salt was recrystallized from EtOAc (40 mL) to yield a white solid (1.61 g, 28.9%). A small portion was free-based and analyzed by chiral HPLC (ee>99%): $[α]^{20}_D$-+79.8° (CHCl$_3$, c 1.04), mp 106.4-109.5° C. The initial filtrate and mother liquors were recovered, evaporated and free-based to give (−)-6-enriched free-base (2.34 g, 70.9%), which was dissolved in acetone (30 mL) and (R)-(−)-p-methylmandelic acid (1.59 g, 9.6 mmol) was added in one portion. The solution was concentrated and the salt was crystallized from EtOAc (40 mL and 60 mL) twice to yield a foam white solid (2.6 g, 46.9%). A small portion was free-based and analyzed by chiral HPLC (ee>99%): $[α]^{20}_D$=−77.6° (CHCl$_3$, c 1.02), mp 106.4-108.8° C. The absolute stereochemistry of (3S, 6aR, 11aR)-(−)-68 was established by single crystal X-ray analysis of the (R)-(−)-p-methylmandelate salt.

(3S,6aR,11aR)-10-Methoxy-2-phenethyl-1,3,4,5,6,11a-hexahydro-2H-3,6a-methano-benzofuro[2,3-c]-azocine (−)-69. A mixture of (−)-68 (60 mg, 0.24 mmol), K$_2$CO$_3$ (101 mg, 0.73 mg), phenethyl bromide (89 mg, 66 μL, 0.48 mmol) and CH$_3$CN (5 mL) was heated at 80° C. overnight. The mixture was filtered and the filtrate was concentrated. The crude product was purified by flash chromatography (10-30% EtOAc in hexane) to give (3S,6aR,11aR)-10-methoxy-2-phenethyl-1,3,4,5,6,11a-hexahydro-2H-3,6a-methanobenzofuro[2,3-c]-azocine (−)-69 (73 mg, 84.9%) as clear oil. $^1$H NMR (400 MHz, CDCl$_3$): δ 7.28 (t, J=7.2 Hz, 2H), 7.22 (m, 3H), 6.88 (t, J=7.6 Hz, 1H), 6.77 (d, J=8.0 Hz, 1H), 6.73 (d, J=6.8 Hz, 1H), 4.10 (dd, J=11.2, 5.6 Hz, 1H), 3.89 (s, 3H), 3.43 (m, 2H), 3.20 (s, 1H), 2.93 (m, 2H), 2.84 (m, 2H), 2.20 (d, J=13.2 Hz, 1H), 2.14 (d, J=12.0 Hz, 1H), 1.99 (J=12.0 Hz, 1H), 1.79 (m, 2H), 1.62 (m, 1H), 1.46 (m, 2H); H NMR (100 MHz, CDCl$_3$) δ 147.5, 145.2, 140.5, 139.8, 128.8 (2), 128.4 (2), 126.1, 122.0, 114.2, 111.1, 89.2, 56.2, 56.0, 53.0, 51.3, 44.6, 36.9, 35.1, 31.9, 26.7, 21.9;

[α]$^{20}_D$=−72.7° (CHCl$_3$, c 1.05); ESI-MS 350.2 (M+H)$^+$; HRMS (ES$^+$) calcd for C$_{23}$H$_{28}$NO$_2$ (M+H)$^+$350.2115; found 350.2113.

(3S,6aR,11aR)-2-Phenethyl-1,3,4,5,6,11a-hexahydro-2H-3,6a-methano-benzofuro[2,3-c]azocin-10-ol ((−)-70). To a solution of BBr$_3$ (0.26 g, 0.1 mL, 1.04 mmol) in CHCl$_3$ (10 mL) at −78° C. under N$_2$ was added a solution of (3S,6aR,11aR)-10-methoxy-2-phenethyl-1,3,4,5,6,11a-hexahydro-2H-3,6a-methanobenzofuro[2,3-c]-azocine (−)-69 (73 mg, 0.21 mmol) and the resulting solution was warmed to room temperature gradually and stirred for 1 h at room temperature. The solution was cooled to −78° C. and the reaction was quenched with 28% NH$_4$OH. The mixture was extracted with CHCl$_3$ (3×10 mL) and the combined extracts were washed with brine and dried over anhydrous Na$_2$SO$_4$. After filtration and evaporation, the crude product was purified by flash chromatography (25% EtOAc in hexane) to yield (3S,6aR,11aR)-2-phenethyl-1,3,4,5,6,11a-hexahydro-2H-3,6a-methano-benzofuro[2,3-c]azocin-10-ol (−)-70 (63 mg, 87.1%) as a clear oil. $^1$H NMR (400 MHz, CDCl$_3$): δ 7.27 (m, 2H), 7.20 (m, 3H), 6.78 (t, J=7.2 Hz, 1H), 6.73 (d, J=7.2 Hz, 1H), 6.62 (d, J=6.0 Hz, 1H), 4.28 (m, 1H), 3.54 (m, 1H), 3.37 (t, J=10.8 Hz, 1H), 3.28 (s, 1H), 2.92 (m, 4H), 2.25 (d, J=12.8 Hz, 1H), 2.12 (d, J=12.0 Hz, 1H), 2.01 (d, J=12.0 Hz, 1H), 1.78 (m, 2H), 1.63 (m, 1H), 1.48 (m, 2H); H NMR (100 MHz, CDCl$_3$) δ 146.5, 141.5, 140.3, 139.6, 128.9 (2),128.5 (2), 126.2, 122.3, 116.2, 113.6, 89.0, 56.6, 52.6, 51.5, 44.4, 36.7, 34.6, 31.7, 26.3, 21.8; [α]$^{20}_D$ −46.2 (CHCl$_3$, c 1.0); ESI-MS 336.2 (M+H)$^+$; HRMS (ES$^+$) calcd for C$_{22}$H$_{26}$NO$_2$ (M+H)$^+$336.1958; found 336.1956; Anal. Calcd for C$_{22}$H$_{25}$NO$_2$.HCl.0.5H$_2$O: C, 69.37, H, 7.14, N, 3.68; Found C, 69.33, H, 7.18, N, 3.72.

Figure 14:
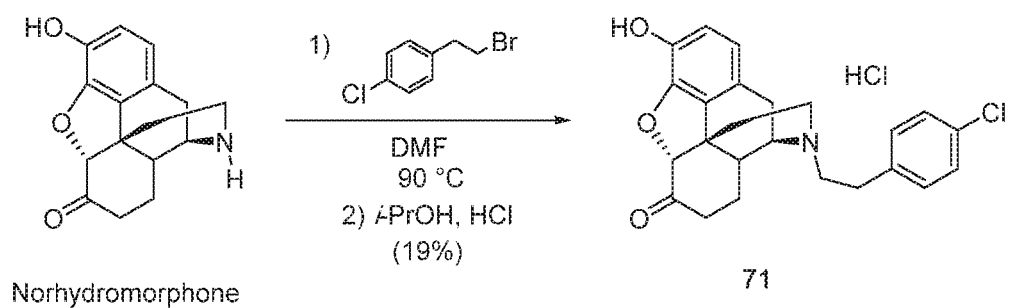
FIG. 14 shows a synthesis of exemplary compound 71.

Exemplary compound 71 was prepared according to a synthetic scheme shown in FIG. 14. The synthetic procedures for preparing compound 71 is described in FIG. 14.

3-(4-Chlorophenethyl)-9-hydroxy-2,3,4,4a,5,6-hexahydro-1H-4,12-methanobenzofuro[3,2-e]isoquinolin-7 (7aH)-one (71). A 25 ml round-bottom flask was charged with N-norhydromorphone (490 mg, 1.8 mmol), NaHCO$_3$ (650 mg, 7.7 mmol), and 7 mL DMF. The mixture was placed under Ar and stirred for 5 mins at 25° C. To this was added 0.55 mL 4-chlorophenethyl bromide (825 mg, 3.7 mmol). The mixture was then heated to 90° C. overnight. After cooling to 25° C., the solvent was removed under reduced pressure. The residue was suspended in 20 mL H$_2$O and 20 mL CHCl$_3$. The layers were separated and the aqueous layer was extracted with 3×75 mL CHCl$_3$. The combined organic extracts were dried over Na$_2$SO$_4$, filtered to remove the solid and the solvent removed under reduced pressure. Purification via column chromatography (90:9:1 CHCl$_3$:MeOH:NH$_4$OH, R$_f$=0.5) gave pure N-4-chlorophenethyl hydromorphone as a yellow oil. The oil was dissolved in 4 mL warm i-PrOH and conc. HCl was added to pH 2. The resulting crystals were isolated via vacuum filtration and gave N-4-chlorophenethyl hydromorphone hydrochloride (71) as a white solid (150 mg, 0.3 mmol, 19% yield). $^1$H-NMR (400 MHz; DMSO-d$_6$): δ 11.15-11.12 (m, 1H), 9.40 (s, 1H), 7.42 (d, J=8.3 Hz, 2H), 7.35 (d, J=8.2 Hz, 2H), 6.67 (d, J=8.1 Hz, 1H), 6.62 (d, J=8.1 Hz, 1H), 5.06 (s, 1H), 3.41-3.34 (m, 4H), 3.23-3.08 (m, 5H), 2.80-2.74 (m, 1H), 2.58 (dd, J=14.3, 4.8 Hz, 2H), 2.45-2.38 (m, 1H), 2.23-2.20 (m, 1H), 1.92-1.88 (m, 1H), 1.76 (d, J=12.7 Hz, 1H); $^{13}$C NMR (101 MHz; DMSO-d$_6$): δ 207.5, 144.0, 140.0, 136.2, 131.5, 130.7, 128.5, 125.6, 121.1, 120.0, 117.8, 89.5, 62.0, 57.5, 53.6, 45.6, 44.9, 38.1, 32.2, 29.0, 24.1, 20.1; mp: 208-210° C. (decomp); HRMS (ESI): Calc [M+H]$^+$: 410.1523, Found: 410.1520; Analysis for C$_{24}$H$_{25}$Cl$_2$NO$_3$.0.5 i-PrOH: Calc: C, 64.26; H, 6.14; N, 2.94; Found: C, 64.09; H, 6.09; N, 2.78.

Figure 15:
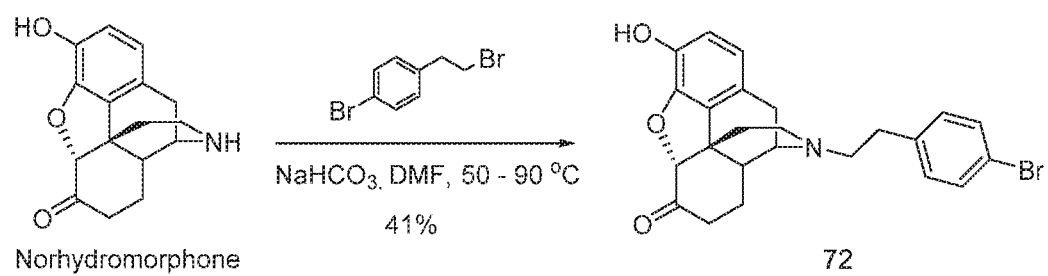
FIG. 15 shows a synthesis of exemplary compound 72.

Exemplary compound 72 was prepared according to a synthetic scheme shown in FIG. 15. The synthetic procedures for preparing compound 72 is described in FIG. 15.

3-(4-Bromophenethyl)-9-hydroxy-2,3,4,4a,5,6-hexahydro-1H-4,12-methanobenzofuro[3,2-e]isoquinolin-7 (7aH)-one (72). Norhydromorphone (0.300 g, 1.11 mmol) was added to a dry round bottom flask containing a stir bar, then placed in a vacuum oven for 2 hours. NaHCO$_3$ (0.500 g, 5.95 mmol) was added to the flask, followed by dimethylformamide (10 mL). The flask was sealed under N$_2$, then 4-bromophenethyl bromide (0.586 g, 2.22 mmol) was added via syringe. The reaction was heated to 60° C. for 20 hours, cooled to room temperature, and filtered through a pad of celite. The DMF was removed via azeotrope with toluene (3×20 mL), then purification by SiO$_2$ column chromatography with 10% NH$_4$OH in MeOH/CHCl$_3$ (0%→5% of 10% NH$_4$OH) gave 72 (0.212 g isolated, 41% yield) as a light brown oil. $^1$H NMR (400 MHz, CDCl$_3$): δ 7.39 (d, J=8.1 Hz, 2H), 7.07 (d, J=8.1 Hz, 2H), 6.71 (d, J=8.1 Hz, 1H), 6.58 (d, J=8.1 Hz, 1H), 4.65 (s, 1H), 3.34 (d, J=0.4 Hz, 1H), 2.96 (t, J=15.8 Hz, 1H), 2.78-2.69 (m, 5H), 2.65-2.61 (m, 1H), 2.38-2.32 (m, 3H), 2.27-2.21 (m, 1H), 2.16-2.07 (m, 1H), 1.84-1.76 (m, 2H), 1.27-1.18 (m, 2H); $^{13}$C NMR (400 MHz, CDCl$_3$): δ 209.12, 144.04, 139.08, 138.89, 131.39, 130.47, 126.78, 125.05, 120.26, 119.89, 118.00, 91.35, 57.67, 56.64, 47.40, 45.03, 42.11, 40.13, 35.16, 33.63, 25.41, 20.98; HRMS (TOF MS ES$^+$) Calcd for C$_{24}$H$_{24}$BrNO$_3$ (M+H$^+$) 454.1018, found 454.1021.

72 oxalate. An oxalate salt was prepared by dissolving the base in a minimal amount of hot isopropanol. A concentrated solution of oxalic acid in isopropanol was added, leading to the formation of a precipitate. The solution was allowed to cool at 5° C. overnight, then the precipitate was collected and dried to give the oxalate salt (131 mg recovered, 44% yield), mp 201-204° C. [α]$^{20}_D$ −87.0 (c 1.2, MeOH, C$_{24}$H$_{24}$BrNO$_3$.C$_2$H$_2$O$_4$.2H$_2$O salt). Anal. Calcd for C$_{24}$H$_{24}$BrNO$_3$.C$_2$H$_2$O$_4$.2H$_2$O: C, 54.31%; H, 5.15%; N, 2.44%; found: C, 54.09%; H, 5.04%; N, 2.71.

The molecular structure, agonist potency, and bias factor of some biased agonists are indicated in Table 2:

TABLE 2

| Cmpd # | Molecular Structure | MOR cAMP Agonist Potency ± SEM (nM) (% Efficacy)$^a$ | MOR Mediated B-arrestin Recruitment (% Control, Emax DAMGO), nM$^b$ | Bias Factor$^c$ |
|---|---|---|---|---|
| 12 | 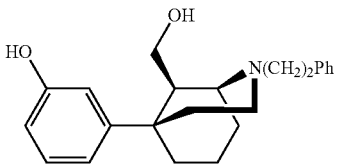 | 3.8 ± 1.4 (26% ± 4.3%) | >25000 | 2028 |

TABLE 2-continued

| Cmpd # | Molecular Structure | MOR cAMP Agonist Potency ± SEM (nM) (% Efficacy)[a] | MOR Mediated B-arrestin Recruitment (% Control, Emax DAMGO), nM[b] | Bias Factor[c] |
|---|---|---|---|---|
| 15 | 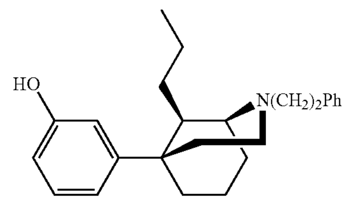 | 0.95 ± 0.35 (63.3%) | >25000 | 23,442 |
| 22 | 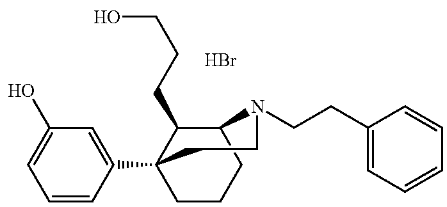 [SMILES: OCCC[C@H]1[C@@H]2CCC[C@]1(c1cccc(O)c1)CCN2CCc1ccccc1 ; Br] | 1.2 ± 0.37 (65%) | >25000 | 18.199 |
| 26 | 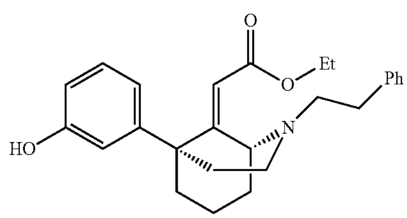 [SMILES: CCOC(=O)/C=C1\[C@H]2CCC[C@]1(c1cccc(O)c1)CCN2CCc1ccccc1] | 5.59 ± 1.25 (100.3 ± 0.8) | 29103 ± 18474 (22.2 ± 6%) | 179 |
| 27 | 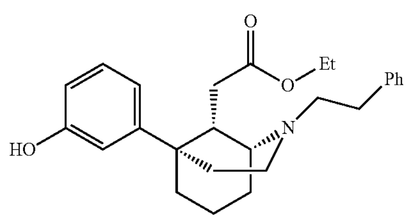 [SMILES: CCOC(=O)C[C@@H]1[C@H]2CCC[C@]1(c1cccc(O)c1)CCN2CCc1ccccc1] | 14.55 ± 3.99 (90.4 ± 3.2) | 175 ± 42.6 (1.5 ± 0.09%) | 6.7 |
| 28 | 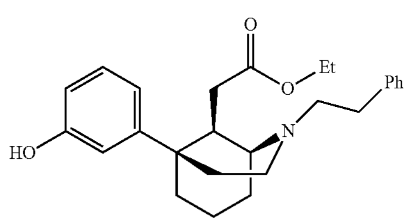 [SMILES: CCOC(=O)C[C@H]1[C@@H]2CCC[C@@]1(c1cccc(O)c1)CCN2CCc1ccccc1] | 3.97 ± 1.8 (78%) | 58.8 ± 34.7 (2.182 ± 0.08%) | 4.8 |
| 35 | 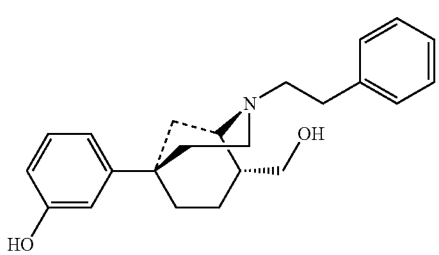 | 3.07 ± 2.2 (10.94 ± 3.1%) | >25000 | 1254 |

TABLE 2-continued

| Cmpd # | Molecular Structure | MOR cAMP Agonist Potency ± SEM (nM) (% Efficacy)[a] | MOR Mediated B-arrestin Recruitment (% Control, Emax DAMGO), nM[b] | Bias Factor[c] |
|---|---|---|---|---|
| 37 | (structure) | 2.31 ± 0.78 (33.5 ± 5.9) | >25000 | 6794 |
| Morphine | | 5.2 ± 0.4 (100%) | 380 ± 40 (38 ± 1%) | 0.36 |
| DAMGO | | 0.6 ± 0.1 (100%) | 64 ± 4 | 1 |
| PZM 21 | | 2.5 ± 0.39 (101%) | 46.2 ± 7.8 (4.4 ± 0.5%) | 0.336121 |

[a] Inhibition of Forskolin-Induced cAMP Accumulation (HitHunter ™)
[b] β-Arrestin Recruitment (PathHunter ™)
[c] Bias factor - see experimental Forskolin-stimulated cAMP accumulation assay (disclosed in Ho et al., Sci. Signal. 11, eaar4309 (2018)). Four thousand cells per well were split into 384-well low-volume plate (VWR) with Opti-MEM (Invitrogen) supplemented with 1% FBS for 3 hours at 37° C. except SH-SY5Y-hMOR cells, which were plated for 1 hour at 37° C. Cells were then treated with drugs, 25 mM 4-(3-butoxy-4-methoxybenzyl) imidazolidin-2-one (PDE4 inhibitor), and 20 mM forskolin for 30 min at room temperature.

For membrane-based inhibition of cAMP accumulation assay, membrane preparation was adapted from Allen et al. Briefly, CHO-hMOR cells were incubated in serum-free DMEM/F12 media for 60 min. Cells were then homogenized by a Dounce homogenizer 15 times in an ice-cold buffer [50 mM Hepes (pH 7.4)], followed by centrifugation at 500 g at 4° C. for 5 min. The supernatant was transferred to a 1.5-ml tube on ice, and the pellet was resuspended, homogenized, and centrifuged at 500 g at 4° C. for 5 min. Then, the supernatant was combined and spun at 20,000 g at 4° C. for 10 min. The membrane pellet was resuspended in an ice-cold buffer [50 mM Hepes (pH 7.4)] at concentrations of 2 to 4 mg protein/l. Membranes were stored at −80° C. until use. For forskolin-stimulated cAMP accumulation assay, membranes were diluted in an assay buffer (50 mM Hepes, 10 mM MgCl$_2$, 100 mM NaCl, 200 mM adenosine 5'-triphosphate, 10 mM GTP, 100 mM 3-isobutyl-1-methylxanthine, 20 mM forskolin, and 30 mM bovine serum albumin) and plated at 2 mg of protein in each well. Membranes were treated with test compounds for 30 min at room temperature. The cAMP levels were determined as per the manufacturer's instructions (Cisbio cAMP HiRange assay).

The PathHunter β-arrestin assay. The assay was performed according to the manufacturer's protocol (DiscoveRx) and as described previously. Briefly, 5000 U2OS-β-arrestin2-EFC-hMOR cells were plated in 384-well white plates with Opti-MEM media (Invitrogen) containing 1% FBS±pertussis toxin (100 ng/ml) overnight. The next day, cells were treated with compounds for 90 min at 37° C., followed by a 1-hour incubation of detection reagent at room temperature. Luminescence values were determined by using a Synergy HT luminometer (BioTek).

For β-arrestin2-GFP confocal imaging, 5000 U2OS-β-arrestin2-GFP-mMOR cells were split into a 384-well plate with MEM (Invitrogen) supplemented with 10% FBS in 37° C. incubator overnight. The cells were then serum-starved in MEM for 30 min, followed by 20-min drug treatment at 37° C., and 30-min 4% paraformaldehyde fixation and Hoechst staining at room temperature. Each condition was duplicated, and one image in each well was acquired by using an Olympus FluoView IX81 confocal microscope (Olympus).

Bias Factor calculated by Eq. 1:

$$\log(\text{bias factor}) = \left(\log\left(\frac{\text{Emax}_{test} \times EC50_{DAMGO}}{EC50_{test} \times \text{Emax}_{DAMGO}}\right)\right)_{cAMP} - \left(\log\left(\frac{\text{Emax}_{test} \times EC50_{DAMGO}}{EC50_{test} \times \text{Emax}_{DAMGO}}\right)\right)_{\beta-arrestin}$$

The molecular structure, agonist potency, and bias factor of some biased agonists are indicated in Table 3:

TABLE 3

| Cmpd # | Molecular Structure | MOR cAMP Agonist Potency ± SEM (nM) (% Efficacy)[c] | MOR Mediated B-arrestin Recruitment (% Control, Emax DAMGO), nM[d] | Bias Factor[e] |
|---|---|---|---|---|
| 45 | 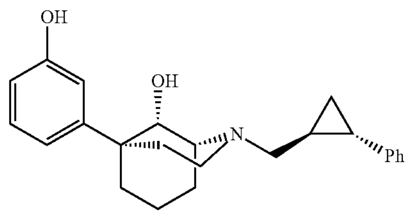 [SMILES: Oc1cccc([C@]23CCC[C@H]([C@H]2O)N(C[C@H]2C[C@@H]2c2ccccc2)CC3)c1] | 0.12 ± 0.02 (100%) | 22 ± 2 (22 ± 1%) | 6.1 |
| (−)-48 | 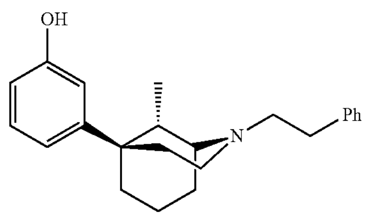 | 12.13 ± 4.01 (71%) | >25000 | 2056 |
| (+)-48 | 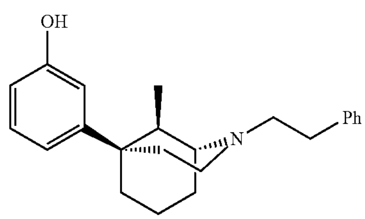 [SMILES: C[C@H]1[C@H]2CCC[C@@]1(c1cccc(O)c1)CCN2CCc1ccccc1] | 0.4 ± 0.12 (91%) | 7.72 ± 4.6 (1.8 ± 0.2%) | 6.7 |
| 52 | 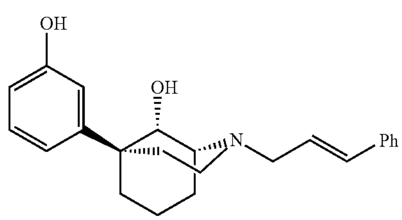 [SMILES: Oc1cccc([C@@]23CCC[C@H]([C@H]2O)N(C/C=C/c2ccccc2)CC3)c1] | 0.13 ± 0.02 (100%) | >25000 | 27.120 |
| 70 | 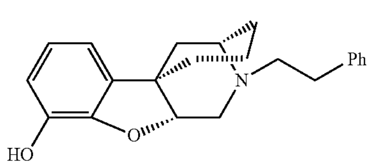 | 0.50 ± 0.24 (32.8 ± 5.2%) | >25000[a] | 21454 |

[c] Inhibition of Forskolin-Induced cAMP Accumulation (HitHunter ™)

[d] β-Arrestin Recruitment (PathHunter ™)

[e] Bias factor - see experimental for Table 3.

Table 4 lists agonists that are potent at μ and δ opioid receptors based on N-norhydromorphone[a]

TABLE 4

| Cmpd # | Molecular Structure | MOR cAMP Agonist Potency ± SEM (nM) (% Efficacy)[b] | MOR Mediated B-arrestin Recruitment (% Control, Emax DAMGO), nM[c] | Bias Factor[d] |
|---|---|---|---|---|
| 71 | (structure with Cl) | 0.05 ± 0.03 (98.8%) | 2.44 ± 0.45 (44.8 ± 1.8%) | 0.82 |
| 72 | (structure with Br) | 0.15 ± 0.04 (103 ± 1.5%) | Being tested | Being tested |

Compound 71 does not have a Bias Factor that would predict it to have fewer side-effects than known clinically used analgesics like morphine, oxycodone, or codeine. However, it has been found to have a δ/β (in vitro potency ratio at δ and μ opioid receptors) of approximately 1, an unusually low ratio. And in an in vivo assay in mice for respiratory depression (by Dr. M. Adler's group at Temple University), it was found that Compound 71 did not depress respiration in an equi-analgesic dose range of morphine—and morphine did repress respiration in that assay. This could be attributed to the effect of the ligand at the δ receptor as an agonist since the literature (Su, Y-F et al. "Delta-Opioid Ligands Reverse Alfentanil-Induced Respiratory Depression but Not Antinociception", J. Pharmacol. Exp. Ther., 1998, 287, 815-823 notes that both agonist and antagonist δ ligands can be shown to increase respiration sufficiently to overcome the depressant effects of μ ligands like morphine. A para-bromophenethyl analog of Compound 71, Compound 72, was found to be a potent μ agonist and have a low δ/μ ratio of approximately 5. It is possible that it will also cause less respiratory depression than an equi-analgesic amount of morphine. These two compounds are not in the phenylmorphan class of analgesics, but rather a derivative of hydromorphone.

Respiratory Depression Experimental Data for Compound 71.

Methods

Measurement of respiration rate and arterial oxygen saturation. Male Swiss-Webster mice (30-36 g, Taconic Biosciences, Germantown, N.Y.) were used. They were housed (five in a cage) in a temperature-controlled environment with a 12-hour light-dark cycle and were supplied with food and water ad libitum. Mice were acclimated for a week in the central animal facility before behavioral testing. On the day of the experiment, mice were brought to the room and acclimated for 45-60 min in the observation boxes. Respiration and oxygen saturation ($SpO_2$) were measured using MouseOx Plus Rat and Mouse Pulse Oximeter (Starr Life Sciences Corp, Oakmont, USA) in conscious, freely moving animals. Animals were exposed to 4% isoflurane for 30 seconds to connect throat collar sensor and to inject (s.c.) either saline, morphine 10 mg/kg, or Compound 71 0.01-0.1 mg/kg (n=6-8). Mice were then placed into observation boxes and recording was started 5 min later to eliminate any anesthesia effect. Respiration and $SpO_2$ were recorded every second and averaged over 1-min periods for 40 min. Morphine, 10 mg/kg, was used as a positive control (Hill et. al. British Journal of Pharmacology, 2018, 175 2653-2661).

Statistical Analysis

Area under the curve (AUC) was calculated from 6 min to 45 min and analyzed using one-way analysis of variance (ANOVA) followed by Dunnett's multiple comparison test. Data are expressed as mean±standard error of the mean (S.E.M.), and $p < 0.05$ was accepted as statistically significant. GraphPad Prism, version 7, was used for data analysis.

Results

Figure 16:
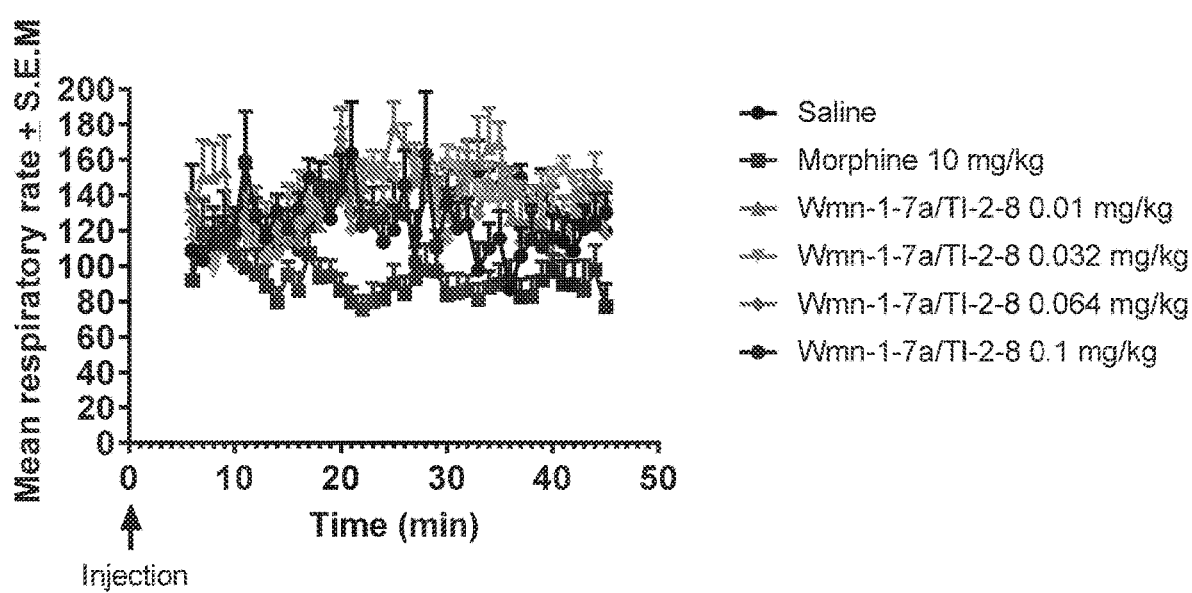
FIG. 16 is a graph showing time courses of saline, morphine (10 mg/kg), and different doses of Compound 71 on respiration rate.
Figure 17:
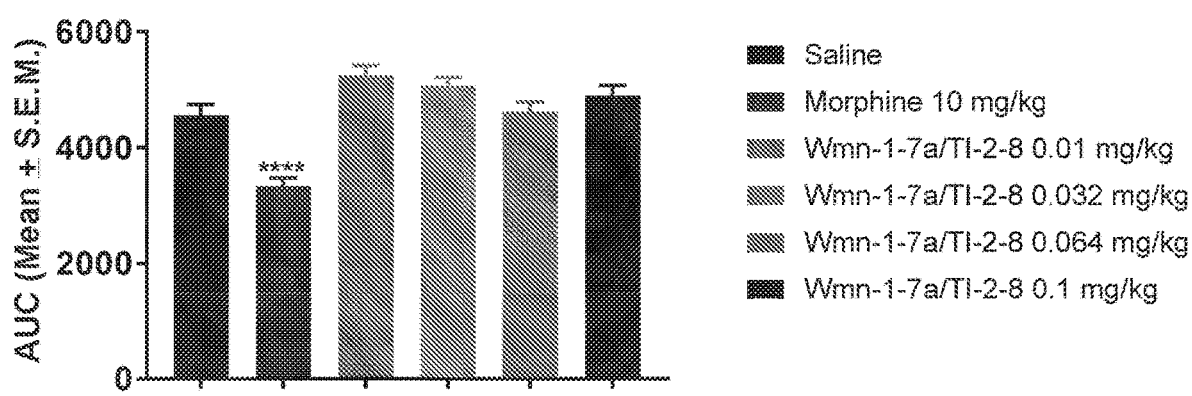
FIG. 17 is a bar graph showing calculated AUCs of saline, morphine (10 mg/kg), and different doses of Compound 71 from 6 min to 45 min post injection.
Figure 18:
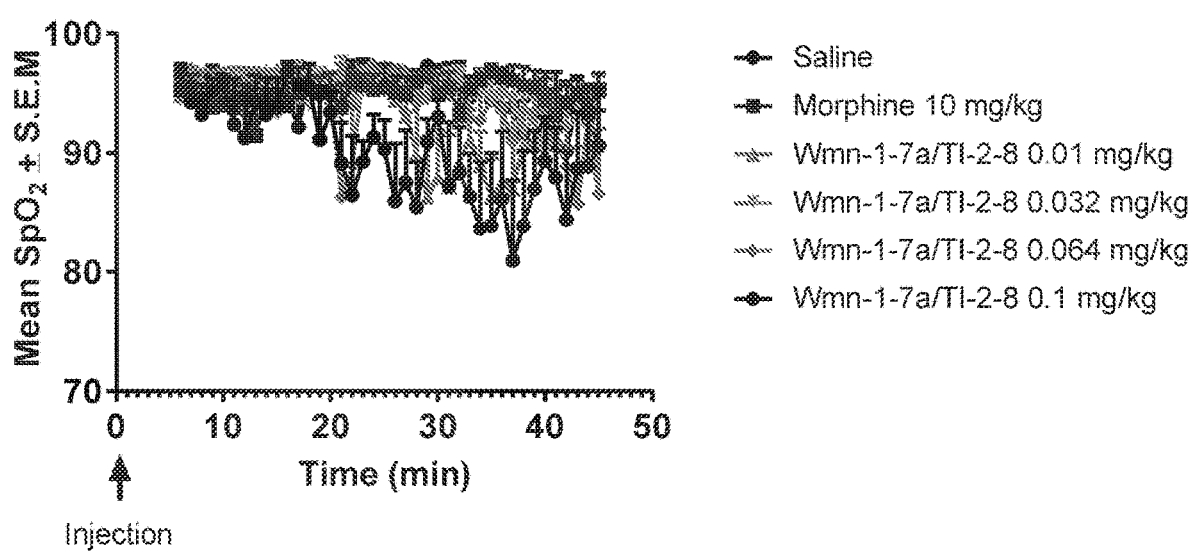
FIG. 18 is a graph showing effects of saline, morphine, and various doses of Compound 71 on $SpO_2$.
Figure 19:
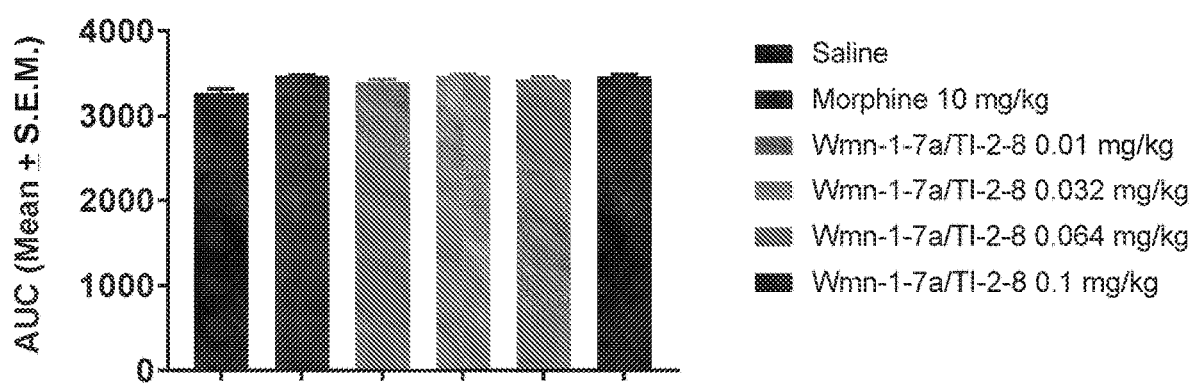
FIG. 19 is a bar graph showing calculated AUCs of saline, morphine (10 mg/kg), and different doses of Compound 71 from 6 min to 45 min post injection.

FIG. 16 shows time courses of saline, morphine (10 mg/kg), and different doses of Compound 71 on respiration rate. FIG. 17 shows calculated AUCs from 6 min to 45 min post injection. As seen in FIG. 17, 10 mg/kg morphine significantly reduced ($p < 0.001$) respiration rate compared to saline (One-way ANOVA revealed a significant effect for treatment $F(5.38)=18.34$, $p < 0.0001$). Compound 71 (0.01-0.1 mg/kg) had no effect on respiration rate. Results for $SpO_2$ were shown in FIG. 18 as a time course and in FIG. 19 as calculated AUC. Neither morphine nor Compound 71 had any effect on $SpO_2$.

The present invention has been described in terms of exemplary principles and embodiments, but those skilled in the art will recognize that variations may be made and equivalents substituted for what is described without departing from the scope and spirit of the disclosure as defined by the following claims.

What is claimed is:

1. A compound having Formula (I) or its enantiomer:

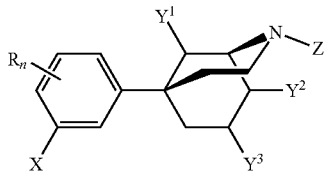
(I)

wherein in Formula (I),

X is —OH;

$Y^2$ and $Y^3$ are each independently H, $C_1$-$C_{10}$ alkyl, or —$(CR^3R^4)_{m2}V$, and $Y^1$ is —$(CR^3R^4)_{m2}V$, —$O(CR^3R^4)_{m2}V$, or —$N(CR^3R^4)_{m2}V$; wherein $R^3$ and $R^4$ are each independently H, a substituted or unsubstituted $C_1$-$C_{30}$ alkyl, a substituted or unsubstituted $C_1$-$C_{30}$ alkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, a substituted or unsubstituted $C_3$-$C_{30}$ cycloalkyl, a substituted or unsubstituted $C_3$-$C_{30}$ cycloalkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, a substituted or unsubstituted $C_6$-$C_{30}$ aryl, or a substituted or unsubstituted $C_1$-$C_{30}$ heteroaryl;

V is —$COR^5$, —$C(O)OR^5$, —$OC(O)OR^5$, —$OR^5$, —$C(O)NR^5R^6$, —$OC(O)NR^5R^6$, —$NR^5R^6$, wherein each $R^5$ is H, a substituted or unsubstituted $C_1$-$C_{30}$ alkyl, a substituted or unsubstituted $C_1$-$C_{30}$ alkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, a substituted or unsubstituted $C_3$-$C_{30}$ cycloalkyl, a substituted or unsubstituted $C_3$-$C_{30}$ cycloalkyl wherein at least one —$CH_2$— is replaced with —$S(=O)_2$—, —$C(=O)$—, —O—, —S—, —$S(=O)$—, —$C(=O)O$—, —$C(=O)NR'$— wherein R' is hydrogen or a C1 to C10 linear or branched alkyl group, —NR'— wherein R' is hydrogen or a C1 to C10 linear or branched alkyl group, or a substituted or unsubstituted $C_6$-$C_{30}$ aryl; and each $R^6$ is H, a substituted or unsubstituted $C_1$-$C_{30}$ alkyl, a substituted or unsubstituted $C_3$-$C_{30}$ cycloalkyl, a substituted or unsubstituted $C_2$-$C_{30}$ alkanoyl, a substituted or unsubstituted $C_4$-$C_{30}$ cycloalkanoyl, or a substituted or unsubstituted $C_6$-$C_{30}$ aryl; and m2 is an integer of 1 to 10; and Z is H, -L-W, or —$(CR^7R^8)_{m3}W$; wherein L is a substituted or unsubstituted $C_2$-$C_{10}$ alkenyl or a substituted or unsubstituted $C_2$-$C_{10}$ alkynyl;

$R^7$ and $R^8$ are each independently H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl, wherein any two selected from $R^7$ and $R^8$ are optionally bonded together to form a ring;

W is H, a substituted or unsubstituted $C_1$-$C_{30}$ alkyl, a substituted or unsubstituted $C_3$-$C_{30}$ cycloalkyl, a substituted or unsubstituted $C_6$-$C_{30}$ aryl, or a substituted or unsubstituted $C_1$-$C_{30}$ heteroaryl; and m3 is an integer of 1 to 10;

R is hydrogen, halogen or a substituted or unsubstituted $C_1$-$C_{30}$ alkyl; and n is an integer of 1 to 4.

2. The compound of claim 1 or its enantiomer, wherein Formula (I) is represented by Formula (Ia):

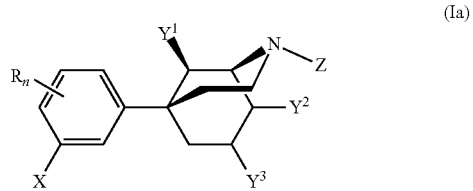
(Ia)

wherein in Formula (Ia), R, X, $Y^1$, $Y^2$, $Y^3$, Z, and n are the same as in claim 1.

3. The compound of claim 1 or its enantiomer, wherein Formula (I) is represented by Formula (Ib):

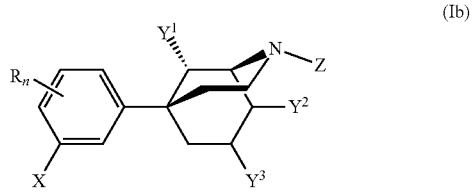
(Ib)

wherein in Formula (Ib), R, X, $Y^1$, $Y^2$, $Y^3$, Z, and n are the same as in claim 1.

4. The compound of claim 1 or its enantiomer, wherein $Y^1$ is —$(CR^3R^4)_{m2}V$, wherein $R^3$ and $R^4$ are each independently H or a substituted or unsubstituted $C_1$-$C_{30}$ alkyl; and V is —$C(O)OR^5$, —$NR^5R^6$, or $OR^5$, wherein $R^5$ and $R^6$ are each independently H or a substituted or unsubstituted $C_1$-$C_{30}$ alkyl.

5. The compound of claim 1 or its enantiomer, wherein Z is —$(CR^7R^8)_{m3}W$, wherein $R^7$ and $R^8$ are each H, W is a substituted or unsubstituted $C_6$-$C_{30}$ aryl, and m is an integer of 1 to 5.

6. The compound of claim 1 or its enantiomer, wherein Z is —$CH_2CH_2W$, wherein W is unsubstituted $C_6$-$C_{30}$ aryl, $C_6$-$C_{30}$ aryl substituted with —F, —Cl, —Br, —OH, —$NH_2$ or —$NO_2$, unsubstituted $C_1$-$C_{30}$ heteroaryl, or $C_1$-$C_{30}$ heteroaryl substituted with —F, —Cl, —Br, —OH, —$NH_2$ or —$NO_2$.

7. The compound of claim 1 or its enantiomer, wherein Formula (I) is represented by Formula (II):

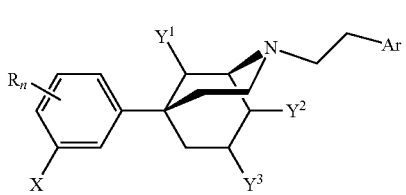

wherein in Formula (II), R, X, $Y^1$, $Y^2$, $Y^3$, and n are the same as in claim 1, and Ar is a substituted or unsubstituted $C_6$-$C_{30}$ aryl.

8. The compound of claim 1 or its enantiomer, wherein Formula (I) is represented by Formula (III):

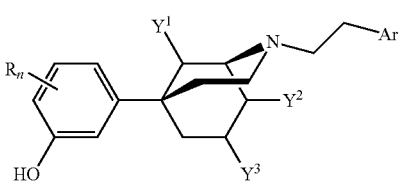

wherein in Formula (III), R, $Y^1$, $Y^2$, $Y^3$, and n are the same as in claim 1, and Ar is a substituted or unsubstituted $C_6$-$C_{30}$ aryl.

9. The compound of claim 1 or its enantiomer, wherein $R^3$ and $R^4$ are each independently H, and $Y^3$ is hydrogen.

10. The compound of claim 1 or its enantiomer, wherein m2 is 2 or 3.

11. The compound of claim 1 or its enantiomer, wherein R is H or halogen.

12. The compound of claim 1 or its enantiomer, wherein Formula (I) is represented by Formula (IV):

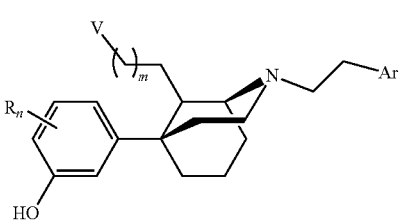

wherein in Formula (IV), R, V, and n are the same as in claim 1, Ar is a substituted or unsubstituted $C_6$-$C_{30}$ aryl, and m is an integer of 1 to 5.

13. The compound of claim 1 or its enantiomer, wherein Formula (I) is represented by Formula (V):

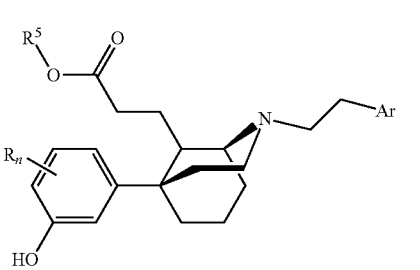

wherein in Formula (V),
R and n are the same as in claim 1,
Ar is a substituted or unsubstituted $C_6$-$C_{12}$ aryl, and
$R^5$ is a substituted or unsubstituted $C_1$-$C_5$ alkyl.

14. The compound of claim 1 or its enantiomer, wherein Formula (I) is represented by Formula (VI):

wherein in Formula (VI),
R and n are the same as in claim 1, and
Ar is a substituted or unsubstituted $C_6$-$C_{12}$ aryl.

15. A pharmaceutical composition, comprising a therapeutically effective amount of the compound of claim 1 or its enantiomer together with a pharmaceutically acceptable carrier.

16. The pharmaceutical composition of claim 15, wherein the pharmaceutically acceptable carrier is selected from the group consisting of binders, buffering agents, coloring agents, diluents, disintegrants, emulsifiers, flavorants, glidants, lubricants, preservatives, stabilizers, surfactants, tableting agents, and wetting agents, and combinations thereof.

17. The pharmaceutical composition of claim 16, further comprising a therapeutically effective amount of an opioid.

18. The pharmaceutical composition of claim 17, wherein the opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, or a combination thereof.

19. A method of prevention or treatment of pain, comprising administering to the patient a composition comprising a therapeutically effective amount of the compound of claim 1 or its enantiomer, optionally in combination with one or more additional active ingredients.

20. The method of claim 19, wherein the one or more additional active ingredient is an opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol, or a combination thereof.

21. The method of claim 19, wherein the patient is a human.

22. The method of claim 19 wherein the pain is associated with a gastrointestinal dysfunction.

23. The method of claim 22, wherein the gastrointestinal dysfunction is irritable bowel syndrome, opioid-bowel dysfunction, colitis, post-operative and opioid-induced emesis, decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

24. The method of claim 19, wherein the pain is associated with post-operative or opioid-induced ileus.

25. A compound selected from the group consisting of:

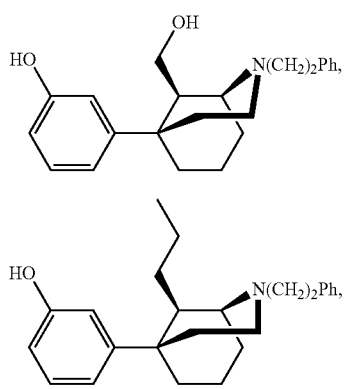

(Compound 12)

(Compound 15)

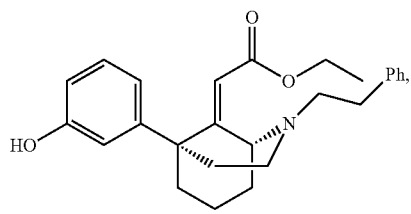

(Compound 26)

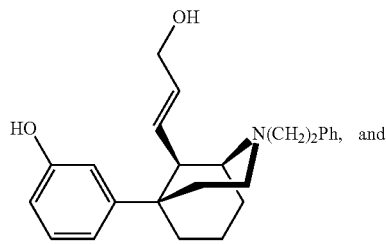

(Compound 37)

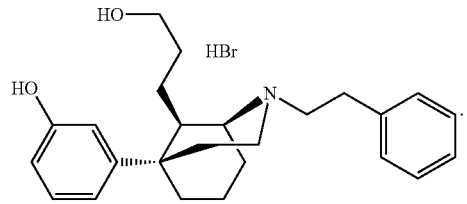

(Compound 22)

* * * * *